(12) United States Patent
Berzofsky et al.

(10) Patent No.: US 7,094,405 B1
(45) Date of Patent: Aug. 22, 2006

(54) PEPTIDES WHICH ELICIT A HIGH NEUTRALIZING ANTIBODY TITER, CYTOTOXIC T LYMPHOCYTE RESPONSE AND T HELPER CELL RESPONSE IN A BROAD RANGE OF MHC TYPE RECIPIENTS

(75) Inventors: Jay A. Berzofsky, Bethesda, MD (US); Jeffrey D. Ahlers, Kensington, MD (US); C. David Pendleton, Bethesda, MD (US); Peter Nara, Frederick, MD (US); Mutsunori Shirai, Kagawa (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/455,076

(22) Filed: Dec. 6, 1999

Related U.S. Application Data

(60) Division of application No. 08/060,988, filed on May 14, 1993, which is a continuation-in-part of application No. 07/751,998, filed on Aug. 29, 1991, now abandoned, and a continuation-in-part of application No. 07/847,311, filed on Mar. 6, 1992, now Pat. No. 5,976,541, and a continuation-in-part of application No. 07/492,318, filed on Feb. 28, 1990, now Pat. No. 5,081,226, which is a continuation-in-part of application No. 07/148,692, filed on Jan. 26, 1988, now abandoned, which is a continuation of application No. 07/014,430, filed on Feb. 12, 1987, now abandoned, which is a continuation-in-part of application No. 06/947,935, filed on Dec. 30, 1986, now abandoned.

(51) Int. Cl.
*A61K 39/21* (2006.01)

(52) U.S. Cl. .............................. 424/188.1; 424/208.1; 424/192.1; 530/324; 530/325; 530/326

(58) Field of Classification Search .............. 422/188.1, 422/208.1
See application file for complete search history.

(56) References Cited

FOREIGN PATENT DOCUMENTS

| EP | 0362909 | 4/1990 |
|---|---|---|
| EP | 0448095 | 9/1991 |
| WO | WO9304697 | 3/1993 |

OTHER PUBLICATIONS

Ahlers et al., *J. Immunol.* 150(12):5647–5665, 1993.
Berzofsky et al., *J. Clin. Invest,* 88:876–884, 1991.
Bhardwaj et al., *Eur. J. Immunol.* 22:2009–2016, 1992.
Defoort et al., *Proc. Natl. Acad. Sci.* 89:3879–3883, 1992.
Del Val et al., *Cell* 66:1145–1153, 1991.
Eisenlohr et al., *J. Exp. Med.* 175:481–487, 1992.
Engelhard, *Ann. Rev. Immunol.* 12:181–207, 1994.
Greenstein et al., *J. Immunol.* 148:3970–3977, 1992.
Hansen et al., in fundamental Immunology, Paul, ed., Raven Press; New York, pp. 609 and 612, 1993.
Hart et al., *Proc. Natl. Acad. Sci.* 88:9448–9452, 1991.
Hart et al., *J. Immunol.* 145:2677–2685, 1990.
Javaherian et al., *Proceedings of the Natl. Acad. of Sciences of the USA* 86(17):6768–6772, 1989.
Lasarte et al., *Cellular Immunol.* 141:211–218, 1992.
Palker et al., *J. Immunol.* 142:3612–3619, 1989.
Partidos et al., *Immunol.* 77:262–266, 1992.
Rovinski et al., *J. Virol.* 66(7):4003–4012, 1992.
Sarobe et al., *Eur. J. Immunol.* 21:1553–1558, 1991.
Schrier et al., *J. Virol.* 62(8):2531–2536, 1988.
Strognin, in Laboratory Diagnosis of Viral Infections, Lennette, ed., Marcel Dekker, Inc., New York, pp. 211–219, 1992.

*Primary Examiner*—Jeffrey S. Parkin
(74) *Attorney, Agent, or Firm*—Towsend and Townsend and Crew LLP

(57) ABSTRACT

Peptide constructs comprised of multideterminant T helper peptides from the envelope glycoprotein of HIV previously identified to induce proliferative responses in four different haplotypes of mice and IL-2 responses in 52–73% of HIV positive, flu positive patients (cluster peptides), were co-linearly synthesized with the peptide 18 of the V3 loop of HIV-1 gp 160, corresponding to the principal neutralizing determinant of HIV-IIIB and also shown to contain a dominant CTL epitope. Cognate help for peptide 18 antibody was elicited following a single immunization in all strains of mice which had previously responded to a T cell epitope encompassed by the peptides. In two strains of mice, the level of neutralizing antibody achieved was comparable to levels adequate for protection from homologous viral challenge in chimpanzees. After a single boost, much higher antibody titers for 90% neutralization in the range of 1:1000 to 1:16,000 were achieved. Spleen cells from mice of three distinct MHC haplotypes sharing the $D^d$ class I MHC molecule but with different class II molecules, immunized with the compound peptides, exhibited enhanced gp160-specific CTL activity.

7 Claims, 23 Drawing Sheets

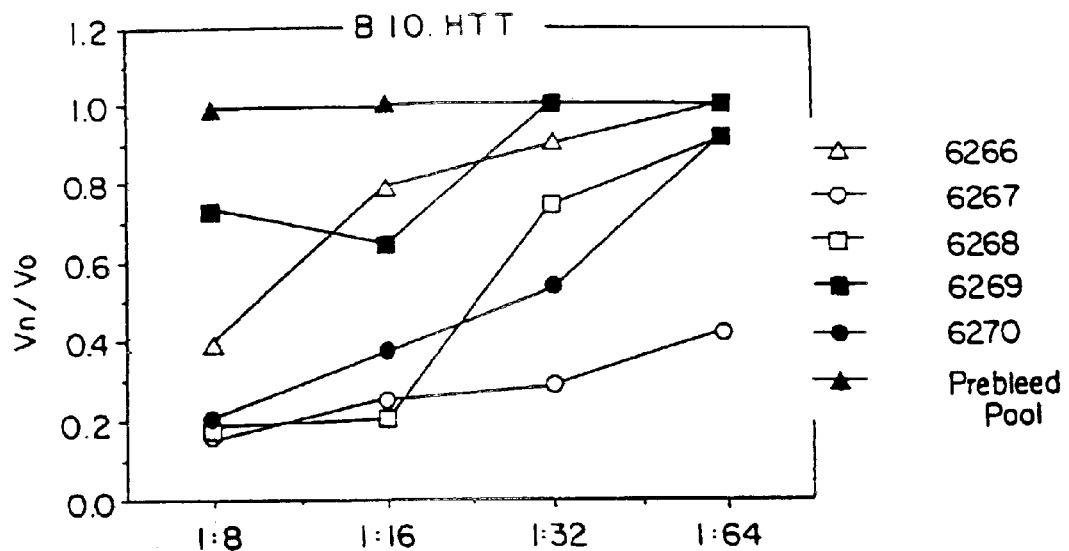
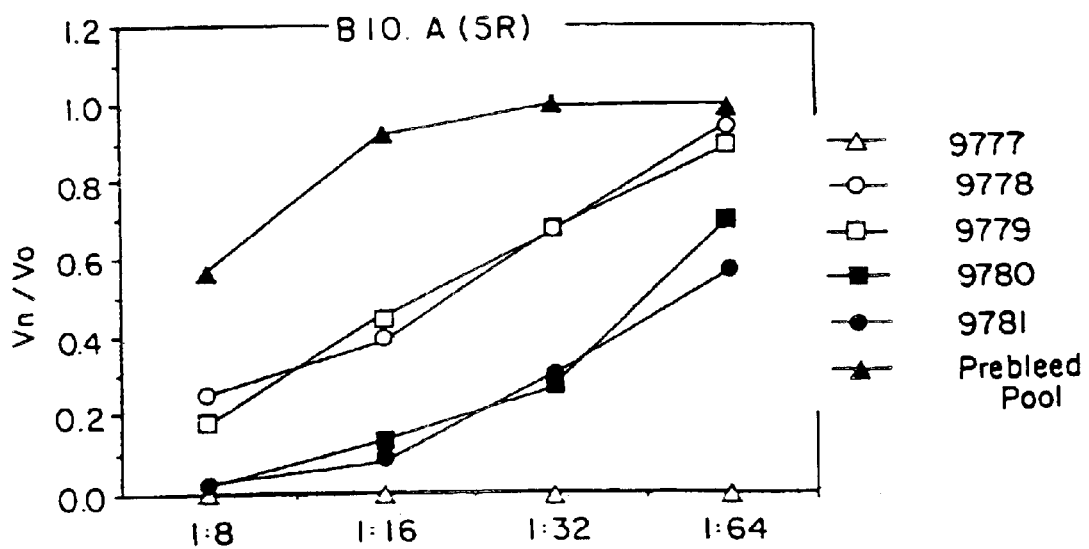

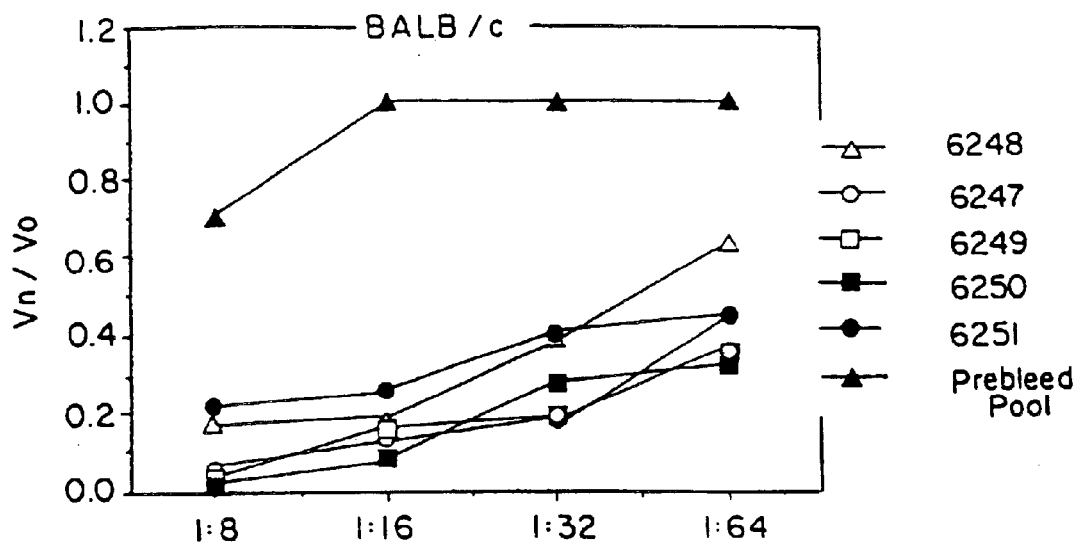
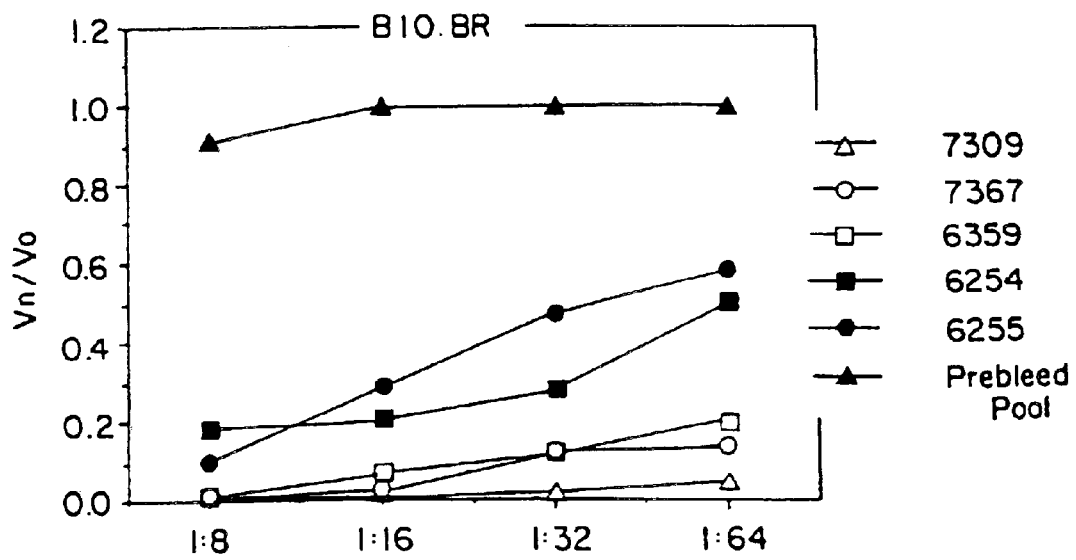

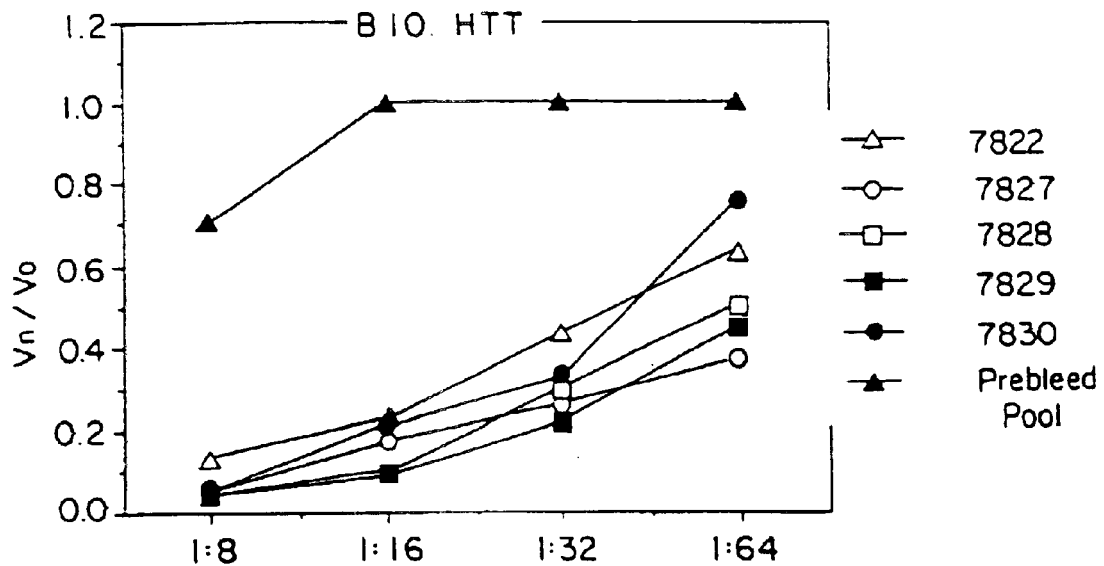
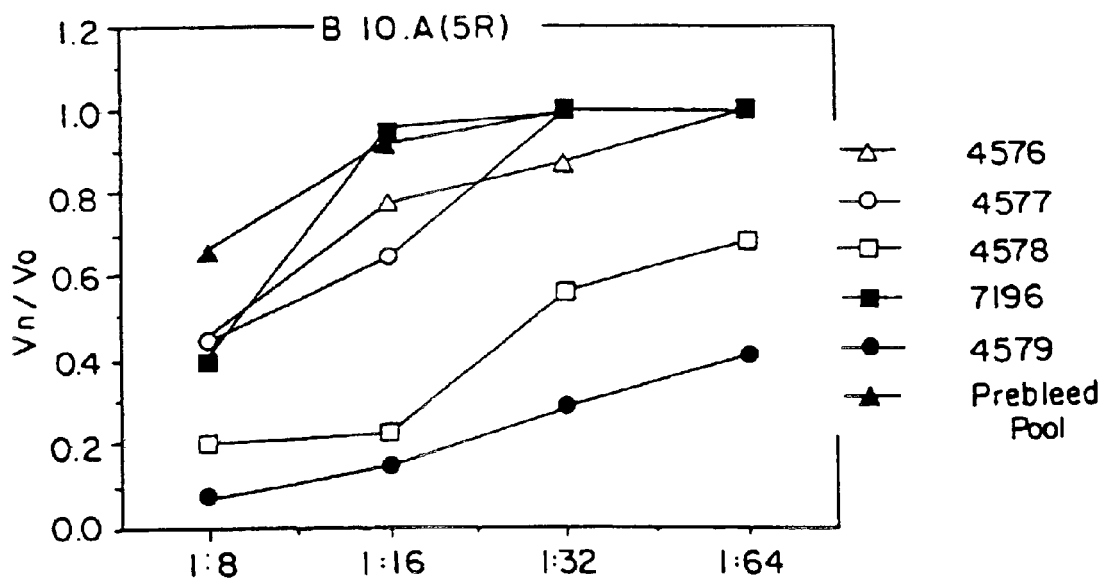

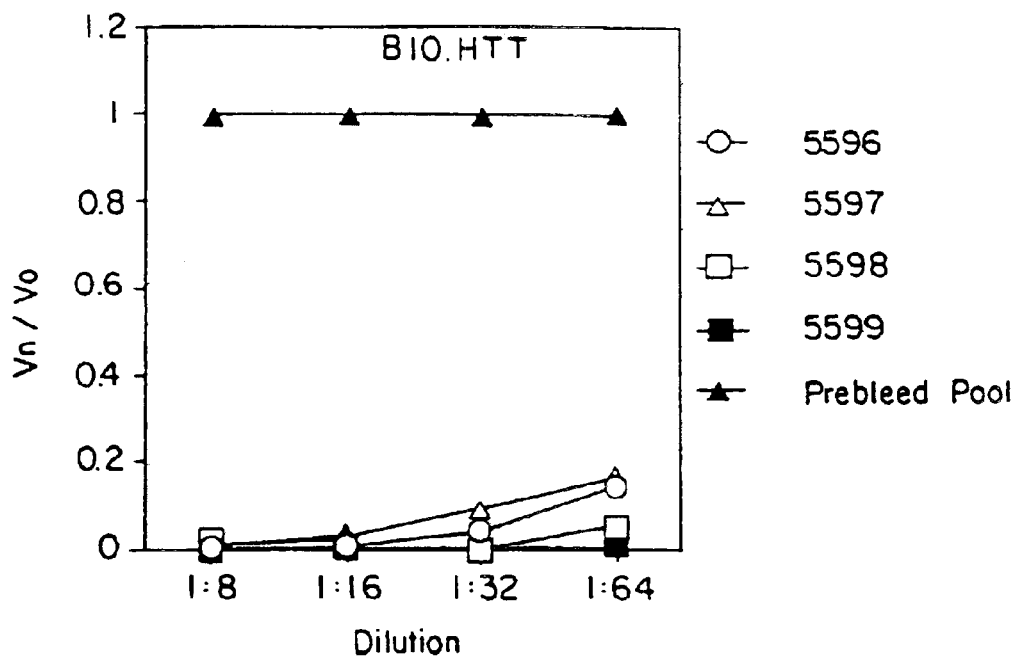
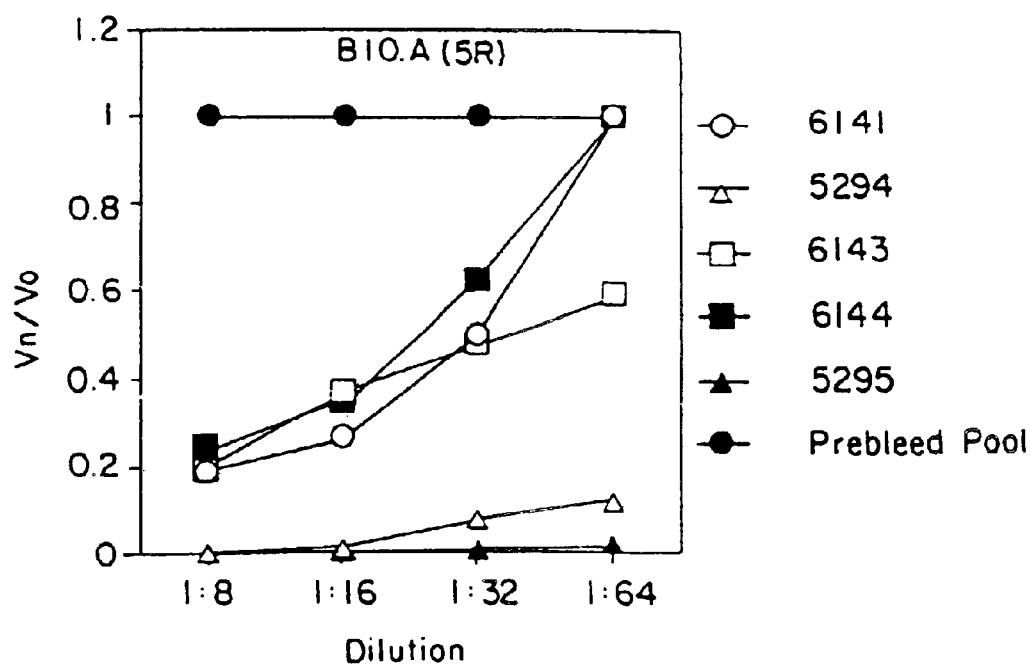

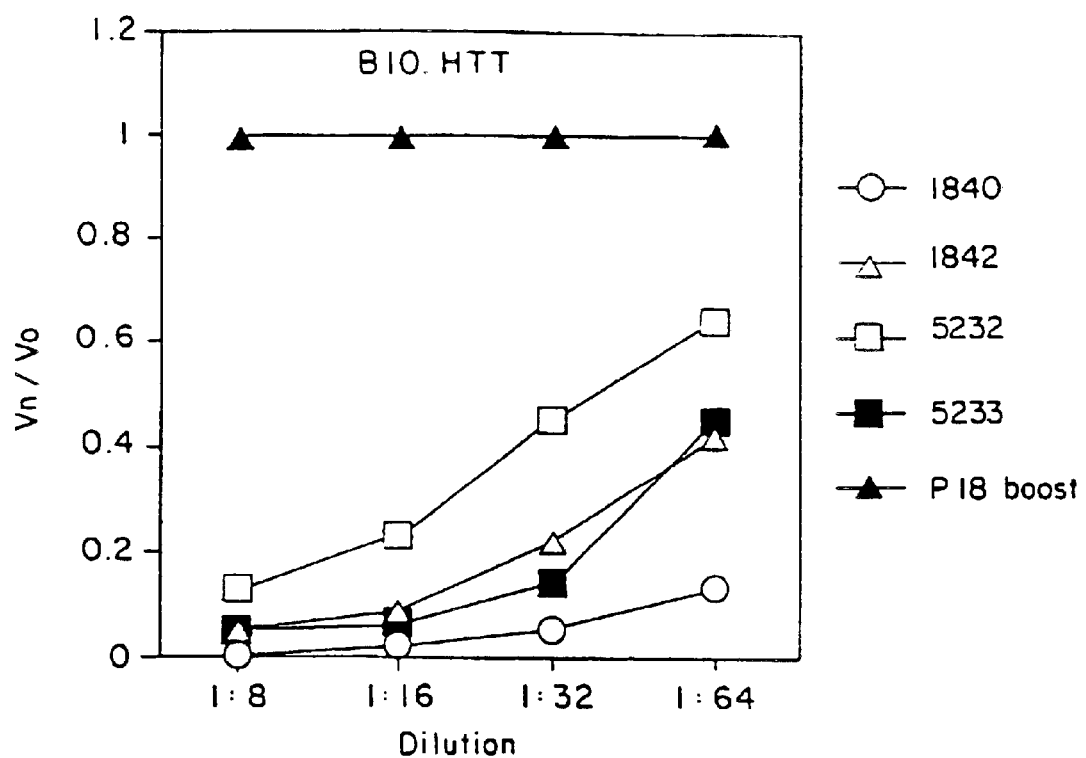
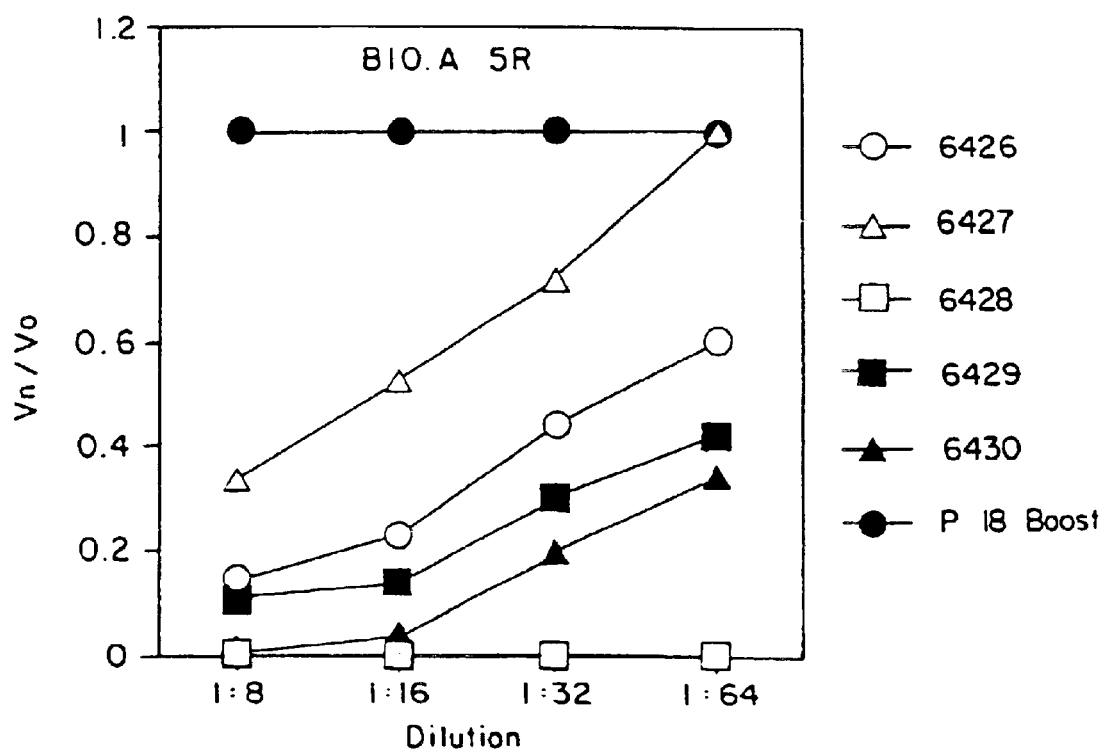

PEPTIDES WHICH ELICIT A HIGH NEUTRALIZING ANTIBODY TITER, CYTOTOXIC T LYMPHOCYTE RESPONSE AND T HELPER CELL RESPONSE IN A BROAD RANGE OF MHC TYPE RECIPIENTS

This application is a divisional of and claims the benefit of U.S. patent application Ser. No.08/060,988, filed May 14, 1993; which is a continuation-in-part of U.S. patent application Ser. No. 07/751,998, filed Aug. 29, 1991, now abandoned and a continuation-in-part of U.S. patent application Ser. No. 07/847,311, filed Mar. 6, 1992 now U.S. Pat. No. 5,976,541; which is a continuation-in-part of U.S. patent application Ser. No. 07/148,692, filed Jan. 26, 1988, now abandoned. Priority application Ser. No. 07/751,998 is also a continuation in part of U.S. patent application Ser. No. 07/148,692, filed on Jan. 26, 1988, now abandoned, and a continuation in part of U.S. patent application Ser. No. 07/492,318, filed on Feb. 28, 1990 (now U.S. Pat. No. 5,081,226), which is a continuation of U.S. patent application Ser. No. 07/014,430, filed on Feb. 12, 1987 now abandoned, which is a continuation in part of U.S. patent application Ser. No. 06/947,935, filed on Dec. 30, 1986 now abandoned. All of the above noted priority applications and patents are incorporated herein by reference in their entirety for all purposes.

BACKGROUND OF THE INVENTION

1. Field of the Invention

The invention relates to peptides which comprise covalently linked T helper (Th) epitopes, cytoxic T lymphocyte (CTL) epitopes and epitopes which elicit a neutralizing antibody response (AbN) to an infectious agent, especially a parasitic or viral pathogen. Specific examples focus on application of the invention against Human Immunodeficiency Virus (HIV). The peptides have the further characteristic of evoking all three of these responses in hosts having a broad range of Major Histocompatibility Complex (MHC) types.

The invention is also directed to diagnostic methods for immune function in individuals infected with HIV which utilize the above-described peptides and is further directed to prophylactic or therapeutic vaccines which use the above-described peptides as a component of, or perhaps, as the sole active ingredient in the vaccine composition.

2. Description of the Related Art

Immune responses to HIV antigens elicited during natural infection may be a balance between those regulating viral infection and those antagonistic to the integrity of immune function (1–3). The determinants which weigh favorably or unfavorably upon this balance are not certain. The initial immune responsiveness of the host seems to influence the course of persistent HIV infection leading to progressive debilitating disease associated with increasing immunologic dysfunction (4–7). The virus may contain structures enabling it to evade the immune system, such as suppressive epitopes or masking carbohydrates, structures inducing clonal restriction (8–10), or structures that elicit deleterious effects such as antibodies which enhance viral infectivity (11–16) or autoreactive antibodies or T cells that contribute to the immunodeficiency (17–20).

The principal neutralizing determinant (PND) of the HIV envelope is located in the third hypervariable region or V3 loop between cysteine residues 301 and 331 (21–23). Antibodies to this region were initially demonstrated to be type specific in their neutralizing properties and more cross-reactive when examined by peptide binding ELISA (23–26), although more broadly neutralizing antibodies to the V3 loop have also been observed (27). Fortunately for synthetic vaccine development, such antibodies can be raised by immunization with short peptides (21,28,29). The protective efficacy of V3-specific antibodies to homologous cell-free virus challenge has been shown in chimpanzee challenge studies (15,30,31) and most recently protection against viral challenge was achieved by passive transfer into chimpanzees of a mouse-human IgG1 chimeric monoclonal antibody specific for the V3 loop (32). Sequence variation in the viral envelope protein in and outside (but affecting) this region results in both neutralization escape mutants, potential CTL escape mutants, and altered cellular tropism (33–37).

A high degree of genetic variability in HIV isolates can be found in infected individuals (38–40). HIV isolates from a given individual appear to change ver the course of disease. Under immune pressure the virus appears to exhibit differences in phenotypic characteristics such as cytopathicity, replication rates, and cellular tropism during the course of infection. Evidence that the virus may be replicating continuously at low levels during infection and never achieve a state of "true latency" supports the view that HIV-1 produces a chronic active infection and selective mechanisms play an important role in viral persistence (33). Multiple distinct V3 regions encoding the PND of the envelope protein have been detected in isolates of HIV derived from peripheral blood mononuclear cells (PBMC), suggesting that positive selection leads to much diversity of HIV env genes in vivo (40). Nevertheless there is evidence that the PND contains conserved epitopes that are the targets of neutralizing antibodies generated by sequence divergent isolates and that a limited number of peptides from the PND can elicit neutralizing antibodies recognizing multiple isolates, albeit at lower titer, and probably lower affinity (24,25,41).

The criteria for an effective vaccine must be not only that it is safe, i.e., does not contain epitopes that elicit autoimmune or virus enhancing responses, but also that it is capable of eliciting both a cellular immune response and a neutralizing antibody response to all the potential HIV variants prevalent in the infected population. In addition, since the MHC molecule of a given individual will bind and recognize only a subset of potential antigenic determinants recognized by the species as a whole, a synthetic peptide vaccine must also incorporate enough antigenic determinants to elicit recognition by T cells of most HLA types.

Accordingly, in a previous study we constructed six synthetic peptides of 20–33 residues each that correspond to six multideterminant T helper regions of the HIV envelope (42). Called cluster peptides, these span clusters of distinct but overlapping T helper epitopes recognized by proliferating T cells of three or four haplotypes of mice. These cluster peptides were tested for their ability to stimulate T cell responses in mice immunized with recombinant gp 160 (rgp160) and in peripheral blood lymphocytes of humans infected with HIV. Mice were also immunized with the cluster peptides to test for the induction of T cells responding to intact gp160 in vitro. Cluster peptides 3, 4, and 6 (see sequences in Table I) stimulated T cells from mice of all four MHC haplotypes immunized with rgp160; and when mice were immunized with the cluster peptide, elicited T cell responses capable of recognizing the whole envelope protein in vitro. Cluster peptide 1, also used in this current study, stimulated proliferation strongly in only one strain of mice, despite the fact that the three other strains recognized components of the multideterminant region from which this peptide was made. Thus, the whole had less activity than the sum of its parts (42). Cluster peptides 1, 3, 4, and 6 stimulated significant IL-2 responses in peripheral blood lymphocytes of HIV-positive, influenza positive humans in 64, 73, 52, and 58% of tested cases respectively. It is of interest to note that these high responses were observed despite the fact that the subjects tested were presumably infected with a large number of different substrains of HIV. Cluster peptides 1, 3, and 4 have sequences relatively conserved among North American and European isolates of HIV, and cluster peptide 6 spans the boundary between conserved and variable sequences (43).

A successful peptide vaccine should be capable of eliciting T helper (Th) and cytotoxic T lymphocytes (CTL) responses as well as a neutralizing antibody response in vaccinees of multiple HLA types. Major histocompatibility complex (MHC) class I-restricted CTL appear to play a central role in the recovery from viral infection (81). Although exogenous lymphokines can substitute for T-cell help in the maturation of CTL precursors in vitro, the role of Th in priming CTL in vivo still remains poorly understood, compared to Th-B-cell collaboration. Although much evidence for a helper requirement in CTL induction exists (82–90), there is also evidence for CTL responses independent of help (85,91–95). Further, no study to date has shown a necessity for help requiring covalent linkage of a helper antigenic determiant to a CTL determinant, analogous to the linkage of carrier to hapten in cognate help for B cells. This lack of evidence may be due to the fact that the targets of CTL are whole cells, and immunization until recently required whole cells (or tissue grafts) or live viruses. The closest one could come to suggesting determinant linkage was to show that the helper determinant and CTL determinant had to be on the same skin graft to induce rejection (89), but this could not be explored further at the molecular level. Now that the possibility of peptide immunization for CTL induction has been demonstrated (96–100), it becomes feasible to address this question using peptides comprising both helper and CTL determinants. Although recent evidence indicated that a helper site is beneficial (90,101,102), it was not clear if the helper and CTL sites needed to be linked. Indeed, uncoupled helper and CTL epitope peptides were effective in two studies (90, 102) and not tested in the other (101), but in the former studies, the mixture of helper and CTL determinant peptides was administered in incomplete Freund's adjuvant emulsion, which sequesters the two peptides in the same microenvironment, or was given at high dose for multiple immunizations.

SUMMARY OF THE INVENTION

The present invention is directed to peptides which provide a broad immune response to an antigen expressed by a pathogen. The antigen is typically one derived from a viral or parasitic pathogen. Our strategy for peptide design was to link each cluster peptide to a short synthetic peptide (peptide 18), previously identified to be an immunodominant site recognized by CD8 cytotoxic T cells in association with class I molecules, and found within the V3 loop or principal neutralizing determinant region of the HIV-IIIB envelope protein.

Immunization of hosts having a broad range of MHC types, (the H-2 loci in mice, equivalent to the HLA loci of humans) with a peptide of our invention results in an immune response having both humoral and cellular components. On the humoral side, a high titer neutralizing antibody response is observed. With respect to the cellular immune response, both cytotoxic T lymphocytes and T helper cells are elicited.

Proper choice of the epitopes employed evokes such a response that is broadly specific for a number of strains of a pathogen. This is particularly important if there is a great divergence in antigen structure among strains of the target pathogen, for example, as is observed for HIV. One method for designing peptides so as to produce a broadly specific response to a number of strains of HIV is described in co-pending U.S. patent application Ser. No. 07/760,530, hereby incorporated in its entirety by reference.

Accordingly, it is one object of the present invention to provide peptides which evoke all of a T helper response, a cytotoxic T lymphocyte response and a high titer of neutralizing antibody in a plurality of hosts expressing a broad range of MHC types.

The peptides of the present invention are also useful in a diagnostic context. For instance the particular peptides disclosed in the examples can be used in a variety of assay formats to assess the immune function of the T helper cells, cytotoxic T lymphocytes and B cells (both B-cell precursors and mature plasma cells) in individuals infected with HIV. Thus, it is also an object of the present invention to provide diagnostic methods and immune function assays which employ the peptides described herein as reagents.

By virtue of the broad immune response which is elicited in a host immunized with the peptides of the present invention, it is a further object of the present invention to provide vaccines, of either or both of a prophylactic and therapeutic nature, against a parasitic or viral infection, and against HIV-1 infection especially.

It is yet a further object of the present invention to provide a method of immunization of a mammalian host which elicits a broad immune response against a parasitic or viral pathogen, especially the HIV-1 virus.

The peptides of the present invention are comprised of a covalent linkage of a peptide having a multideterainant T helper epitope, such as described in U.S. patent application Ser. No. 751,998, a peptide having a cytotoxic T lymphocyte (CTL) epitope, preferably one which elicits CTL that are cross-reactive with a variety of strains of the target virus, such as described in U.S. patent application Ser. No. 07/847,311 or U.S. patent application Ser. No. 07/148,692 and a peptide having a determinant which elicits a neutralizing antibody (a principal neutralizing determinant (PND)). The epitopes in each case are those which can be shown to be recognized by hosts having a broad range of major histocompatibility complex antigens (MHC). The MHC are also called HLA in humans and are the cell surface proteins which determine, in part, whether or not tissue transplants are accepted or rejected by the host. The MHC proteins are involved in presentation of antigens to the immune system in early stages of an immune response. By virtue of the fact that the peptides of the present invention are recognized by a number of different MHC or HLA types, they are expected to be efficacious in a large portion of the host population.

The peptides of the present invention further demonstrate the property of eliciting a high titer of neutralizing antibody against the antigen from which their sequences are derived.

The methods for assessing the immune function of an individual having a viral infection that employ the peptides of the present invention are in vitro tests which measure the response of is lated cells from an individual to incubation of the cells with the peptide. For instance, Th activity can be assessed by measurement of cytokines released specifically in response to incubation of peripheral blood cells from a patient with a peptide of the present invention. A preferred cytokine to be measured is interleukin-2 (IL-2). The method of measurement can be any of the techniques known to the art, for instance, measuring proliferation of an interleukin-2 dependent cell line in supernatants of cultures of the incubated peripheral blood cells. Alternatively, ELISA assay of the IL-2 (or other cytokine) can be performed (see U.S. Ser. No. 07/751,998, hereby incorporated by reference). The methods for immunization with the peptide of the present invention can be quite simple, such as intravenous injection of a sterile composition comprised of one or more of the peptides of the present invention and a pharmaceutically acceptable carrier solution or adjuvant. Alternatively, the peptides can be administered bound to the surface of irradiated antigen-presenting cells, as is described in co-pending U.S. patent application Ser. No. 08/031,494 (hereby incorporated in its entirety by reference).

BRIEF DESCRIPTION OF THE DRAWINGS

FIGS. 2A–H HIV-1 IIIB neutralization profiles of four strains of mice 31 days following a single immunization with peptide PCLUS 6-18.

FIGSS. 5A, 5B. Fine specificity of neutralizing vs. nonneutralizing sera in PCLUS 3-18 and PCLUS 6-18 immunized mice. Neutralizing sera (solid bars) and nonneutralizing sera (open bars) were tested in an ELISA assay on wells coated with P18 substituted peptides. Fifteen peptides with single amino acid substitutions from the HIV-1 IIIB sequence (RIQRGPGRAFVTIGK; SEQ ID NO:7) toward the HIV-1 RF sequence (**TKGPGRVIYATGQ; SEQ ID NO:8) where used to coat wells (See Table V; SEQ ID NOs:7–23). Where the two sequences were identical, an Ala was substituted. Peptides were called 18-1 through 18-15, where the second number indicates the position in the sequence that was substituted. The letter under the number in each group indicates the amino acid from the RF sequence (or Ala) that was substituted at that position in the corresponding P18 IIIB sequence. An asterisk denotes a deletion. Sera are compared at a dilution of 1:1000.

Figure 6A:
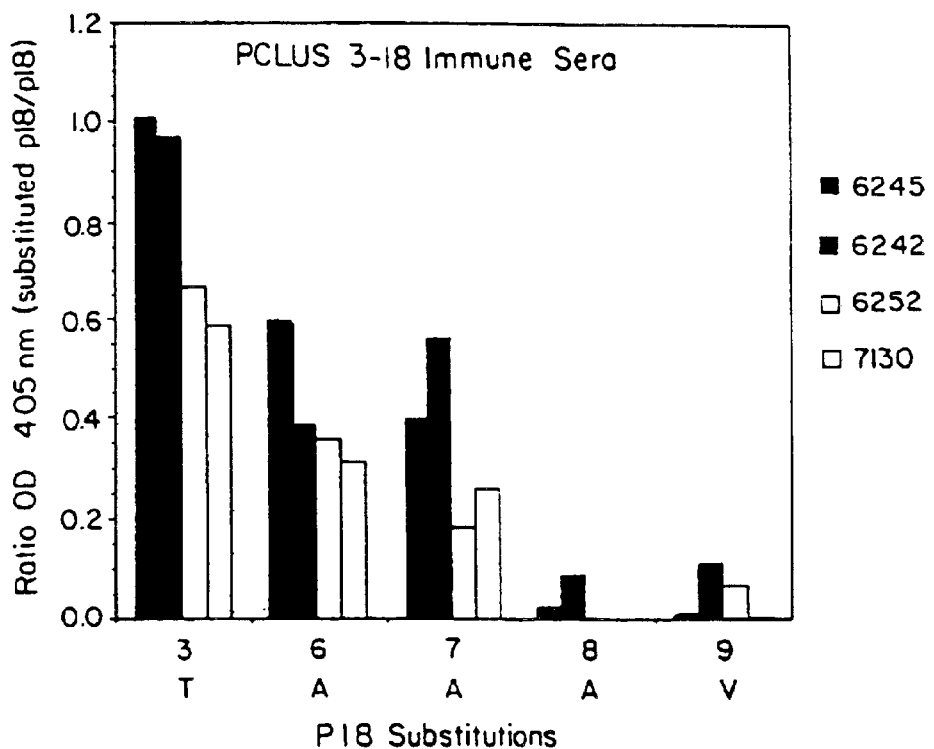
Figure 6B:
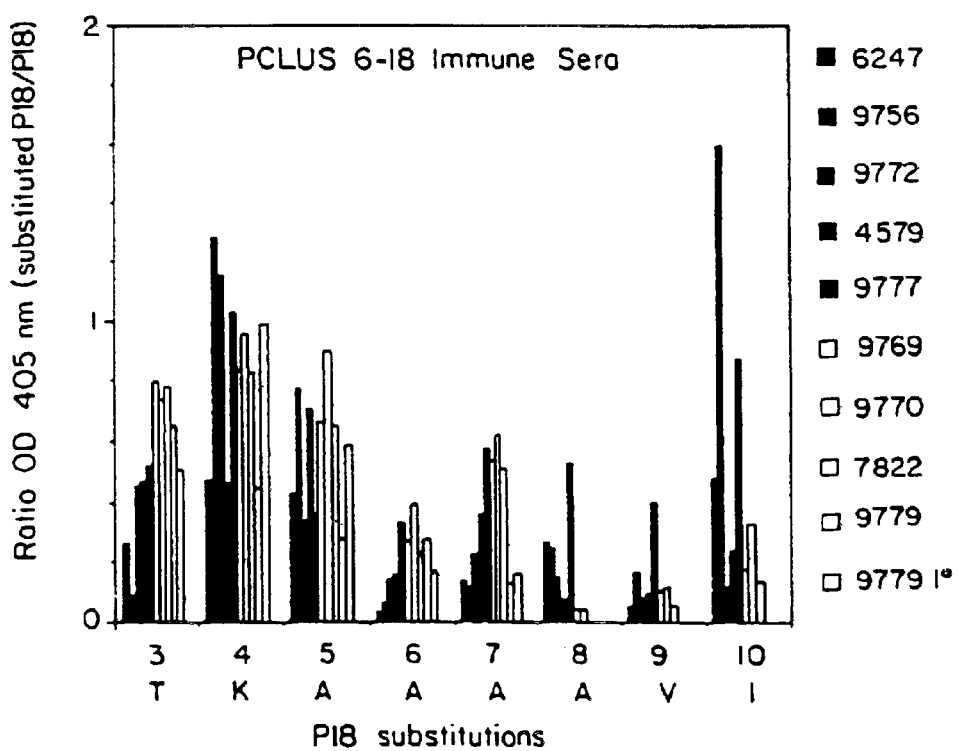

FIGS. 6A, 6B Binding to P18 variants substituted within the central V3 loop region. Peptide 18 variants substituted at positions 3–10 (as shown in Table V) were used to coat microtiter wells, and sera were tested for binding in an ELISA assay. The letter under the number in each graph indicates the amino acid from the RF sequence (or Ala) that was substituted at that position in the corresponding P18 IIIB sequence. Solid bars represent neutralizing sera and open bars represent nonneutralizing sera. Columns represent the mean absorbance ratio of binding to substituted peptide versus P18 at 405 nm of duplicate readings for individual sera, identified by number, from animals immunized with PCLUS 3-18 (A, upper panel) or PCLUS 6-18 (B, lower panel).

Figure 7A:
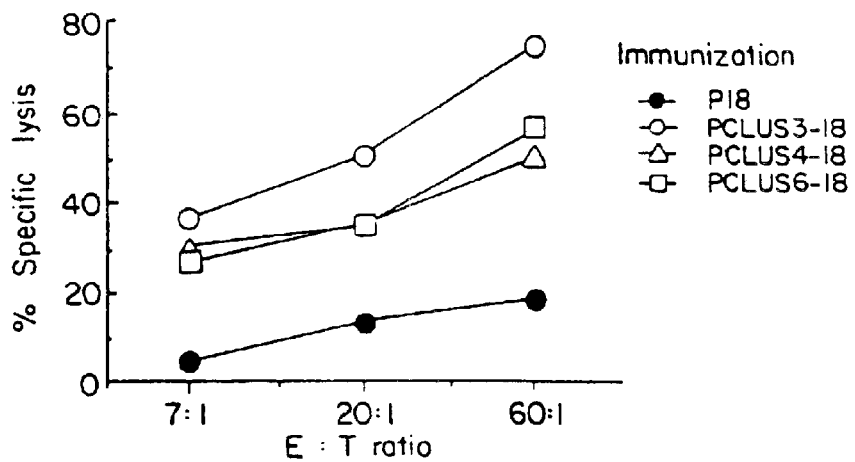
Figure 7B:
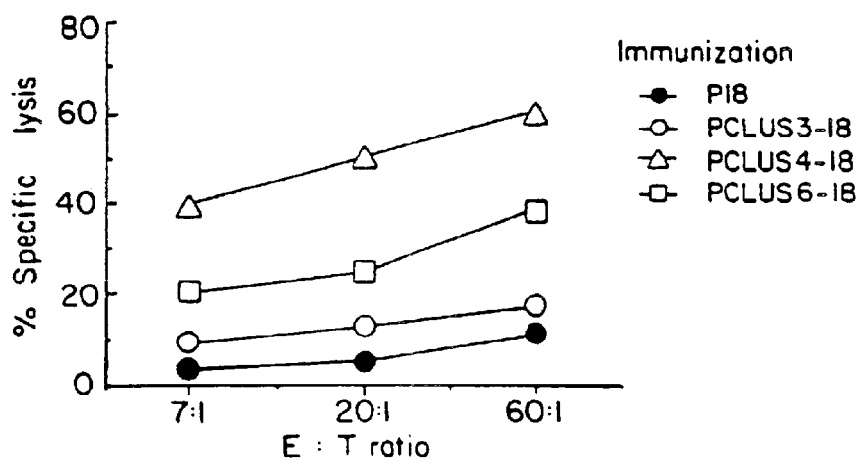
Figure 7C:
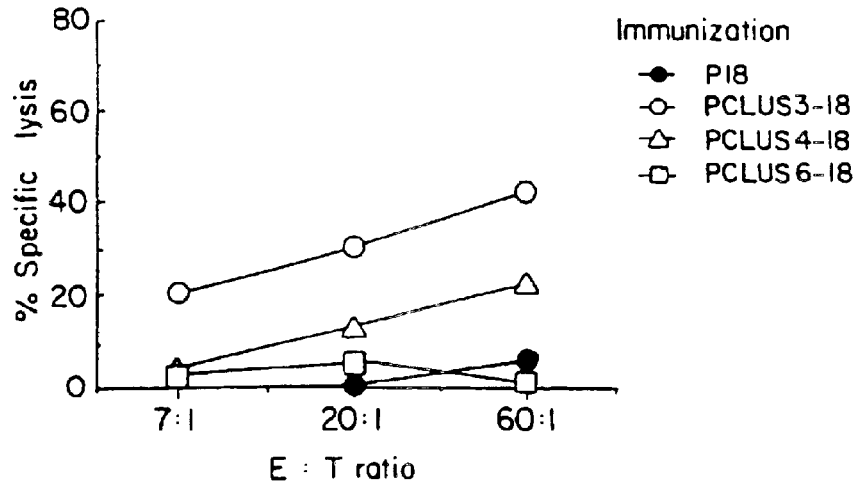

FIGS. 7A–C. Induction of HIV-1 envelope gp160-specific CTL activity by immunization with compound peptides in QS21 adjuvant. Because the standard error of the mean (SEM) of triplicate wells was consistently less than 8% of the mean, error bars are omitted for clarity.

Figure 8A:
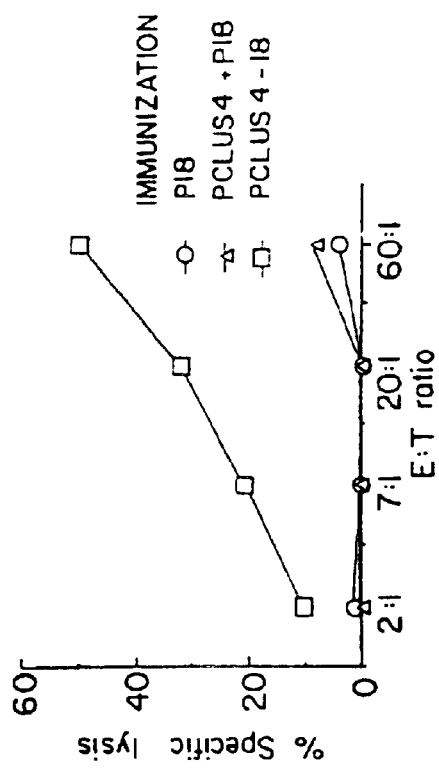
Figure 8B:
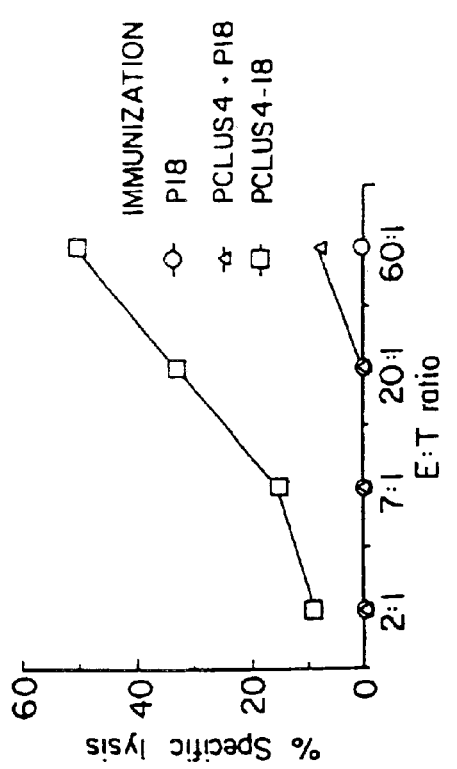
Figure 8C:
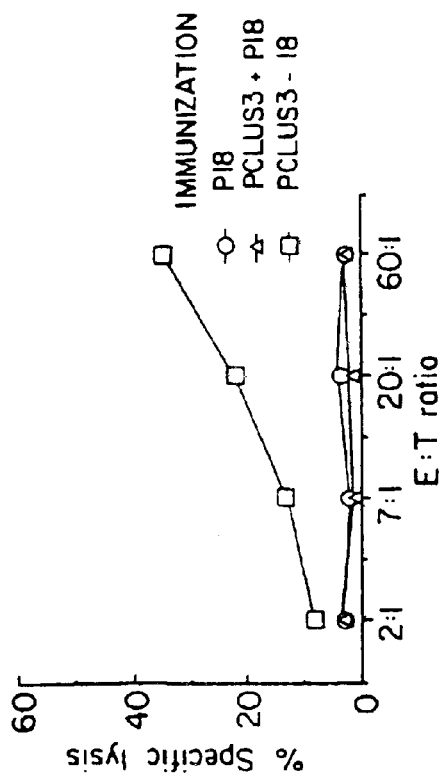
Figure 8D:
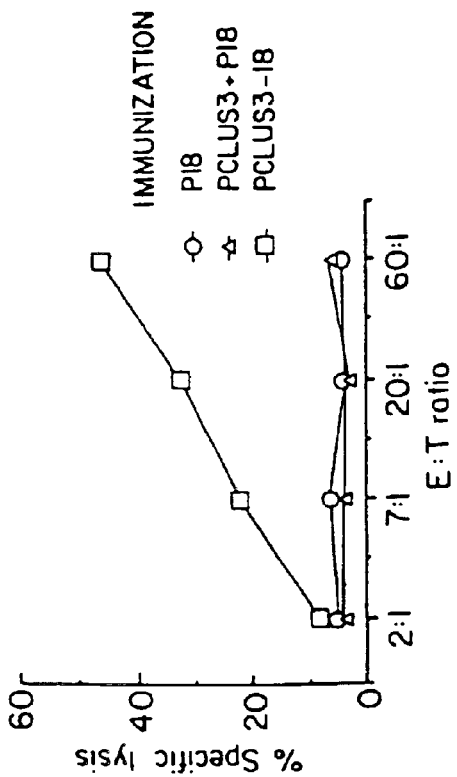

FIGS. 8A–8D. The requirement for linkage between helper and CTL determinants for priming of CTL. B10.D2 (FIG. 8A) and (FIG. 8C) or B10.A(5R) (FIG. 8B) and (FIG. 8D).

Figure 9A:
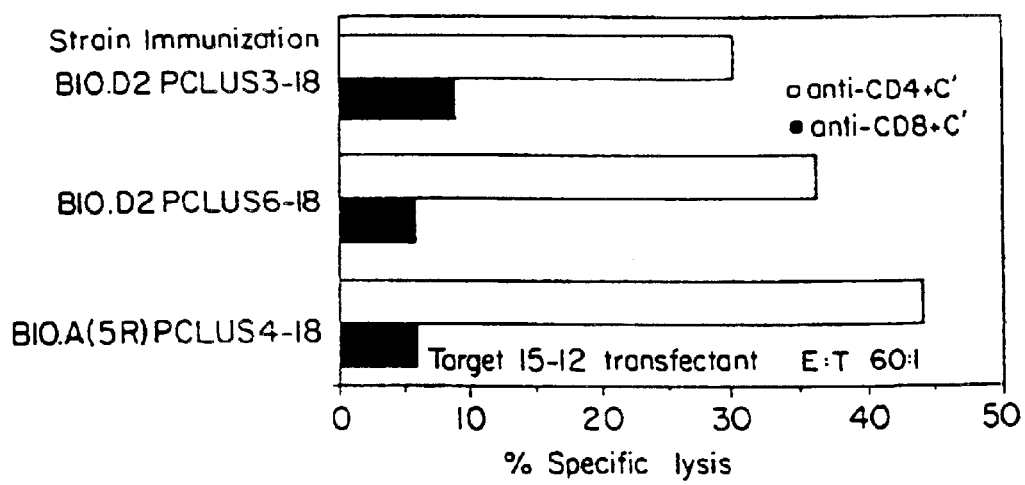
Figure 9B:
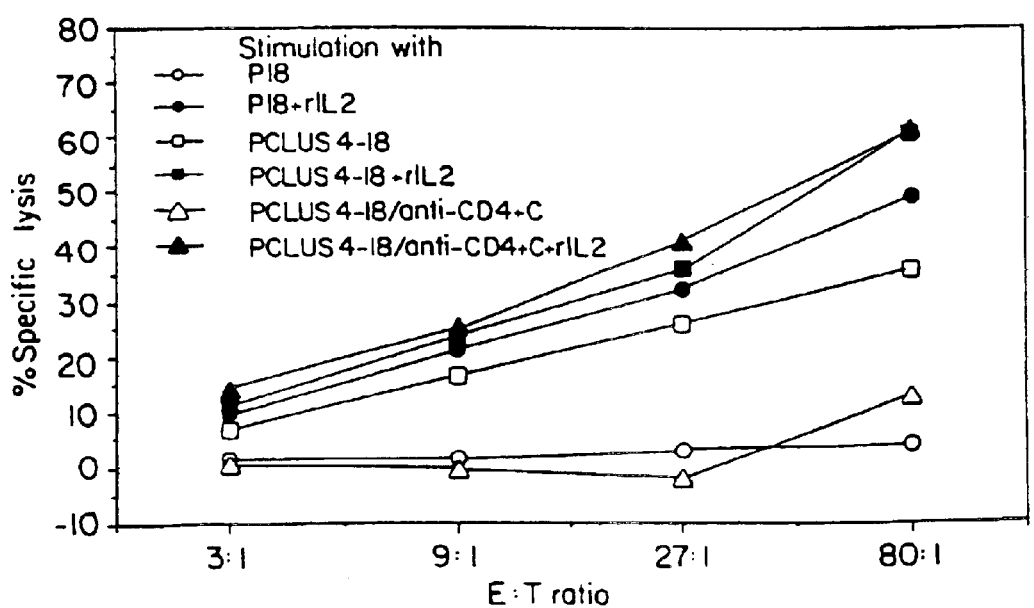
Figure 10A:
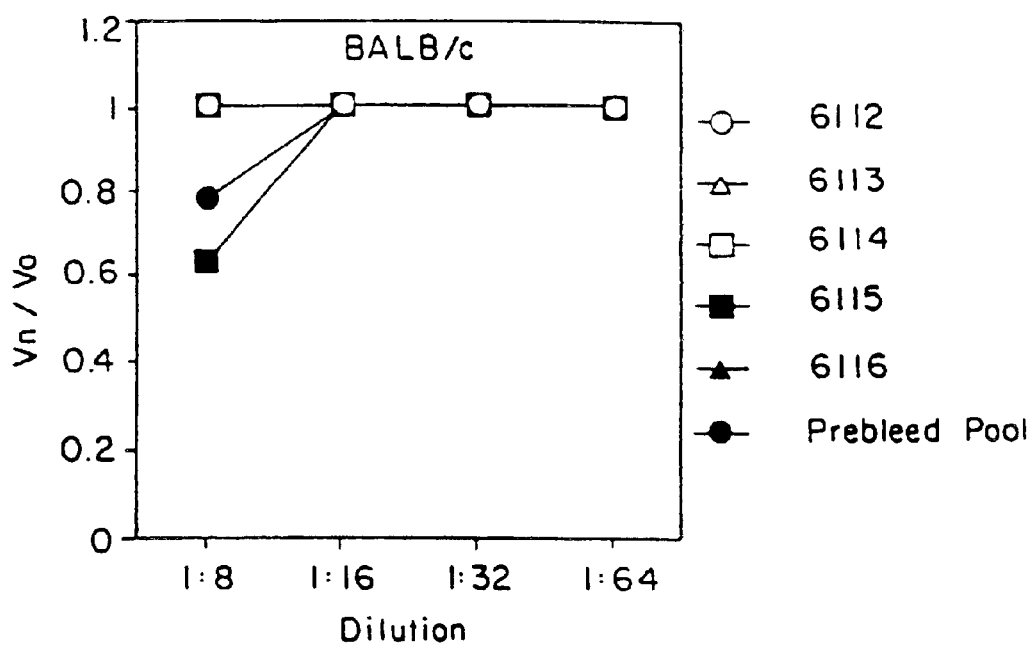
Figure 10B:
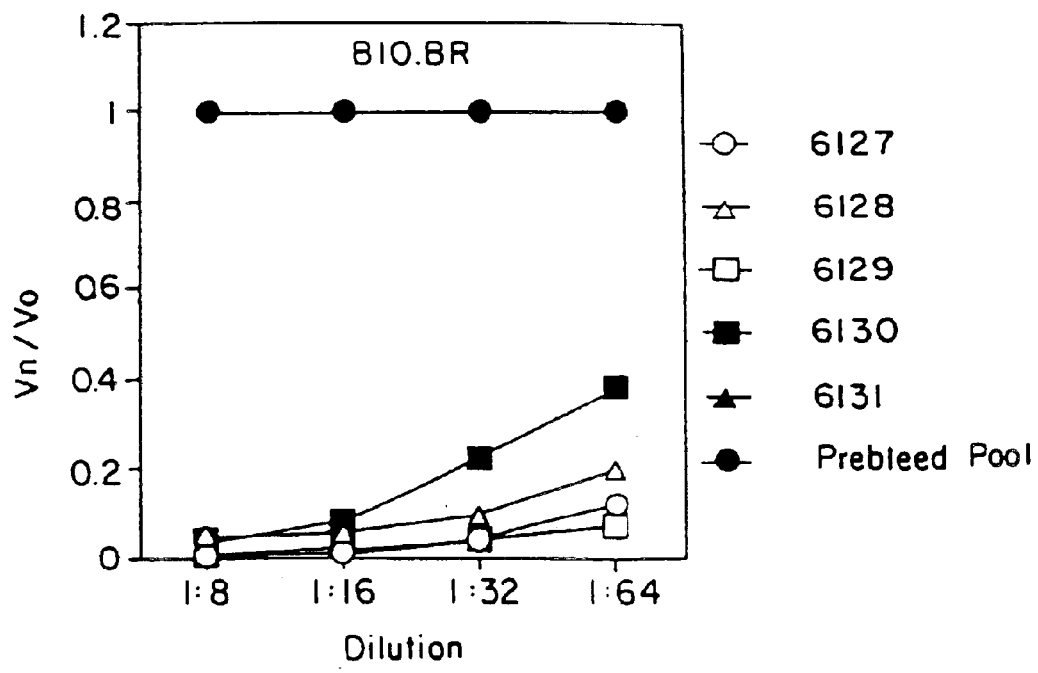
Figure 10E:
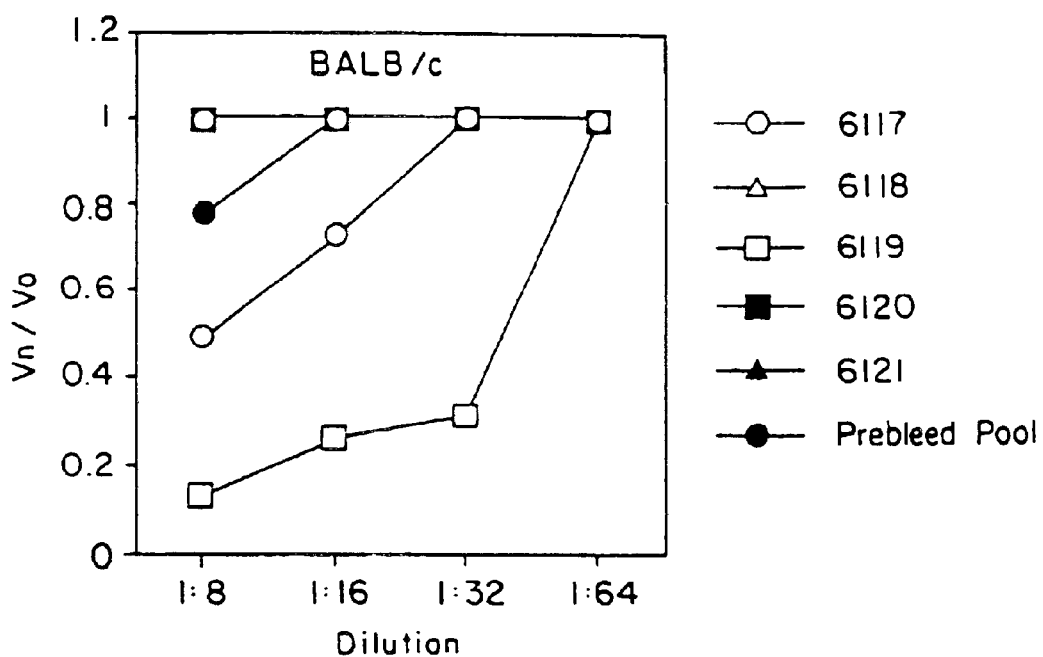
Figure 10F:
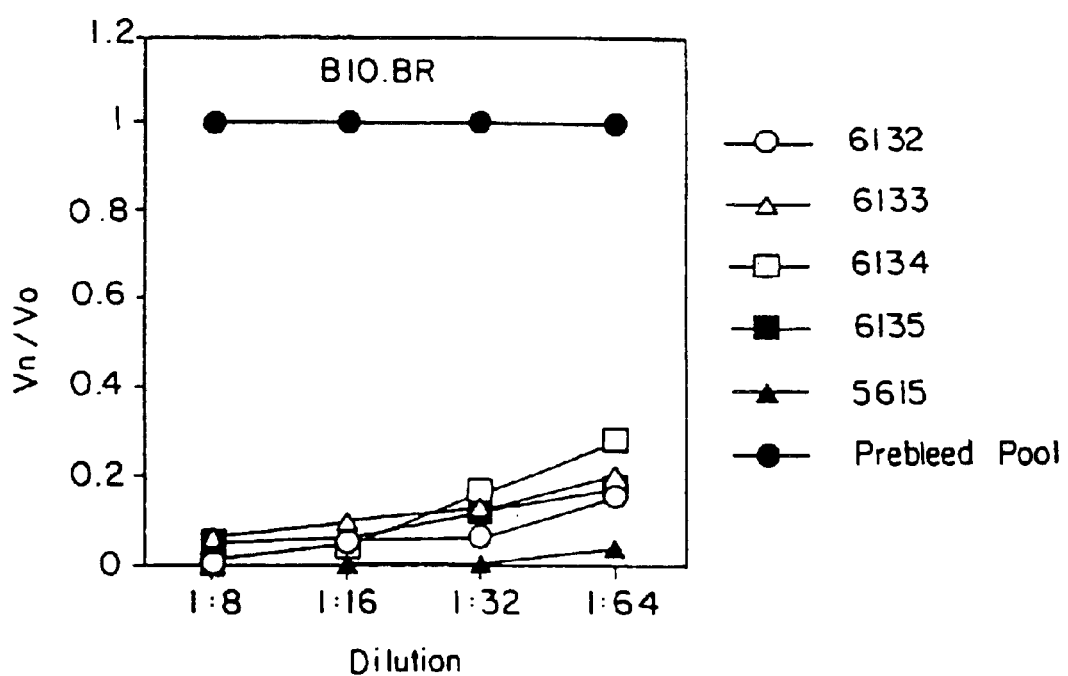
Figure 10G:
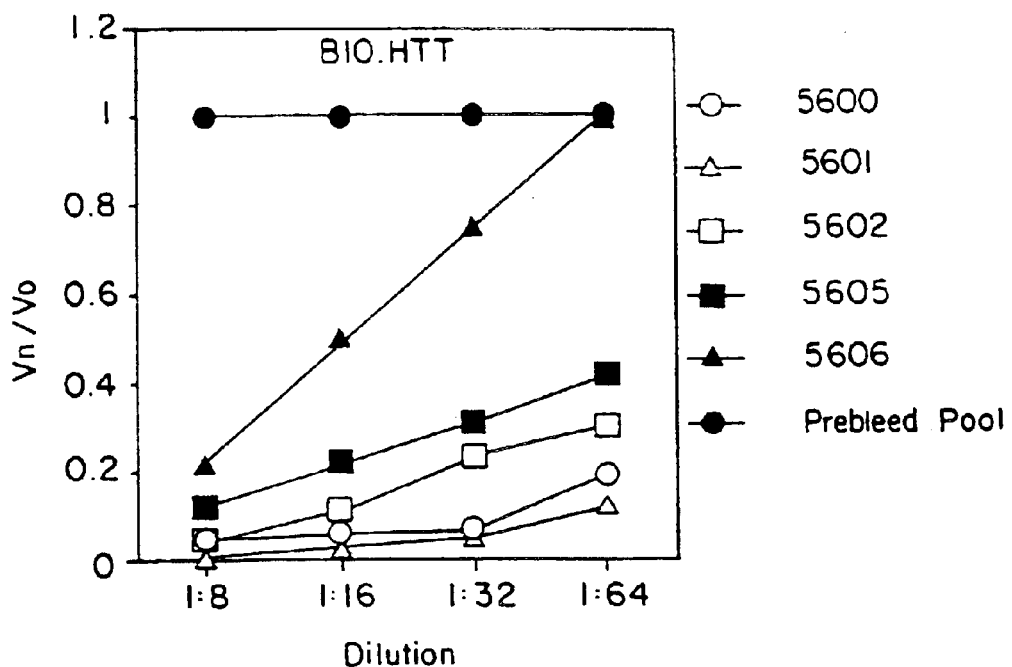
Figure 10H:
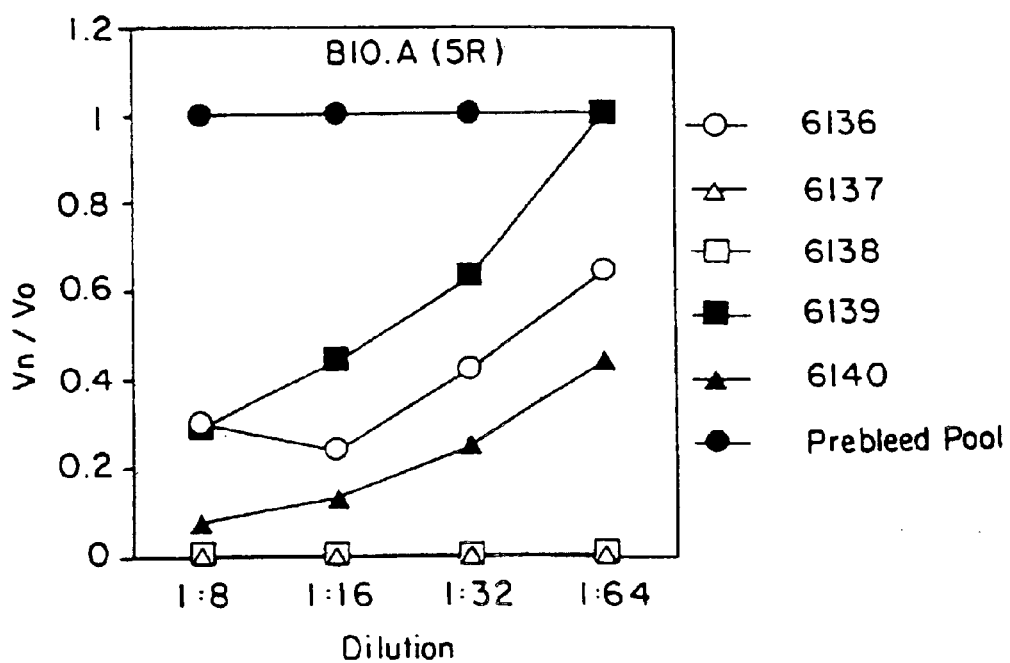
Figure 11A:
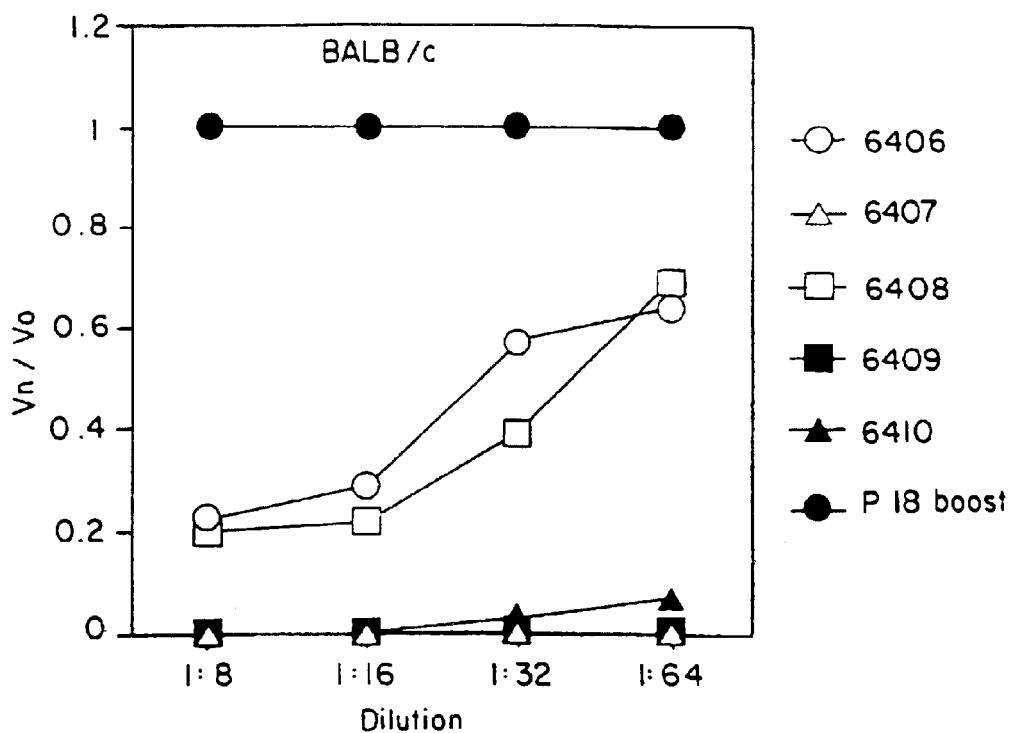
Figure 11B:
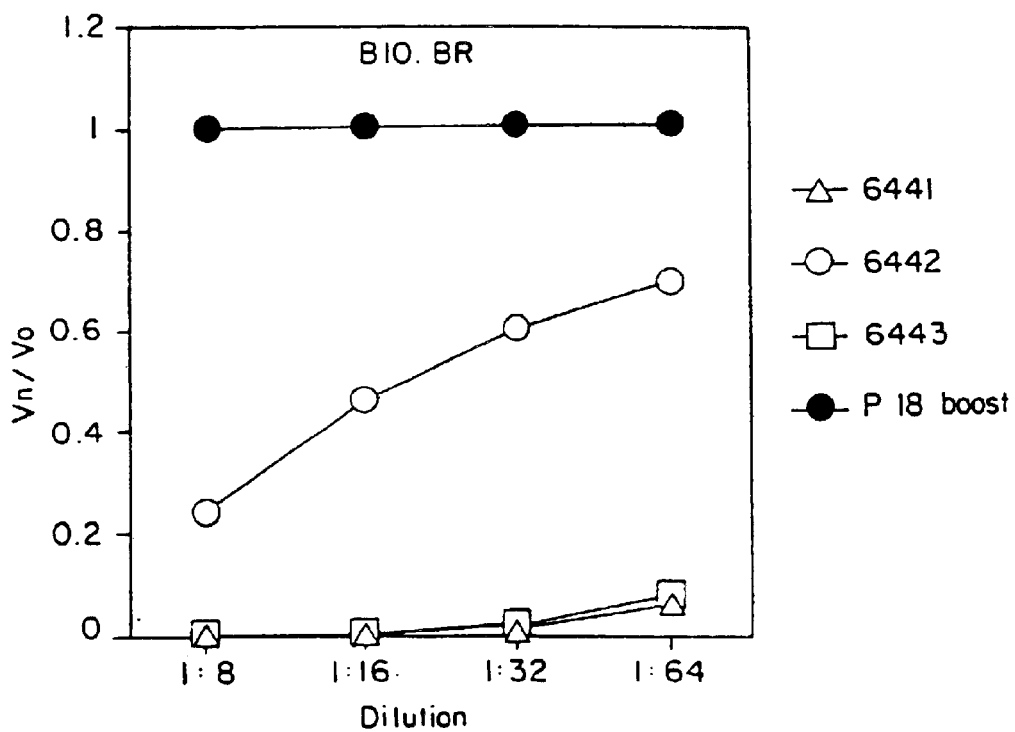
Figure 11E:
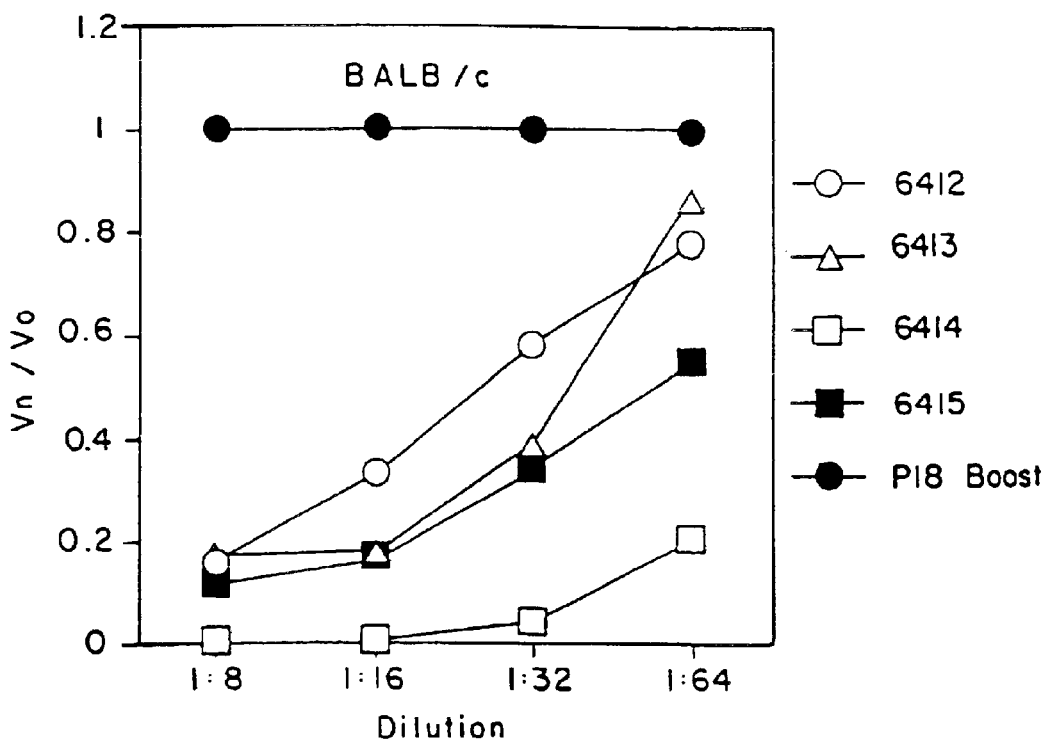
Figure 11F:
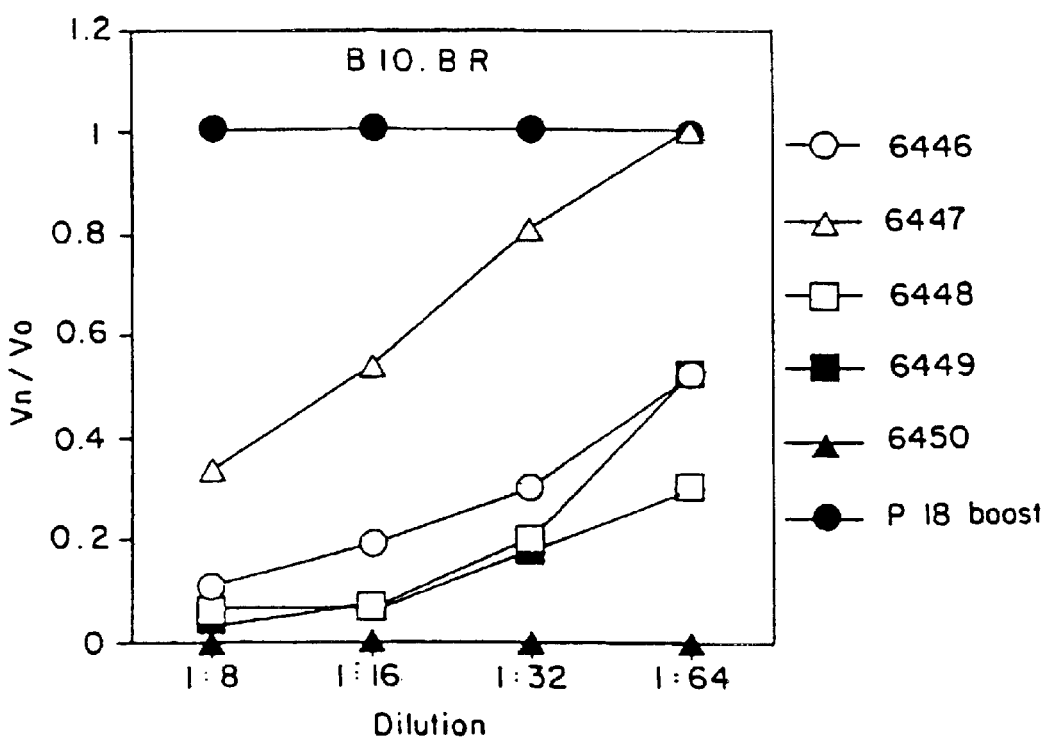
Figure 11G:
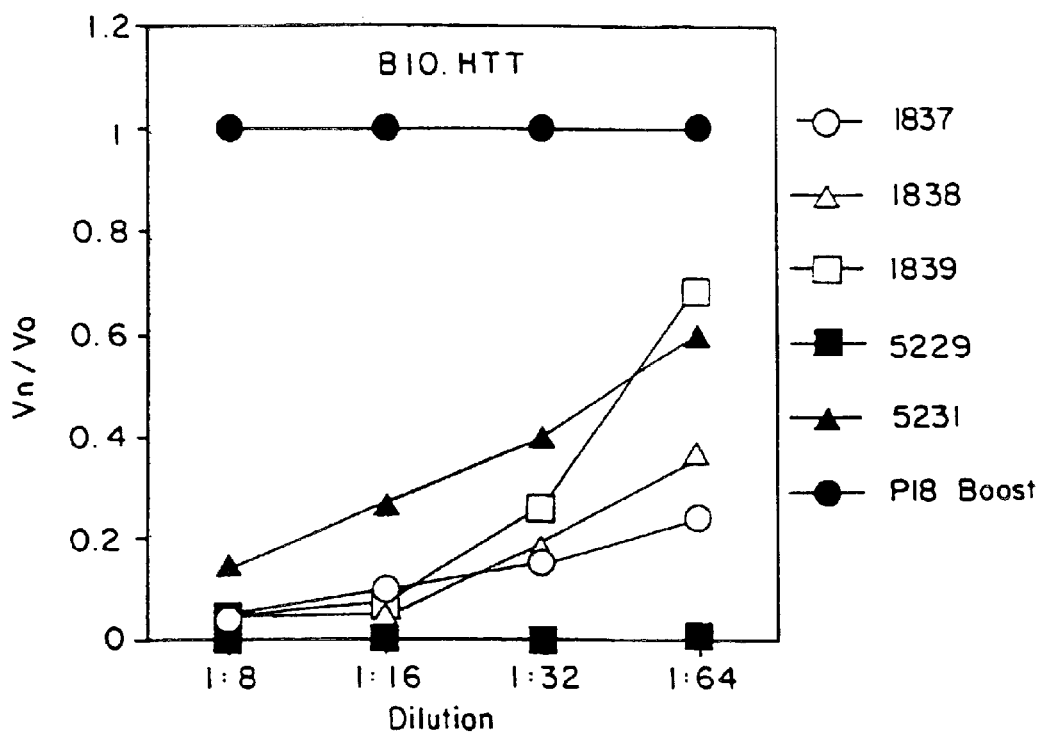
Figure 11H:
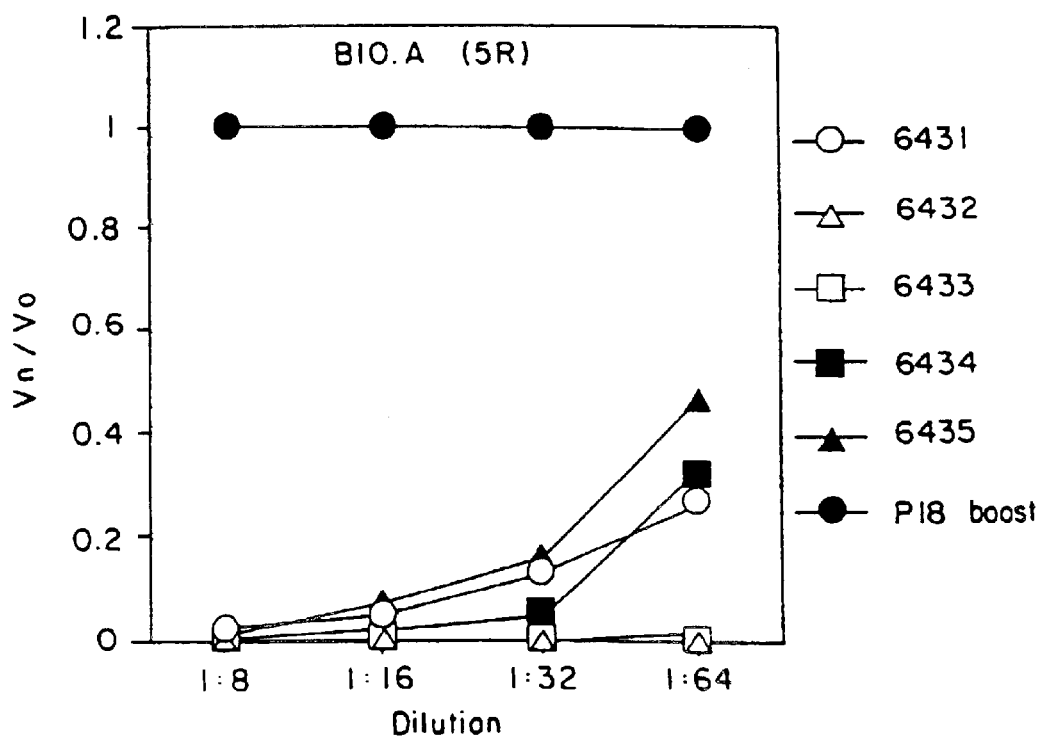

FIGS. 9A, 9B Phenotype of the CTL effectors (A), and the helper T cells (B) induced by immunization with the compound peptide constructs.

FIGS. 10A–H shows HIV neutralizing activity of PCLUS3-18MN boosted sera and PCLUS6-18MN boosted sera.

FIGS. 11A–H shows HIV neutralizing activity of PCLUS6-18MN boosted sera and PCLUS6.1-18MN boosted sera.

Figure 12A:
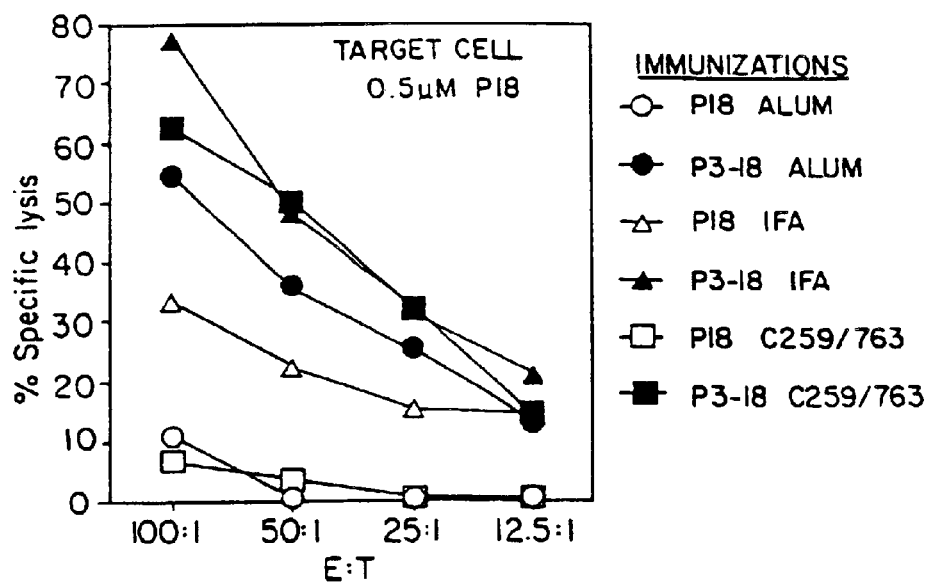
Figure 12B:
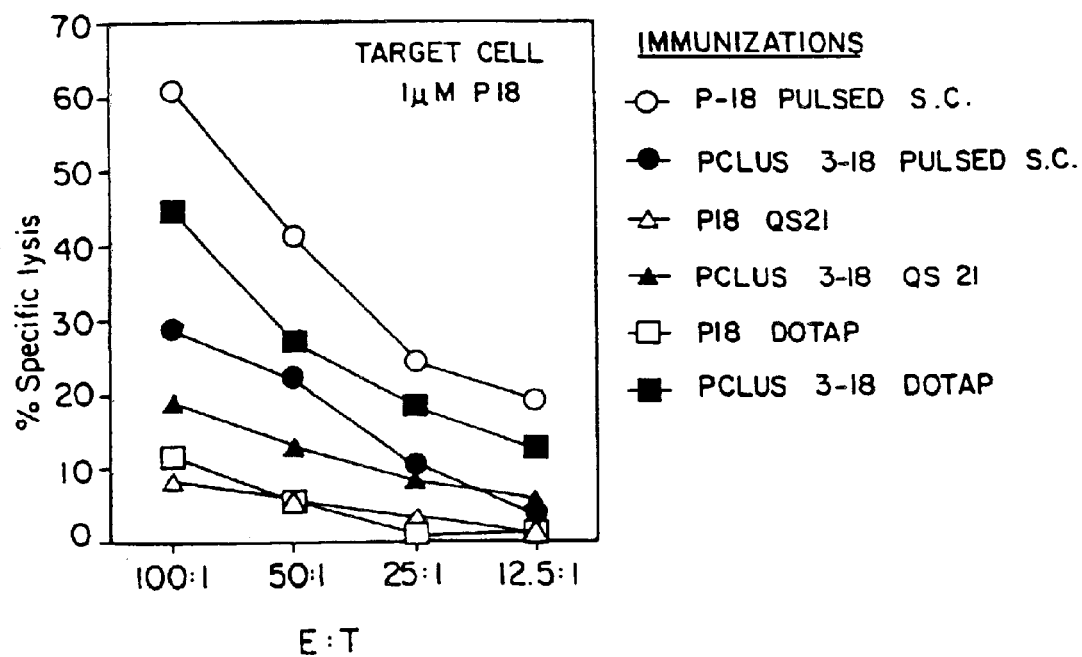

FIGS. 12A, 12B show CTL response elicited by immunization with P18-MN or PCLUS3-18MN in a variety of adjuvants.

Figure 13A:
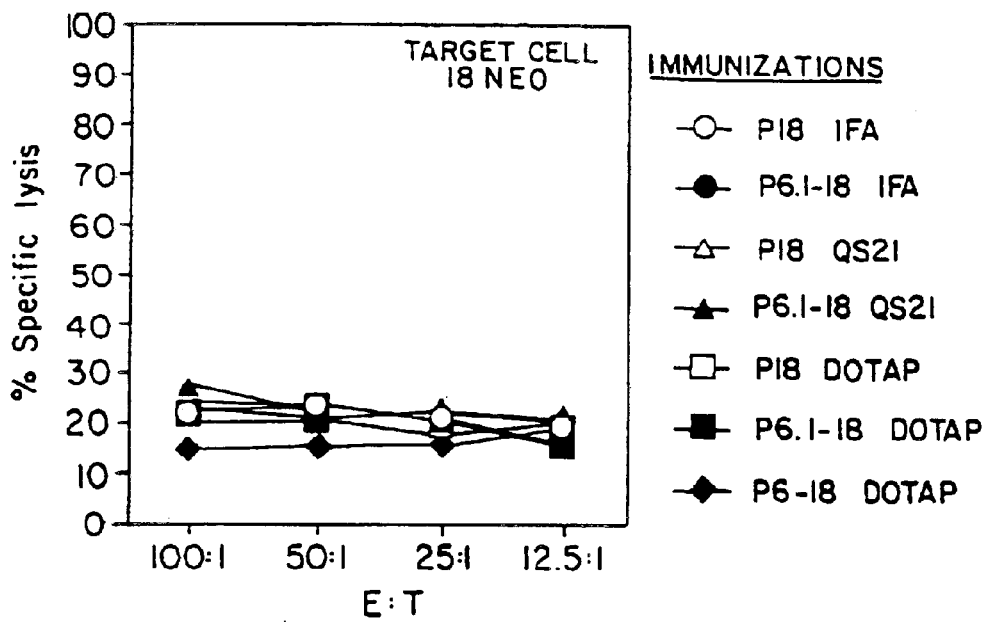
Figure 13B:
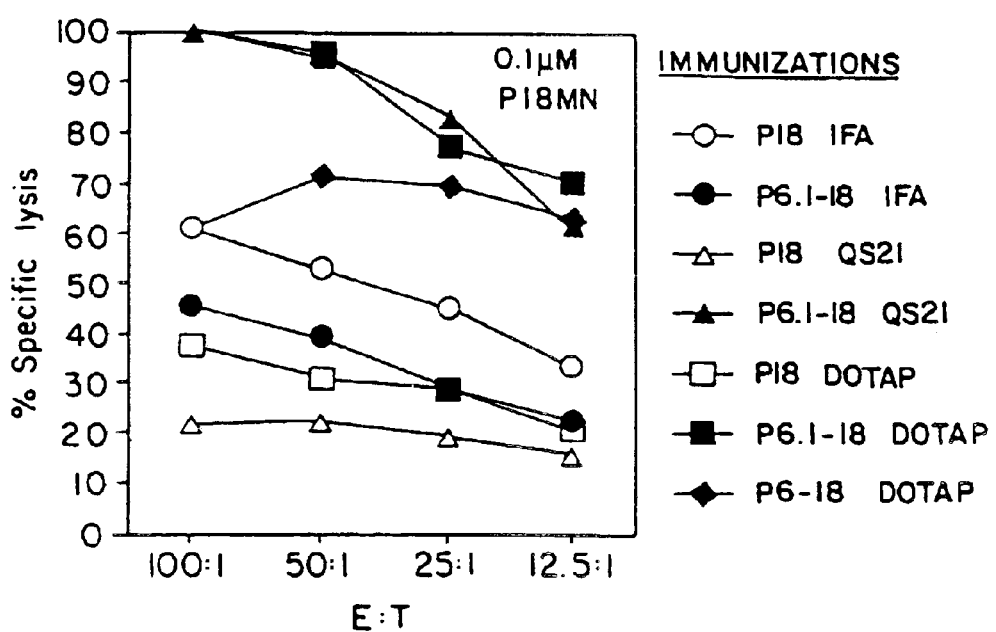

FIGS. 13A, 13B show CTL response following two immunizations of peptide in a variety of adjuvants.

DETAILED DESCRIPTION OF THE INVENTION

In an effort to provide help for an enhanced neutralizing antibody response, we have directly linked cluster peptides to peptide 18 (P18), which is contained within the PND. P18 consists of amino acid residues 308–322 of HIV-1 IIIB gp160 (sequence numbering according to the Los Alamos database (43), which is 7 less than the numbering of Ratner et al. (44) that we used previously (42)). P18 also contains an immunodominant cytotoxic T cell site (45,46). It is to be understood that the region of gp160 envelope protein homologous to the P18 region, from other strains of HIV than IIIB, can be employed in a similar manner. For instance, Example III shows results obtained when the P18 region of strain MN is used as the CTL epitope in the immunogen peptide. The peptides which are representative of the P18 region from various strains of HIV are disclosed in co-pending U.S. patent application Ser No. 07/847,311.

For example, P18 from isolate RF has the amino acid sequence SITKGPGRVIYATGQ(SEQ ID NO:37); P18 from isolate SC has the amino acid sequence SIHIGPGRAFYATGD (SEQ ID NO:38); P18 from isolate WMJ-2 has the amino acid sequence SLSIGPGRAFRTREI (SEQ ID NO:39); P18 from isolate Z321 has the amino acid sequence SISIGPGRAFFATTD (SEQ ID NO:40); P18 from isolate SF2 has the amino acid sequence SIYIGPGRAFHTTGR (SEQ ID NO:41); P18 from isolate NYS has the amino acid sequence GIAIGPGRTLYAREK (SEQ ID NO:42); P18 from isolate CDC4 has the amino acid sequence RVTLGPGRVWYTTGE (SEQ ID NO:43); P18 from isolate Z3 has the amino acid sequence SIRIGPGKVFTAKGG (SEQ ID NO:44); P18 from isolate MAL has the amino acid sequence GIHFGPGQALYTTGI (SEQ ID NO:45); P18 from isolate ZE has the amino acid sequence STPIGLGQALYTTRG (SEQ ID NO:46); P18 from the isolate JY1 has the amino acid sequence STPIGLGQALYTTRI (SEQ ID NO:47); and P18 from the isolate ELI has the amino acid sequence RTPTGLGQSLYTTRS (SEQ ID NO: 48).

The immunogenicity of haptenic peptides has been shown to be increased by linear polymerization or coupling to T helper determinants (47–49). The cluster peptides should provide help in multiple MHC haplotypes. Remarkably high neutralizing titers were obtained in mice of several MHC types after just a single boost with some of these peptides. We further attempted to examine the fine specificity and affinity of neutralizing antibody directed against peptide 18. This approach can be used in designing peptides for a synthetic peptide vaccine for the immunoprophalaxis and immunotherapy of HIV infection (50).

Some of the materials and methods employed in the Examples described below are used in more than one of the Examples. These materials and methods are described as general materials and methods.

General Materials and Methods

Synthesis of peptides. The cluster peptide-peptide-18 and T helper-peptide-18 constructs were synthesized on an automated peptide synthesized (No. 430A; Applied Biosystems, Foster City, Calif.) utilizing t-boc chemistry (51) according to the sequences shown in Table I (SEQ ID NOs:1–6). The peptides were cleared from the resin with HF and initially purified by size inclusion chromatography. (P4 Biogel; Bio-Rad Laboratories, Mountain View, Calif.). Purification to single peaks was achieved by reverse-phase HPLC on μbondapack reverse-phase C18 analytical and preparative columns (Waters Associates, Milford, Mass.). Peptide 55-18 was synthesized with an extra Ala at the N-terminus to avoid an N-terminal Gln, which would cyclize to form pyroglutamic acid.

Mice. H-2 congenic mice on the B10 background and BALB/c mice were purchased from Jackson Laboratories (Bar Harbor, Me.) or were bred in our colony at BioCon Inc., Rockville, Md. Mice used in this study were 8–20 weeks old.

ELISA. Wells of round bottom flexible PVC microtiter plates (#3912 Falcon Labware, Oxnard, Calif.) were coated overnight at 4° C. with 100 μl of 10 μM Peptide 18, substituted peptide 18, cluster peptide 3, cluster peptide 6, 0.2 μg/ml recombinant gp 120 (ABT, Advanced Biotechnologies, Mass.) or 2 μM sperm whale myoglobin in 0.1 M carbonate buffer pH 9.6. Recombinant gp120 plates were coated with 100 μl of a 0.2 μg/ml afftinity-purified rgp120 (ABT) in carbonate buffer. The plates were blocked with 1% BSA in phosphate buffered saline (PBS) for 1–1.5 h. at 4° C. and washed with PBS containing 0.05% Tween 20 and 1% BSA (PBSTB). Next, 100 μl of test serum was added to duplicate wells and incubated for 1–1.5 h. at 4° C. Test sera were assayed at 10 fold dilutions in PBSTB ranging from 1:100–1:10,000. The wells were then washed with 200 μl PBSTB 10 times using an automatic plate washer (BioRad Model 1550) and incubated for 1 h at 4° C. with 100 μl alkaline phosphatase-conjugated goat anti-mouse IgG (Promega, Madison, Wis.) diluted 1:7500 in PBSTB. After 10 washes, bound antibodies were detected by the addition of 100 μl of 1 mg/ml paranitrophenyl phosphate as substrate. The optical density at 405 nm was read with an ELISA reader. Specific absorbance was determined as the mean optical density at 405 nm on the relevant antigen coated wells minus the optical density 405 nm on nonrelevant sperm whale myoglobin coated wells. IgM specific for peptide 18 was detected using goat anti-mouse μ chain specific antibody (Sigma Chemical Co., St Louis, Mo.) followed by alkaline phosphatase conjugated anti goat. Total IgG and isotypes IgG1 and IgG2a were detected using biotin conjugated rat anti mouse monoclonals LO-MG1-13 for IgG1 and LO-MG2a-3 for IgG2a (BioSource International, Westlake Village, Calif.). Following the addition of strepavidin alkaline phosphatase (Sigma Immunochemicals, St. Louis, Mo.) substrate was added and plates read on the ELISA reader.

TABLE I

Sequences of T Helper Sites Linked to Peptide 18 HIV-1 IIIB

| Peptides | | Sequences* | Peptide 18 | MW (daltons) |
|---|---|---|---|---|
| PCLUS 1–18 | (102–121) | EQMHEDIISLWDQSLKPCVK | | 4038 |
| PCLUS 3–18 | (421–444) | KQIINMWQEVGKAMYAPPISGQIR | | 4397 |
| PCLUS 4–18 | (476–499) | RDNWRSELYKYKVVKIEPLGVAPT | RIQRGPGRAFVTIGK (308–322) | 4501 |
| PCLUS 6–18 | (821–853) | AVAEGTDRVIEVVQGAYRAIRHIPRRIRQGLER | | 5425 |
| P 53 | (827–841) | DRVIEVVQGAYRAIR | | 3383 |
| P 55† | (834–848) | AQGAYRAIRHIPRRIR | | 3573 |

*HIV-1 IIIB numbering is according to the Los Alamos Protein sequence data base (43). Previous reference to these peptides (42) used the Ratner numbering system (44).
†Peptide 55-18 is shown with an added alanine at the N-terminus to avoid formation of pyroglutamic acid.

The peptides containing the individual or multideterminant epitopes can be joined together by synthesizing them as a colinear peptide as described above. Alternatively, side-chain carboxylic acid and amino groups can be used to form peptide bonds; connection of the peptides through the side-chains provides an immunogen having a branched structure. In a third embodiment, the peptides can be joined by non-peptide conjugations. Several methods for conjugating peptides are well-known in the art. One such method is set forth in U.S. Pat. No. 4,886,782.

The invention is illustrated in detail by the Examples presented below. The Examples are presented as illustrations of preferred embodiments of the invention and are not meant to be limiting of the invention in any manner.

EXAMPLE I

Immunization of Mice to Produce High Titer Neutralizing Antibody Against HIV-1

The peptides of the present invention can be used to produce a high titer of AbN against a target antigen by immunization of a mammalian host with the peptide. In this Example, peptides derived from the sequence of the HIV-1 envelope glycoprotein gp 120 are used to elicit high titers of AbN in mice.

Immunizations. Mice were immunized intraperitoneally with 20 nanomoles of each peptide emulsified 1:1 in Freund's Complete Adjuvant (CFA). At days 21 and 31 post immunization blood was drawn by retroorbital bleed, allowed to clot and the serum removed and frozen at −20° C. Because antibody levels were found to still be rising between day 21 and day 31 after primary immunzation, the results from 31-day sera are reported. Selected groups of animals were boosted 36–52 weeks post primary immunization with 10 nanomoles of peptide in CFA intraperitoneally and bled 10–11 days later, when the secondary response was generally found to be optimal.

Neutralization assays of HIV-1. The quantitative infectivity microassay using CEM-SS cells was performed as described previously (52). Briefly, serial two-fold dilutions of 50 μl heat inactivated (56° C., 30 min.) test serum mixed with 50 μl of culture supernatant containing 200 syncytium forming units (SFU) of HIV-1-IIIB, or HIV-1 MN strain grown optimally from logarithmic cultures of H9 cells and previously cryopreserved and titered were incubated for 30 min at room temperature. The mixtures were added to duplicate wells containing $5 \times 10^4$ DEAE-dextran treated CEM-SS cells for 1 h at 37° C., after which the virus-antibody mixtures were removed and replaced with medium, and the cells cultured only in complete medium for 5 days (for HIV-1 IIIB) or 4 days (for HIV-1 MN, determined to be optimal for each virus strain) at 37° C. in 5% $CO_2$. Units of infectious virus were quantitated by subsequent syncytia formation of infected cells under an inverted microscope. The reciprocal geometric mean neutralization titer was expressed as the serum dilution capable of inhibiting HIV-1 foci by greater than 90% of control CEM-SS/HIV-1 infected cells infected with the indicated strain of HIV-1 (i.e. Vn/Vo<0.1). The assay measures neutralization of cell-free virus in the first incubation, not inhibition of syncytium formation, which is only the readout for enumerating infectious virus. No cytostatic or toxic properties of the serum alone on the CEM-SS cells were observed at the hightest concentration tested. Also, the heat inactivation at 56° C. for 30 min has been shown to eliminate the nonspecific neutralizing activity of mouse sera (53).

Determination of direct binding by immunofluorescence. To assess binding of peptide-induced antibodies to native gp 120, serial ten-fold dilutions of selected neutralizing and nonneutralizing sera were tested for binding to viral gp 120 expressed on the surface of HIV-1 IIIB productively infected cells in a live cell immunofluorescence assay (IFA) (52).

Competition ELISA binding curves. The binding tests were performed by mixing in sterile polypropylene tubes 125 μl of different dilutions of p18 (0–20 μM) or rgp120 (0–160 nM) in phosphate buffered saline pH 7.2, 1% ovalbumin, 0.05% Tween 20 with 125 μl of a constant dilution of antisera determined to be in the linear range of absorbance versus antibody dilution in the same buffer. After overnight incubation at 4° C. with gentle shaking, a volume of 100 μl was added to duplicate wells of a microtiter plate coated with the respective competing antigen p18 or gp120, incubated at 4° C. for 20 min. and a standard ELISA assay performed. Binding curves were generated using a four parameter logistic function of log serum dilution versus absorbance using a commercial software program (Biometalics Inc., Princeton, N.J.) and an estimated dissociation constant ($K_d$ value) for individual sera was determined.

Binding to P18 substituted peptides. The specificity of neutralizing and nonneutralizing sera were tested in a standard ELISA assay for binding to fifteen substituted p18 peptides (37) coated onto plastic microtiter wells.

The synthetic multideterminant peptides (Table I), called "cluster peptides" (abbreviated PCLUS in the names of specific constructs), each constitute clusters of overlapping, but distinct, shorter T helper determinants identified in previous studies (42,54,55). Three cluster peptides, PCLUS 3, 4, and 6 used in this study were chosen because they fulfilled the criteria of eliciting proliferative responses in four independent MHC haplotypes of mice that differ in both an I-A and I-E molecule, and also in humans of multiple HLA types (42,56,57). PCLUS 1 was strongly recognized by only one strain of mice, B10.BR, yet stimulated IL-2 production in 23 of 36 HIV seropositive, flu-positive donors. Peptide HP53 (residues 827–841 in the Los Alamos database (43) numbering, which is 7 less than that of Ratner (44) used previously (42,54,55)) and peptide HP55 (residues 834–848) have previously been identified as T helper epitopes of the HIV IIIB envelope sequence in mice of the $A^kE^k$ and $A^bE^b$ haplotypes and the $A^kE^k$, $A^bE^b$, $A^dE^d$, and $A^sE^s$ haplotypes respectively, and are contained within the longer PCLUS peptides. ($E^b$ and $E^s$ are used here to indicate the expressed $E_\beta^{\,b}E_\alpha$ and $E_\beta^{\,s}E_\alpha$ molecules, respectively. Although the nonpolymorphic $E_\alpha$ is not expressed in pure H-$2^b$ and H-2s haplotypes, we used recombinant strains that express $E_\alpha$). Peptide HP53 (also referred to as env TH 4.1) was also previously shown to elicit IL-2 production in peripheral blood lymphocytes of asymptomatic HIV-seropositive human patients (57). Peptide 18 (residues 308–322) is a B cell epitope located within the hypervariable V3 loop region of the HIV-1 IIIB envelope known as the principal neutralizing determinant (PND), and is the major immunodominant cytotoxic T cell epitope in mice (45), as well as being recognized by human CTL (46).

Synthetic peptide vaccine constructs were prepared by synthesizing peptide 18 at the carboxy terminus of the cluster peptide. Immunization of mice with 20 nanomoles of these constructs produced enhanced peptide 18 specific antibodies, whereas no peptide 18 specific antibody was detected in mice immunized with peptide 18 alone (Table II). The orientation of T helper cell and B cell epitopes proved crucial for the immunogenicity of the construct since although cluster peptide 3-18 elicited an antibody response in all four strains tested, the reverse polarity construct, P18-cluster peptide 3 in which the helper site was C-terminal to P18, elicited an antibody response to peptide 18 in only one strain, B10.HTT, and at a significantly lower level.

TABLE II

HIV IIIB Peptide 18 Specific Antibody Response and Neutralizing Activity in Four Strains of Mice 31 days Following a Single Immunization with 20 nanomole T Helper-P18 Peptide

| Mouse Strain | BALB/c or B10.D2 ($A^dE^d$) | | B10.BR or B10.A ($A^kE^k$) | | B10.HTT ($A^sE^s$) | | B10.A(5R) ($A^bE^b$) | |
|---|---|---|---|---|---|---|---|---|
| Peptide | ELISA* | Neutralization† | ELISA | Neutralization | ELISA | Neutralization | ELISA | Neutralization |
| P18 | 0.00 | — | 0.00 | — | 0.00 | NT‡ | 0.00 | NT |
|  |  | (0/5) |  | (0/5) |  |  |  |  |
| 53-18¶ | 0.05 ± 0.3 | NT | 0.13 ± .05 | NT | 0.78 ± .60 | — | 2.30 ± .03 | 32.0 |
|  |  |  |  |  |  | (0/5) |  | (1/5) |
| 55-18¶ | 0.48 ± .15 | — | 0.00 | NT | 2.47 ± .25 | 22.6 | 0.32 ± .23 | NT |
|  |  | (0/5) |  |  |  | (2/5) |  |  |
| PCLUS 1-18 | 0.12 ± .03 | NT | 0.68 ± .04 | 16.0 | 0.13 ± .05 | NT | 0.07 ± .04 | NT |
|  |  |  |  | (2/5) |  |  |  |  |
| PCLUS 3-18§ | 0.39 ± .14¶ | 10.6 | 0.50 ± .19¶ | — | 2.70 ± .30 | 32.0 | 0.86 ± .16 | — |
|  |  | (5/5) |  | (0/5) |  | (1/6) |  | (0/5) |
|  | 0.45 ± .17 | 9.5 | 0.28 ± .08 | — | 0.51 ± .22 | — | 0.03 ± .01 | NT |
|  |  | (4/5) |  | (0/5) |  | (0/5) |  |  |
| PCLUS 4-18 | 0.64 ± .19 | 8.0 | 0.38 ± .07 | NT | 0.61 ± .16 | — | 0.16 ± .04 | NT |
|  |  | (1/4) |  |  |  | (0/3) |  |  |
| PCLUS 6-18§ | 0.84 ± .12 | 9.5 | 0.94 ± .24 | 19.0 | 0.88 ± .23 | 11.3 | 0.63 ± .23 | 8 |
|  |  | (4/5) |  | (3/5) |  | (4/5) |  | (1/5) |
|  | 0.77 ± .13 | 42.2 | 0.80 ± .06 | 32.0 | 0.16 ± .07 | — | 0.87 ± .08 | 20.2 |
|  |  | (5/5) |  | (4/5) |  | (0/5) |  | (3/5) |

*Mean p18 Specific Absorbance ± S.E.M. of 5 mouse sera tested at a 1:1000 serum dilution
†Reciprocal Geometric Mean IIIV IIIB Neutralizing Antibody Titer expressed as the serum dilution capable of inhibiting HIV IIIB specific foci by greater than 90% of control CEM-SS/HIV IIIB infected cells.
(No. of mice with positive neutralizing titers/total tested.)
‡NT Not tested
¶B10.D2 and/or B10.A mouse strains used.
§For PCLUS 3-18 and PCLUS 6-18, two different experiments are shown.

Figure 1A:
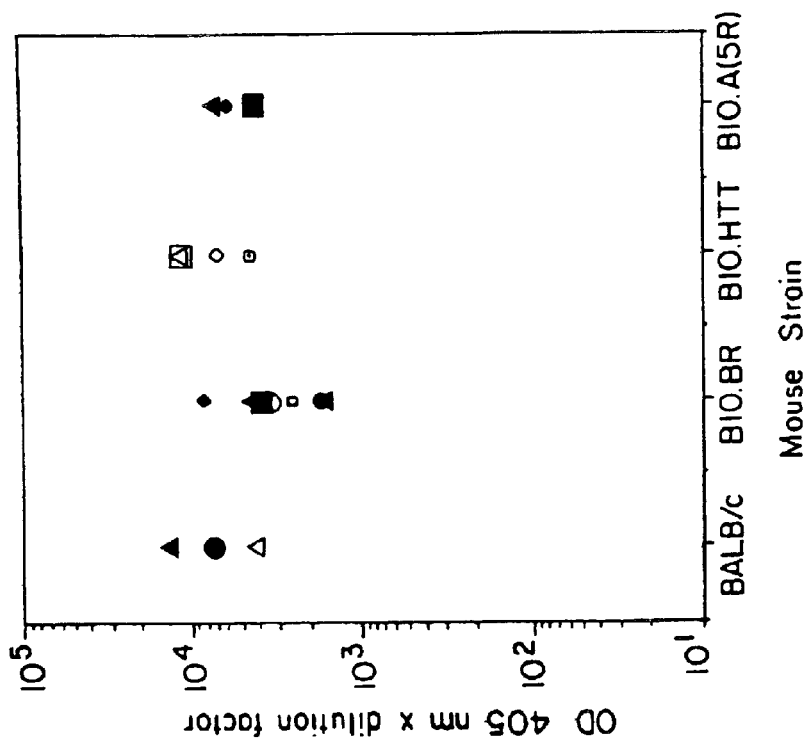
FIGS. 1A, 1B P18 specific antibody response of mice of four different MHC haplotypes following immunization with cluster peptide 6-18. (a) the primary antibody response 31 days after immunization with 20 nanomoles of peptide (levels at day 21 were lower; see Results). (b) an anamestic response to a boost of 10 nanomoles of peptide 37 and 49 weeks after primary immunization. Symbols correspond to individual mice except for + which indicates a prebleed pool.
Figure 1B:
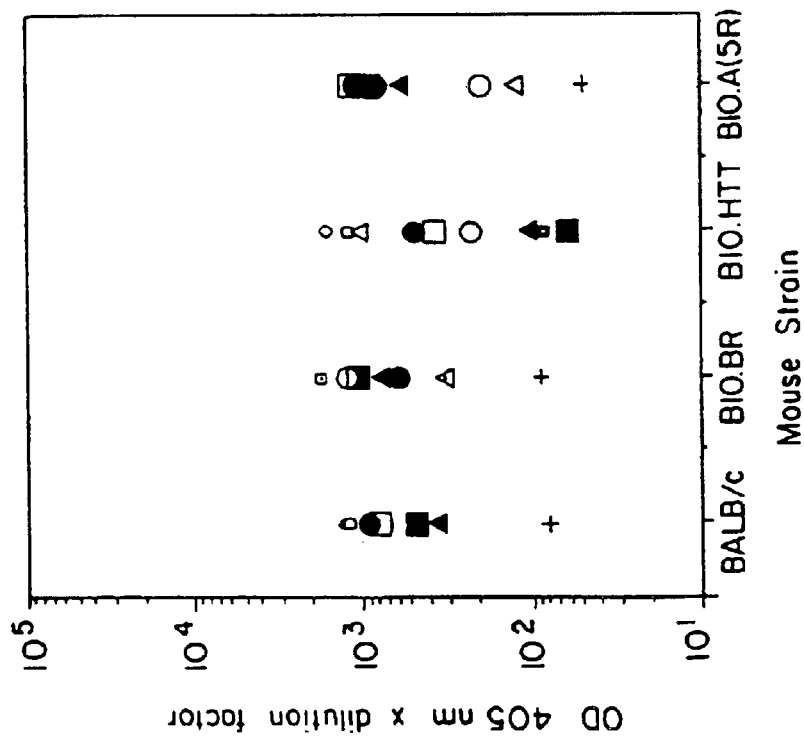

In most cases the T helper peptide component of our constructs provided help for peptide 18-specific antibody in the strains in which these T cell epitopes elicited proliferative responses in previous studies (54,58). In the case of peptide 53-18 and 55-18, the $A^bE^b$ and $A^kE^k$ haplotypes responded to peptide 53-18 and the $A^sE^s$, $A^dE^d$, and $A^bE^b$ haplotypes responded to peptide 55-18 (Table II). In addition, $A^sE^s$ mice responded to peptide 53-18, but $A^kE^k$ mice failed to make anti-P18 antibodies to peptide 55-18 even though they were previously shown to proliferate in response to P55 .(54). PCLUS 1-18, which encompasses T helper cell epitopes recognized by all four strains of mice used in this study, was able to elicit a strong antibody response in only one strain, B10.BR, and a marginal one in two other strains, B10.D2 and B10.HTT. This was not surprising since in our previous study (42) we showed that cluster peptide 1 was not simply the sum of its parts, but failed to stimulate proliferation in some strains in which a smaller component of the cluster peptide did. The larger peptide may fold back upon itself and hinder interaction with the MHC or T cell receptor or may undergo different processing which would destroy a component epitope. PCLUS 3-18, 4-18, and 6-18 elicited strong peptide 18 antibody responses in all the strains of mice tested in at least one experiment, as measured by ELISA. These results show that by linking a B cell epitope to the carboxy terminus of a cluster of immunodominant T cell epitopes, in most cases the processing of individual epitopes is patent and the T cells elicited are capable of providing help to the B cell for production of specific antibody. Since a single immunization with these cluster peptide-peptide-18 constructs could induce high levels of P18-specific antibodies, we tested to see if a boost, which might represent a viral challenge, would produce a characteristic anamnestic response resulting in enhanced peptide 18 specific antibody (FIG. 1). After the primary immunization, the response to which is slower than a secondary immunization, sera were obtained on days 21 and 31, but the antibody levels were still rising on day 31. Therefore, we show in panel A individual mean peptide 18 specific absorbance readings for animals immunized with 20 nanomoles of PCLUS 6-18 and bled 31 days post immunization and compare in panel B individual absorbance readings for animals boosted with 10 nanomole of PCLUS 6-18, 37 and 49 weeks post primary immunization and bled 11 days later, when the secondary response usually peaks. The increase in antibody response observed after boosting was between 2.5 to 12 fold.

To assess usefulness of these synthetic peptide constructs in a vaccine, it was necessary to determine if the antibody elicited to peptide 18 following a single immunization with these constructs was capable of neutralizing the virus in vitro. Neutralizing activity, expressed as the reciprocal geometric mean titer capable of inhibiting cell-free infectious units of HIV IIIB by greater than 90% compared to control CEM-SS/HIVIIIB infected cells was elicited in peptide 53-18, 55-18, and PCLUS 1-18 in the strains which responded by a specific antibody response. However antibody was neutralizing in only one of five animals immunized with 53-18 and only two of five immunized with 55-18 and PCLUS 1-18 (Table II). This occurred despite equal or higher levels of peptide 18 specific antibodies by ELISA in other animals within the group. The finding that total peptide 18-specific antibody levels did not correlate with neutralization was extended by an interstrain comparison in animals immunized with PCLUS 4-18. Although all strains responded with significant levels of antibody to peptide 18 by ELISA compared to prebleed controls, only one of four animals of the BALB/c strain generated neutralizing antibody at the lowest dilution tested (Table II). The lack of correlation between specific peptide 18 antibody response and neutralizing activity was especially apparent in animals immunzed with PCLUS 3-18. Significant levels of peptide 18 specific antibody were elicited as determined by ELISA in all strains of mice immunized with PCLUS 3-18, and the animals of the $A^sE^s$ haplotype showed the strongest antibody response to this construct. Nevertheless, only animals of the $H-2^d$ haplotype made antibodies capable of neutralizing virus in vitro (9 of 10 animals), despite lower levels of antibody by ELISA. This finding suggests that the in vivo induction of neutralizing antibody by the B cell epitope (peptide 18) immunogen depends on other factors in addition to the level of help, such as the specificity of helper T cells, or other MHC-linked regulatory factors.

Figure 2A:
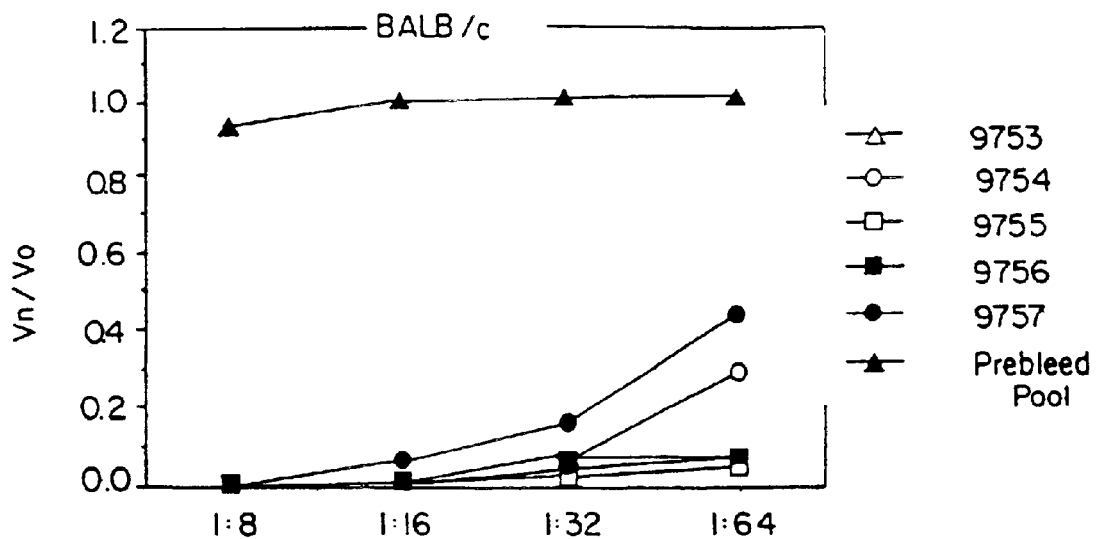
Figure 2B:
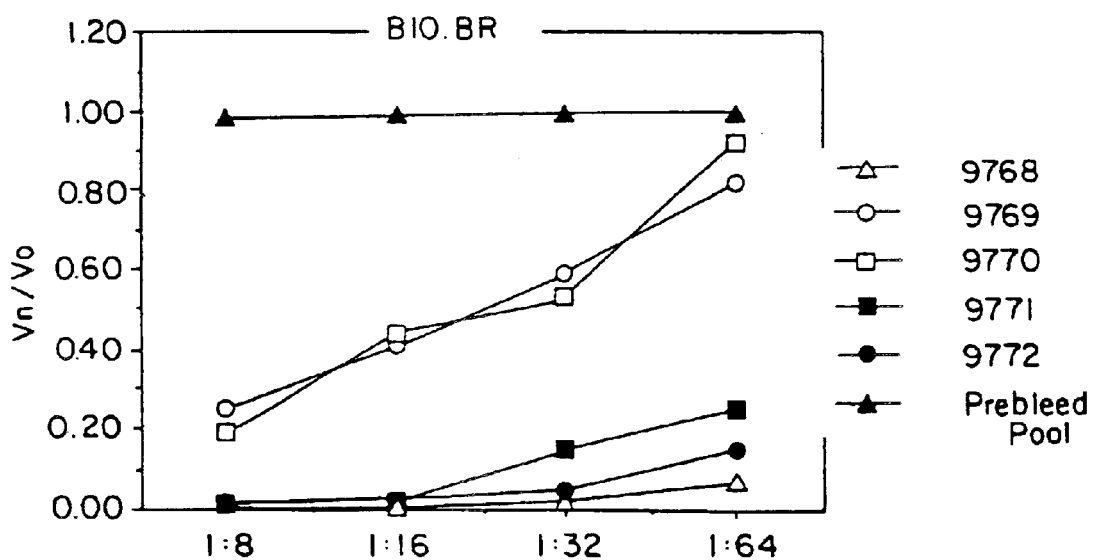
Figure 3A:
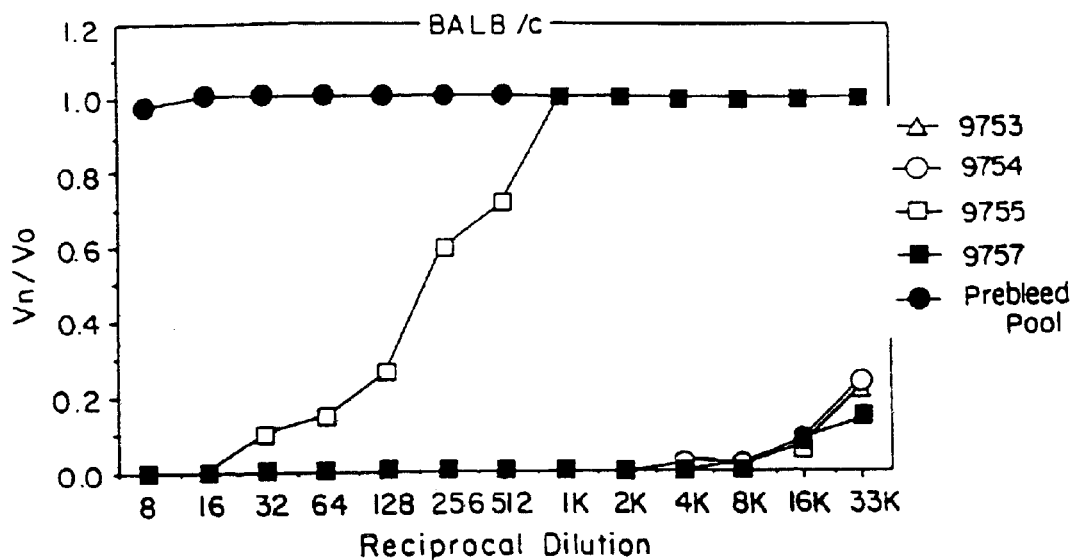
FIGS. 3A–D HIV-1 IIIB neutralization profiles of four strains of mice 10 days following a single boost with 10 nanomole of PCLUS 6-18 39–42 weeks post primary immunization. Vn/Vo is plotted versus reciprocal dilution for each numbered serum as in FIG. 2. Animal numbers and symbols represented correspond to those in FIG. 2 for the primary response. Note that the abscissa for mouse strain BALB/c is different from the other strains, such that the endpoint dilution for BALB/c is 1:32,768 whereas for the other strains it is 1:4096.
Figure 3B:
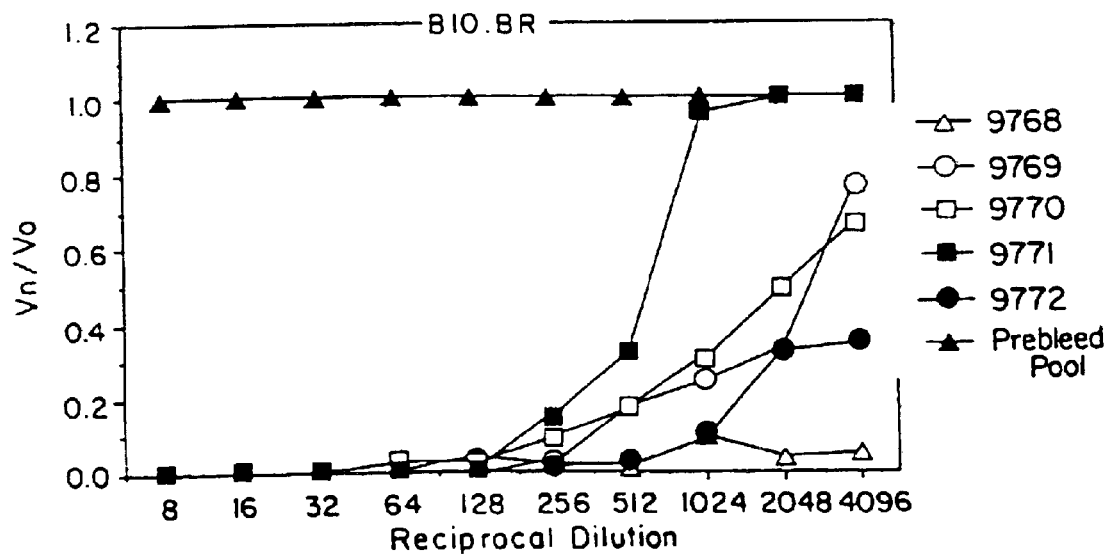
Figure 3C:
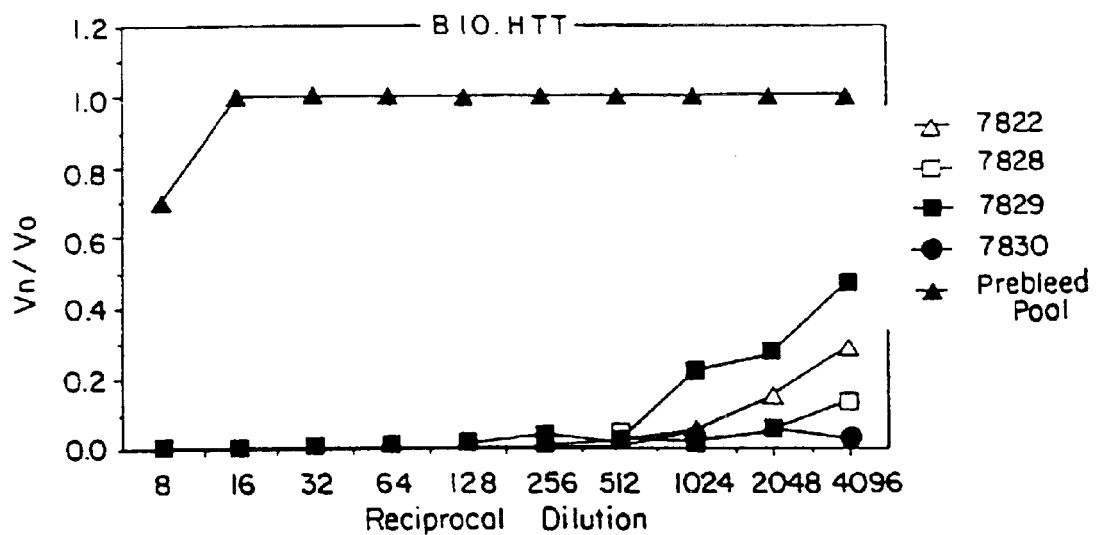
Figure 3D:
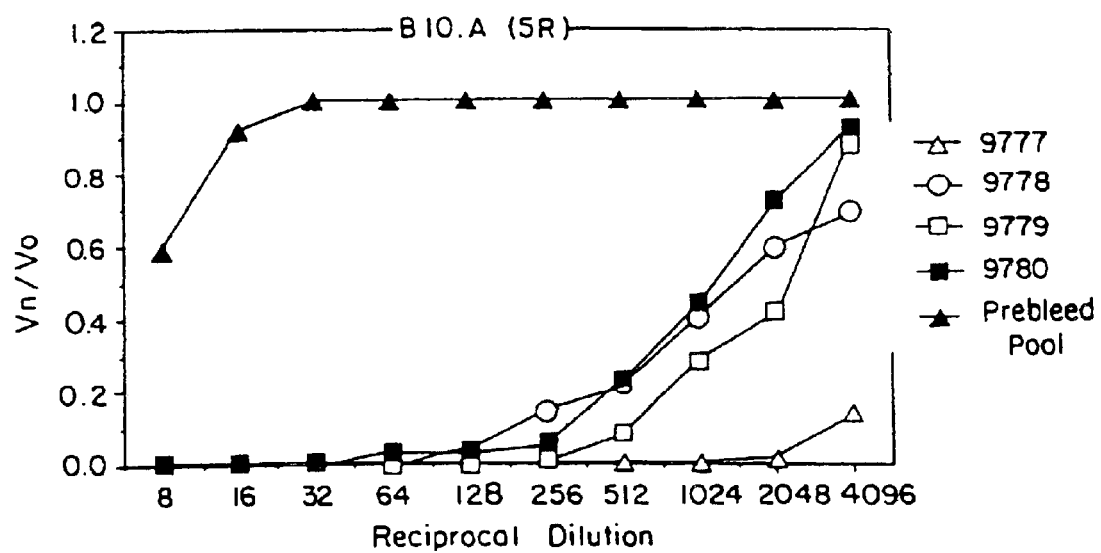

PCLUS 6-18 reproducibly elicited neutralizing antibody in all strains tested in which it elicited a significant antibody response by ELISA (Tables II and III). The geometric mean neutralizing antibody titers achieved in BALB/c (42.2) and B10.BR (32.0) correspond to levels of neutralizing activity directed to the V3 loop that have been found sufficient to protect chimpanzees from a live homologous viral challenge (30). Neutralization titration profiles from two separate experiments for each group of animals following a single immunization with PCLUS 6-18 are shown in FIG. 2.

Each animal received 20 nanomoles of synthetic peptide emulsified in CFA (1:1) intraperitoneally in a volume of 0.1 ml. Neutralizing activity is determined in a microculture syncytium-forming assay using the HIV-1 IIIB HX3 strain and is expressed as Vn/Vo where Vn is the mean number of syncytia forming units (SFU) in duplicate test wells and Vo the number of SFU in control wells incubated without test sera. Each curve represents serial two fold dilutions of individual mouse serum (designated by animal number) except the prebleed pool which includes all animals within a group. The two columns represent two separate experiments.

It is interesting to note that three of five BALB/c mice shown in the first panel had 90% neutralizing titers greater than 64, which was the highest dilution tested. In addition, four of ten B10.BR mice shown in panels 3 and 4 exhibited neutralizing titers greater than 64. Over half (22/40) of all animals immunized with cluster peptide 6-18 demonstrated 50% neutralization of live virus at a dilution of 1:64 and all but one neutralized 50% of the virus at one of the dilutions tested. This single animal number 6269 B10.HTT had a negligible antibody response in a group that appeared to be poorly immunized. The mice that responded to the primary immunization were given a single boost with the same construct in CFA 37 or 49 weeks after the first immunization. This single boost produced remarkably high titers of neutralizing antibody with 90% neutralization occurring out to 1:2048–1:4096 in many animals and 1:16,384 in some (FIG. 3 and Table IV). These neutralizing titers against the homologous viral strain after just two immunizations are at least four to eight fold higher than the highest titers of other polyclonal sera induced by any immunization that we have ever observed. (8,59). Moreover, the timing indicates that memory from the primary immunization lasted at least 11 months. Furthermore, in three of four strains boosted with PCLUS6-18 IIIB, the sera were also capable of neutralizing the HIV-1 MN strain, albeit at much lower titer (Table IV). Although mice of the $H-2^d$ haplotype produced some of the highest neutralization titers against HIV-1 IIIB (e.g. 1:16,384) following a single boost, none of these sera showed cross-neutralizing activity against the MN strain.

In order to attempt to explain why some sera had high neutralizing activity and other sera with similar ELISA titers for the same short sequence did not, we compared affinity, isotype, fine specificity and other properties of neutralizing and nonneutralizing antibodies generated by each of the cluster peptide-peptide-18 immunizations (summarized in Table III). It is important to note that all the sera tested, with the exception of that of one animal (B10.BR # 9770), were capable of neutralizing the virus at some dilution as assessed by 50% inhibition compared to control sera, even if they were nonneutralizing by the criterion of 90% inhibition. Therefore it may be more difficult to differentiate specificity differences, since sera that are nonneutralizing at 90% inhibition may possess low levels of neutralizing antibodies which would blur the distinction.

TABLE III

Properties of Neutralizing Antibodies Generated By Cluster Peptide P18 Immunization

| Cluster Peptide/ Mouse Strain | Serum # | Neutralization IIIB 90% | Neutralization IIIB 50% | Neutralization MN 90% | IIIB/119 Binding (IFA) | ELISA p18 | ELISA gp120 | PCLUS 3 | PCLUS 6 | IgM (P18) | IgM (pg120) | IgG1 | IC 50* p18 | IC 50* gp120 |
|---|---|---|---|---|---|---|---|---|---|---|---|---|---|---|
| PCLUS 1-18 | | | | | | | | | | | | | | |
| B10.BR | 6256 | 16 | >64 | | | 0.81 | 1.66 | 0.29 | 0.16 | 0.59 | 0.63 | | | |
| | 4597 | 16 | >64 | | | 0.67 | 1.69 | 0.14 | 0.09 | | | | | |
| | 4599 | — | 8 | | | 0.75 | 1.66 | 0.15 | 0.09 | | | | | |
| | Prebleed Pool | — | — | | | 0.00 | | | | | | | | |
| PCLUS 3-18 | | | | | | | | | | | | | | |
| BALB/c | 6242 | 8 | >64 | Negative | | 0.49 | 1.17 | 0.09 | | 0.35 | 0.38 | | | |
| | 6243 | 8 | 32 | | | 0.44 | 1.17 | 0.06 | | 0.42 | 0.33 | 0.91 | 9.30E−07 | 7.19E−10 |
| | 6744 | — | 32 | | | 0.08 | | | | 0.41 | 0.33 | | | |
| | 6245 | 16 | >64 | | Negative | 0.98 | 1.68 | 0.05 | 0.02 | 0.41 | 0.33 | | | |
| | 6246 | 8 | 16 | | | 0.79 | 1.57 | 0.05 | 0.09 | 0.52 | 0.39 | | | |
| | Prebleed Pool | — | — | Negative | | 0.13 | 0.20 | 0.03 | 0.02 | | | | | |
| B10.BR | 6252 | — | 16 | | | 0.66 | 1.19 | 0.05 | 0.01 | | | | | |
| | 7803 | — | 8 | | | 0.31 | 1.19 | 0.04 | 0.07 | 0.43 | 0.59 | 0.63 | | |
| | 7804 | — | 8 | | | 0.46 | | | | | | | | |
| | 7806 | — | 16 | | | 0.10 | | | | | | | | |
| | 6253 | — | 32 | | | 0.10 | | | | | | | | |
| | Prebleed Pool | — | — | | | 0.12 | 0.20 | 0.05 | 0.02 | | | | | |

TABLE III-continued

Properties of Neutralizing Antibodies Generated By Cluster Peptide P18 Immunization

| Cluster Peptide/ Mouse Strain | Serum # | Neutralization IIIB 90% | Neutralization IIIB 50% | MN 90% | IIIB/119 Binding (IFA) | ELISA p18 | gp120 | PCLUS 3 | PCLUS 6 | IgM (P18) | IgM (pg120) | IgG1 | IC 50* p18 | IC 50* gp120 |
|---|---|---|---|---|---|---|---|---|---|---|---|---|---|---|
| B10.HTT | 7128 | — | 32 | | | 0.75 | | | | | | | | |
| | 7129 | — | 8 | | | 0.00 | | | | | | | | |
| | 7130 | — | 16 | | Negative | 0.84 | 1.58 | 0.05 | 0.09 | 0.56 | 0.56 | | 9.25E−07 | 5.14E−10 |
| | 7131 | — | 16 | | | 0.33 | 0.85 | 0.08 | 0.13 | 0.41 | 0.54 | | | |
| | 7132 | — | 16 | | | 1.26 | 1.67 | 0.08 | 0.12 | 0.56 | 0.57 | | | |
| | Prebleed Pool | — | — | | | 0.12 | 0.16 | 0.03 | 0.02 | | | 0.47 | | |
| B10.A(5R) | 4832 | — | 8 | | | 0.86 | | | | 0.32 | 0.27 | | | |
| | H3043 | — | 8 | | | 0.51 | | | | 0.37 | 0.40 | | | |
| | Prebleed Pool | — | — | | | 0.00 | | | | | | | | |
| PCLUS 4-18 | | | | | | | | | | | | | | |
| BALB/c | 9748 | — | 8 | | | 0.63 | | | | | | | | |
| | 9749 | — | 8 | | | 0.69 | | | | | | | | |
| | 9750 | 8 | 32 | | | 1.19 | 1.34 | 0.06 | 0.01 | | | | | |
| | 9752 | — | — | | | 0.06 | | | | | | | | |
| B10.A(5R) | 9776 | — | — | | | 0.18 | 0.21 | 0.02 | 0.02 | | | | | |
| | Prebleed Pool | | | | | 0.09 | | | | | | | | |
| PCLUS 6-18 | | | | | | | | | | | | | | |
| BALB/c | 6247 | 32 | >64 | Negative | | 0.44 | 1.56 | 0.06 | 1.20 | 0.47 | 0.58 | | | |
| | 6248 | 8 | 32 | | | 0.75 | | | | | | | | |
| | 6249 | 8 | | Negative | | 0.78 | | | | | | | | |
| | 6250 | 16 | >64 | | | 1.29 | | | | | | | | |
| | 6251 | — | >64 | | | 0.95 | | | | 0.41 | 0.58 | 0.82 | 6.77E−07 | 3.88E−10 |
| | 9753 | >64 | >64 | | | 0.36 | | | | | | | | |
| | 9754 | 32 | >64 | | | 0.85 | | | | | | | | |
| | 9755 | >64 | >64 | | | 0.47 | | | | | | | | |
| | 9756 | >64 | >64 | | | 0.99 | 1.50 | 0.05 | 1.15 | | | | | |
| | 9757 | 16 | 32 | | | 1.17 | | | | | | | | |
| | Prebleed Pool | — | — | | | 0.08 | | | | | | | | |
| B10.BR | 6359 | 16 | >64 | | | 1.10 | 2.07 | 0.05 | 0.87 | 0.44 | 0.43 | | | |
| | 6254 | — | 64 | | | 0.37 | 1.22 | 0.00 | 0.46 | 0.38 | 0.36 | | | |
| | 6255 | 8 | 32 | Negative | | 1.14 | 1.33 | 0.00 | 1.23 | | | | | |
| | 7367 | 16 | >64 | | | 1.21 | | | | | | | | |
| | 9768 | >64 | >64 | | | 0.79 | | | | | | | | |
| | 9769 | — | 16 | | | 0.63 | 1.43 | 0.06 | 0.81 | 0.50 | 0.71 | | | |
| | 9770 | — | — | | 1:100 | 1.13 | 1.54 | 0.19 | 8.17 | | | | | |
| | 9771 | 16 | >64 | | | 0.97 | 0.44 | 0.74 | | | | | | |
| | 9772 | 32 | >64 | | | 0.94 | 1.69 | 0.09 | 1.53 | 0.55 | 0.81 | | 7.44E−07 | 2.07E−09 |
| | 7309 | >64 | >64 | | 1:1000 | 0.33 | | | | | | | | |
| | Prebleed Pool | — | — | | | 0.11 | 0.22 | 0.07 | 0.04 | | | | | |
| B10.HTT | 7827 | 8 | >64 | | | 1.03 | 1.58 | 0.08 | 0.23 | 0.41 | 0.63 | | | |
| | 7828 | 16 | 64 | | | 1.10 | 1.54 | 0.12 | 0.96 | 0.49 | 0.51 | | | |
| | 7829 | 16 | >64 | | 1:10 | 0.90 | 1.58 | 0.03 | 1.02 | 0.69 | 0.50 | | | |
| | 7830 | 8 | 32 | | 1:100 | 1.32 | 1.49 | 0.03 | 0.40 | 0.90 | 0.59 | | | |
| | 7822 | — | 32 | | | 1.00 | | | | | | | | |
| | 6267 | — | >64 | | | 0.19 | 0.19 | 0.08 | 0.11 | 0.31 | 0.36 | | | |
| | Prebleed Pool | — | — | | | 0.08 | 0.18 | 0.02 | 0.02 | | | | | |
| B10.A(5R) | 4578 | — | 16 | | | 0.99 | 1.47 | 0.02 | 0.59 | 0.37 | 0.49 | | | |
| | 4579 | 8 | >64 | | | 0.97 | 1.51 | 0.06 | 1.29 | 0.59 | 0.63 | | | |
| | 9777 | >64 | >64 | | | 1.10 | 1.64 | 0.08 | 0.25 | 0.44 | 0.74 | | | 2.73E−10 |
| | 9778 | — | 16 | | | 0.59 | | | | | | | | |
| | 9779 | — | 16 | | | 0.57 | 1.39 | 0.15 | 0.86 | | | | | |
| | 9780 | 8 | 32 | | | 0.86 | | | | | | | | |
| | 9781 | 32 | 32 | | | 0.76 | | | | | | | | |
| | Prebleed Pool | Negative | | | | 0.05 | 0.20 | 0.03 | 0.01 | | | | | |

IC 50 = concentration of peptide producing 50% inhibition in a competitive ELISA, as an estimate of Kd (inverse avidity)

TABLE IV

Properties of Sera Boosted with 10 nanomole Cluster Peptide-P18

| Cluster Peptide/ | | ELISA | | Neutralization | | | |
|---|---|---|---|---|---|---|---|
| | | | | IIIB | | MN | |
| Mouse Strain | Serum # | 1:1,000 | 1:10,000 | 90% | 50% | 90%* | 50% |
| PCLUS 3-18 | | | | | | | |
| BALB/c | 6243 | 0.44 | 0.08 | 8 | 32 | — | — |
| | 6244 | 0.64 | 0.12 | 256 | >512 | | |
| | 6246 | 1.48 | 0.54 | 128 | >512 | | |
| PCLUS 6-18 | | | | | | | |
| BALB/C | 6247 | 2.27 | 0.42 | 4068 | >32,768 | | |
| | 6251 | 1.49 | 0.66 | 64 | 512 | — | — |
| | 9753 | 1.45 | 1.41 | 16,384 | >32,768 | | |
| | 9754 | 1.47 | 0.72 | 16,384 | >32,768 | — | — |
| | 9755 | 0.12 | 0.10 | 32 | 128 | | |
| | 9757 | 1.75 | 1.32 | 16,384 | >32,768 | — | — |
| B10.BR | 7309 | 1.12 | 0.17 | 4096 | 16,384 | | |
| | 7367 | 1.25 | 0.34 | 4096 | >32,768 | | |
| | 9768 | 1.64 | 0.41 | 1024 | 2048 | — | >512 |
| | 9769 | 1.54 | 0.17 | 256 | 2048 | — | — |
| | 9770 | 1.50 | 0.36 | 256 | 2048 | | |
| | 9771 | 1.65 | 0.86 | 128 | 512 | | |
| | 9772 | 1.23 | 0.26 | 1024 | >4096 | — | >512 |
| B10.HTT | 7822 | 1.77 | 1.15 | 1024 | >4096 | 128 | 512 |
| | 7828 | 1.42 | 1.10 | 2048 | >4096 | 128 | >512 |
| | 7829 | 1.39 | 0.68 | 512 | >4096 | 128 | >512 |
| | 7830 | 1.19 | 0.43 | 16,384 | >32,768 | | |
| B10.A(5R) | 9777 | 1.49 | 0.76 | 2048 | >4096 | — | 128 |
| | 9778 | 1.23 | 1.02 | 128 | 512 | — | >512 |
| | 9779 | 1.55 | 0.41 | 512 | 2048 | — | 64 |
| | 9780 | 1.28 | 0.59 | 256 | 1024 | — | 256 |

ELISA readings measured at 405 nm and reciprocal dilution neutralization titers of individual mouse sera 39–52 weeks following a single boost with 10 nanomole of cluster peptide 3 or 6 in four different strains of mice. Neutralization of homologous virus at 90% and 50% endpoints is indicated in the column labeled IIIB indicating HIV-1 IIIB and cross neutralization in the column MN representing HIV-1 MN.

– indicates negative at the lowest dilution tested, 1:64.

Results in column 4 show direct binding to HIV IIIB-infected cells by immunofluorescence. Three of five sera from animals immunized with cluster peptide 6-18 and capable of neutralizing virus by 90% in the syncytium-forming assay exhibited binding to virus infected cells, although there was no correlation between neutralizing titer and IFA titer. Two neutralizing sera from mice immunized with PCLUS 3-18, #6245, and PCLUS 6-18, #6249, failed to bind infected cells by IFA. In addition, one of two nonneutralizing sera, from mouse #9770 immunized with PCLUS 6-18, exhibited binding to virus-infected cells despite the absence of any neutralizing activity at the level of 50% inhibition in the synctium forming assay. In this small sample we were not able to detect a difference between neutralizing and nonneutralizing sera by IFA.

Sera from animals immunized with the cluster peptides were tested for binding to rgp 120 in an ELISA assay. Note that it is only relevant to compare absorbance reading from the ELISA assays in Table III within columns and not between columns, since different reagents and assay conditions are employed for each type of ELISA. All immune sera tested bound rgp120 whereas prebleed control sera did not, and there was no significant difference in level found between neutralizing and nonneutralizing sera. In addition no difference between sera could be found in IgM levels which bound P18 or rgp 120. In a small sample, the isotype of antibodies elicited to P18 was determined to be $IgG_1$. None of the sera tested showed any antibodies of the isotype $IgG_{2a}$. No correlation was found between isotype and neutralizing activity.

Since antibodies elicited to the T helper sites may play a role in a subsequent viral infection, it was important to determine if sera from animals immunized with the cluster peptide-peptide-18 constructs contained any antibodies to the cluster peptides themselves. Also, if antibodies to the helper sites were neutralizing, these could account for the lack of correlation between binding to peptide 18 and neutralization. We tested this possibility in an ELISA using plates coated with cluster peptide 3 alone or cluster peptide 6. None of the animal sera tested showed binding to PCLUS 3. In contrast, all animals immunized with PCLUS 6-18 produced antibodies that were reactive to the T helper site and the level of antibody produced was proportional to their peptide 18 response, whereas none of the control animals produced anti-cluster peptide 6 antibodies. However, it is unlikely that neutralizing activity of these sera was due to antibodies to cluster peptide 6, because of its location in the intracytoplasmic tail of gp 41, and the lack of cross-neutralization of the MN strain (Table III), as discussed further below. Therefore, the neutralizing activity musts be primarily directed to the P18 portion of the construct.

Figure 4A:
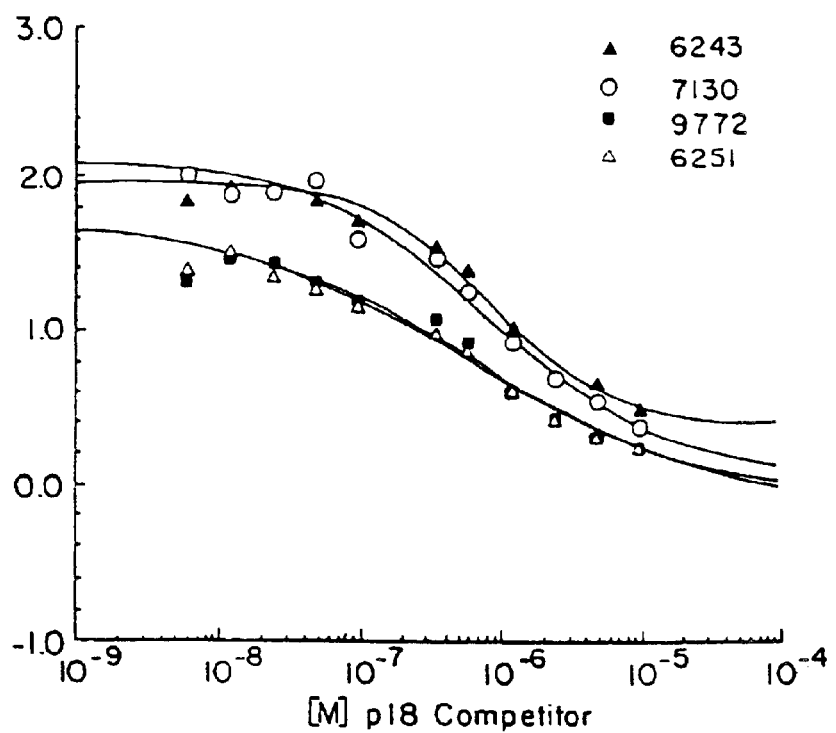
FIGS. 4A, 4B Competitive binding curves using p18 and rgp 120 as competitor, to assess affinity of antibodies for peptide and whole protein. Solid symbols represent sera with >90% neutralizing activity at one of the dilutions tested and the open symbols represent sera with <90% neutralizing activity at the lowest dilution tested. The data are representative of 3–4 experiments.
Figure 4B:
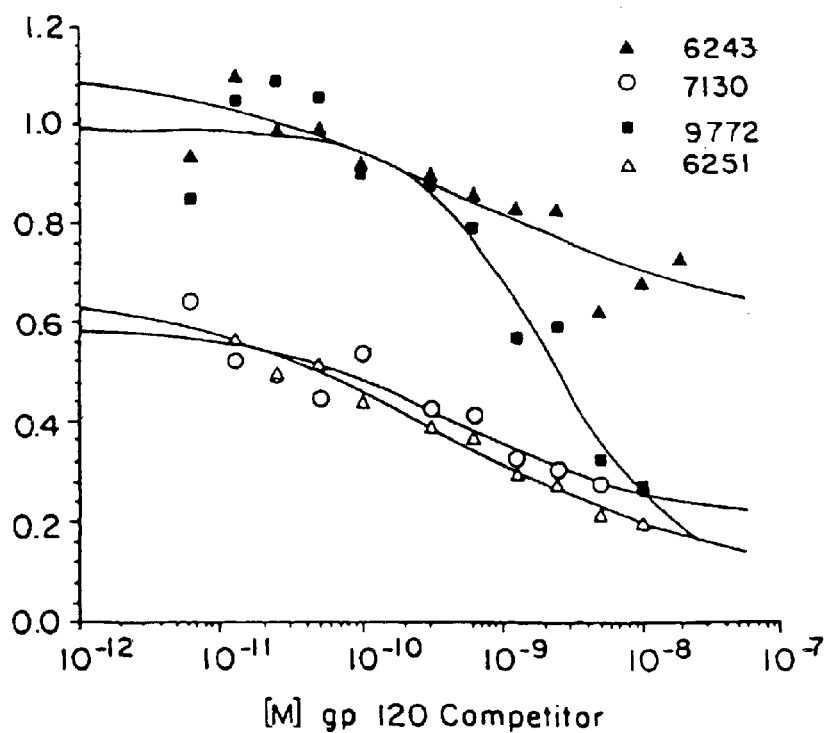

It remained possible that differences in neutralizing ability were due to differences in affinity of antibodies. To test this possibility, sera selected on the basis of their ability to neutralize virus in the quantitative infective syncytium-plaque forming assay were mixed with various concentrations of peptide 18 or rgp 120 and allowed to achieve solution phase equilibrium. Dilutions of competitor were allowed to reach solution phase equilibrium in an overnight incubation at 4° C. with a $10^{-3}$ dilution of each antiserum. Free antibody was then determined by short term incubation on competing peptide 18 or rgp 120 coated plates respectively, in an ELISA assay. Concentrations required for 50% maximal competition ($IC_{50}$), as estimates of $K_d$, were determined for each serum tested from the binding curves. Each experiment was repeated three to four times and representative results are shown in FIG. 4. Binding avidities (reciprocal of $K_d$) of all sera tested were over two logs higher (i.e. $IC_{50}$ two logs lower) when tested with rgp 120 than with peptide 18 (Table III). Binding avidities of neutralizing and nonneutralizing sera to peptide 18 were comparable, and any differences in avidity for rgp 120 were equivocable. In one case neutralizing serum from an animal immunized with cluster peptide 6-18, B10.BR mouse number 9772, showed a 5-fold lower binding avidity for rgp 120 than a corresponding nonneutralizing serum, BALB/c number 6251, whereas another neutralizing serum in this same group, B10.A(5R) mouse number 9777, showed only a 1.4 fold lower binding avidity than corresponding nonneutralizing serum 6251. The fact that the binding curves were not as steep as expected reveals that these sera were not homogeneous or monoclonal in the population of antibodies binding to either peptide 18 or rgp 120, and heterogeneity may have influenced these results. However, the fact that neutralizing sera often had lower avidities than nonneutralizing sera suggests that neutralization does not correlate with higher average avidity to peptide or to recombinant gp 120.

Figure 5A:
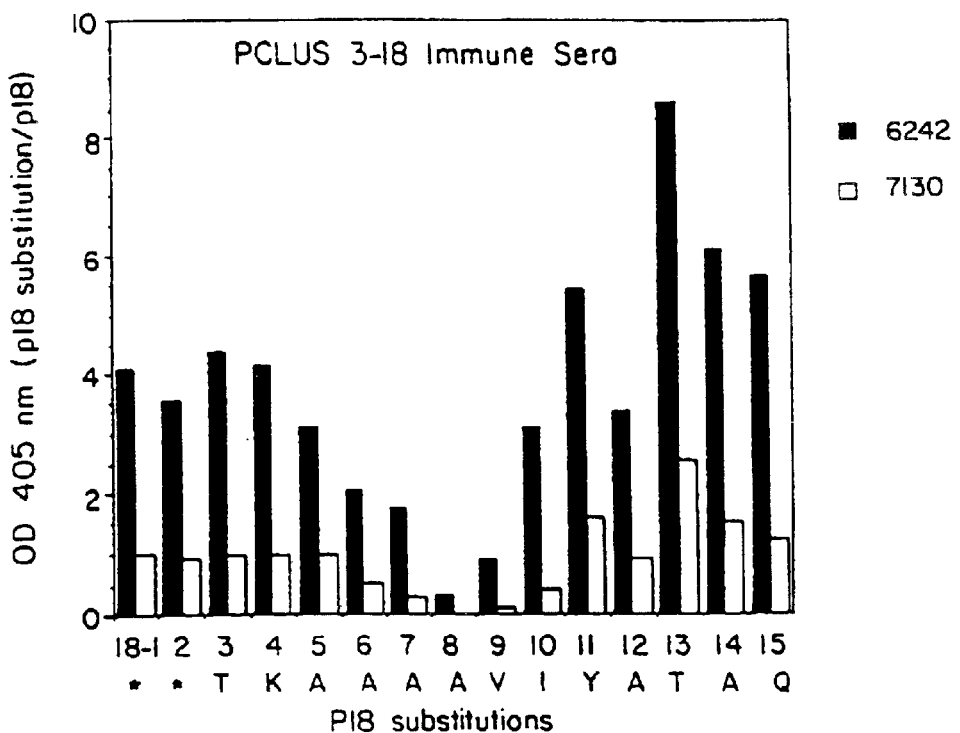
Figure 5B:
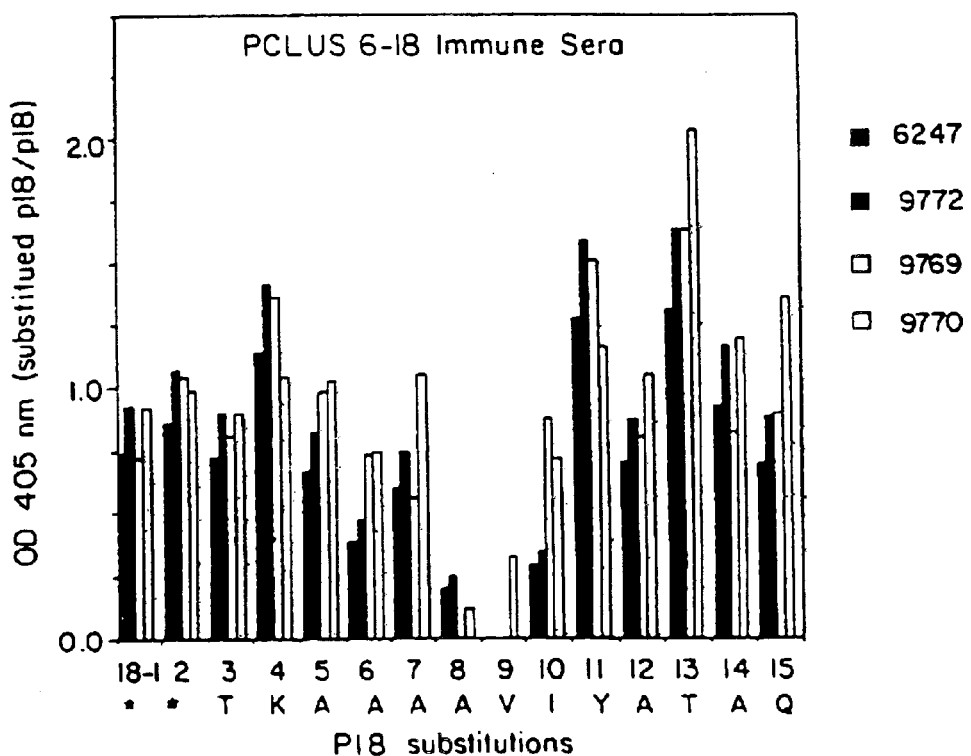

To explore the possibility that fine specificity differences might explain differences in neutralizing activity of sera with comparable peptide binding activity, we used peptides with single amino acid substitutions, in which single residues from the HIV-1-RF sequence replaced residues in the HIV-1-IIIB sequence, (see Table V, SEQ ID NOs:7–23) to test the effect of each residue on the binding of neutralizing and non-neutralizing sera from animals immunized with PCLUS 3-18 and PCLUS 6-18 (FIG. 5).

tions at positions number 12, 13, 14, and 15 revealed a similar enhancement. Binding of both groups of sera was reduced when substitutions were made in the central loop region of the peptide 18 sequence PGRAF. This was not surprising since the sequence GPGR has been shown to be the binding site for neutralizing antibodies and maintains a well defined β-turn conformation (60). It was surprising that a substitution of alanine for glycine at residue 312, (peptide 18-5) did not influence binding. It was also surprising that a substitution of alanine for proline residue 313 (peptide 18-6) did not more completely abrogate binding despite its effect in disrupting the putative reverse turn conformation. The most interesting substitution was substitution position number 8, amino acid residue 315. Neutralizing sera retained binding, albeit significantly less than to unsubstituted peptide 18, to a peptide with an alanine for arginine substitution made at this residue, whereas nonneutralizing sera failed to bind to this substituted peptide. We examined the central loop region further with additional sera. We were able to reproduce this finding in 3 additional experiments. Results from such an experiment are represented in FIG. 6. Both neutralizing and nonneutralizing sera from animals immunized with cluster peptide 3-18 (top panel) showed reduced binding to substitutions made at positions 6, 7, 8, and 9. However, neutralizing sera retained a slight degree of binding to the peptide substituted at position number 8, whereas nonneutralizing sera failed to bind. Similarly in the lower panel, neutralizing and nonneutralizing sera from animals immunized with PCLUS 6-18 showed a dramatic reduction in binding to peptides with substitutions at position 6, 7, 8, and 9. Again, however, neutralizing sera retained a higher level of binding to the peptide with alanine for arginine substituted at position 8. In another experiment, the difference in effect of position 8 between neutralizing and non-neutralizing sera was more marked, although not as many substitutions were tested. The implications of an alanine for arginine substitution at residue 315 are unclear since it is the

TABLE V

Substituted Peptides Used for Determination of Binding Specificity (37)

| | 315 | | | | | | | | | | | | | 329 | |
|---|---|---|---|---|---|---|---|---|---|---|---|---|---|---|---|
| 18IIIB(P18) | R | I | Q | R | G | P | G | R | A | F | V | T | I | G | K |
| 18RF | * | * | T | K | G | P | G | R | V | I | Y | A | T | G | Q |
| 18-1 | * | | | | | | | | | | | | | | |
| 18-2 | | * | | | | | | | | | | | | | |
| 18-3 | | | T | | | | | | | | | | | | |
| 18-4 | | | | K | | | | | | | | | | | |
| 18-5 | | | | | A | | | | | | | | | | |
| 18-6 | | | | | | A | | | | | | | | | |
| 18-7 | | | | | | | A | | | | | | | | |
| 18-8 | | | | | | | | A | | | | | | | |
| 18-9 | | | | | | | | | V | | | | | | |
| 18-10 | | | | | | | | | | I | | | | | |
| 18-11 | | | | | | | | | | | Y | | | | |
| 18-12 | | | | | | | | | | | | A | | | |
| 18-13 | | | | | | | | | | | | | T | | |
| 18-14 | | | | | | | | | | | | | | A | |
| 18-15 | | | | | | | | | | | | | | | Q |

*Indicates a deletion
‡ The underlined amino acids are substitutions in the 18 IIIB sequence.

Substitutions at neither the amino nor the carboxy-terminus of peptide 18 seemed to affect binding by either neutralizing sera, represented by the solid columns, or nonneutralizing sera, represented by the open columns, from animals immunized with PCLUS 3-18 or PCLUS 6-18. In fact, binding was enhanced over peptide 18 control when a tyrosine was substituted for a valine at position number 11 and substituneutralizing sera which retain modest binding. However this result combined with the slightly greater effect of substitutions at positions 6 and 7 on binding of neutralizing sera than nonneutralizing sera suggests that neutralizing sera may be more focused on the tip of the loop, and non-neutralizing more focused on the carboxyl side adjacent to the central loop. Thus, a subtle difference in fine specificity may explain the difference in neutralizing activity among sera with comparable peptide and gp 120 binding activity.

This study demonstrates the utility of combining neutralizing B cell epitopes with a cluster of immunodominant T-helper sites for the purpose of constructing synthetic peptide vaccines with enhanced immunogenicity in multiple MHC types. The T-helper sites chosen for this study encompass multideterminant regions of the HIV envelope protein gp160 previously shown to be recognized by mice of multiple H-2 types as well as human T cells from HIV-infected patients representing a broad array of HLA types. Our strategy was to link each cluster peptide to a short synthetic peptide (peptide 18), previously identified to be an immunodominant site recognized by CD8 cytotoxic T cells in association with class I molecules, and found within the V3 loop or principal neutralizing determinant region of the HIV-IIIB envelope protein. These constructs, PCLUS 3-18, PCLUS 4-18, and PCLUS 6-18 (Table I) all elicited peptide 18 specific antibodies capable of binding rgp120 following a single immunization. Antibodies from mice representing four different MHC haplotypes immunized with one of these constructs, PCLUS 6-18, were capable of neutralizing virus. In 24 of 35 (69%) of the total animals of all strains immunized with PCLUS 6-18, antibodies elicited following a single immunization inhibited the infectivity of the homologous virus by greater 90%. In three of the strains tested PCLUS 6-18 elicited neutralizing antibody in 80–90% of the animals showing a peptide-18 specific response by ELISA. It is interesting to note that in one experiment the reciprocal geometric mean neutralizing antibody titer achieved in two haplotypes of mice, 42.2 in H-$2^d$ and 32.0 in H-$2^k$, was a level approaching the levels known to be protective against an intravenous virus challenge in chimpanzees (30). This mean value is a low estimate since a number of animals in each group had neutralizing titers greater than 64, which was the highest dilution tested. Moreover, a single boost resulted in 90% neutralization titers of 1:1000 to 1:16,000, much higher than seen in our experience with any other immunization protocol (8,59). PCLUS 3-18 elicited peptide specific antibody in all strains tested, but only in animals of the H-$2^d$ haplotype were these antibodies consistently neutralizing (nine of ten mice).

The level of antibody binding activity by ELISA to either peptide 18 or rgp 120 was not predictive of whether or not antibodies elicited by the cluster peptide-peptide 18 construct would be neutralizing. This suggests that other factors, in addition to the level of T cell help enhancing the magnitude of the antibody response influence the qualitative response to the construct. In order to investigate the mechanism resulting in marked differences in neutralizing activity among sera with comparable peptide 18 binding activity by ELISA, we compared the specificity, affinity, and isotype of the antibodies. Interestingly, all sera that contained peptide 18 specific antibodies also contained high levels of antibodies that bound to envelope protein rgp 120 even though animals were immunized with peptide. This finding suggest that the preferred conformation of the short synthetic sequence of peptide 18 mimics to some degree that of the corresponding region in the larger envelope protein. Although 3 of 5 neutralizing sera tested from animals immunized with PCLUS 6-peptide 18 bound virus infected cells expressing native gp120 in an IFA assay, we could not find any correlation between neutralization titer and binding by IFA. Furthermore, contrary to expectation, neutralizing sera exhibited slightly lower binding avidities to rgp 120 than nonneutralizing sera. Clearly other factors, in addition to the magnitude and affinity of binding to the V3 loop of gp120, influence neutralization.

To investigate this we looked for differences in isotype and fine specificity. No isotype differences were found. Both neutralizing and nonneutralizing sera showed reduced binding to substitutions in the central loop region of peptide 18 (PGRAF), although results suggested that neutralizing sera may be more focused on the tip of the loop, and nonneutralizing antibodies more focused on the carboxyl side adjacent to the central loop, in agreement with the experience of Javaherian et al.(61).

Results in this study are compatible with previous results in which a synthetic vaccine was made by coupling a T helper site, T1 peptide residues 421–436, to a longer peptide called SP10, residues 296–314 located within the V3 loop (62,63). Animals immunized with this construct developed both proliferative responses to the gp 120 envelope protein and neutralizing antibody after a series of immunizations employing different immunization regimens. T1 is contained within PCLUS 3, but does not represent a multideterminant region, and SP10 overlaps peptide 18 but lacks eight residues toward the carboxyl terminus of the central loop. Although the V3 loop is not the only site on the viral envelope that elicits neutralizing antibodies (64–67), it appears to be the major one that can be defined by a linear peptide sequence and against which antibodies can neutralize virus after it has bound its cellular receptor, the CD4 molecule (24,61,68,69).

The hypervariability of this region raises questions about how many variants of this sequence must be included in a vaccine. PCR studies of virus from North American and European isolates suggest that there is a consensus sequence that is relatively conserved that is most like the MN or SC isolates (24). In another independent study of infected individuals in North America and Europe, the majority of those tested were shown to possess antibody reactive with an MN-like variant of the V3 loop (70,71). A relatively conserved portion of the loop, GPGRAF, has been shown to elicit antibodies that neutralize four of seven isolates of HIV tested (61). Isolate-specific neutralization is commonly found. The presence of neutralization escape mutants in infected patients may involve sequence variation within the V3 loop itself as well as sequence variation outside the loop leading to conformational changes (33,72). It is likely that a synthetic peptide vaccine must contain multiple constructs containing divergent V3 loop peptides that produce neutralizing antibodies of the right conformational specificity to a large number of transmitting isolates.

We have also shown in this study that a booster immunization with PCLUS 6-18 given up to 49 weeks post vaccination leads to a response 2.5–10 times the magnitude of the initial response by ELISA. Strikingly this rise in antibody levels correlates with an even higher rise in neutralization titers up to 1:1000 to 1:16,000 for 90% neutralization, and even higher for 50% neutralization (FIG. 3 and Table IV). Lower titered crossreactivity on the MN isolate was also observed. At five months following the boost, antibody titers to P18 as measured by ELISA have remained at a high plateau.

An important question was to determine if immunization with PCLUS 3-18 or 6-18 elicited antibodies that were directed to the T helper sites themselves. It is unlikely that antibodies directed to T helper sites would block the T cell receptor from recognizing the site presented by the antigen presenting cell, because antibody directed to whole proteins has previously been shown to enhance uptake of the molecule and presentation to T cells, and it has usually not been possible to block presentation of antigen to T helper cells by anti-peptide antibodies directed to a T cell epitope (73–76), although exceptions have been reported (77,78). We did not observe any diminution of response in animals immunized with cluster peptide 6-18 following a single boost 36–52 weeks post vaccination even though we have demonstrated that some antibodies are elicited to the T helper region of this construct. Another potential concern is antibody mediated antibody enhancement of viral infectivity, mediated via the Fc receptor and complement receptor (16,79). It is presently unclear to which site(s) enhancing antibodies are elicited during the natural infection, although some have been found to bind to the N-terminal portion of gp 41 (11,79). Antibodies to the region included in PCLUS 3 have not been found to enhance infectivity. Cluster peptide 6 is located within the intracytoplasmic gp41 region of the virus envelope protein and therefore should be less likely to be either enhancing or neutralizing. Finally, we think it unlikely that much of the neutralizing acitvity was directed against the helper cluster peptides, for two reasons. First, we could not detect antibodies to PCLUS 3 by ELISA in the neutralizing sera from animals immunized with the PCLUS3-18 construct. In animals immunized with PCLUS6-18, some antibodies were detected to PCLUS 6, but since these are directed to the intracytoplasmic tail of gp41 which is not believed to be exposed on the virion, it is unlikely that they could neutralize virus. Second, antibodies to either PCLUS 3 or PCLUS 6, if neutralizing, would be expected to cross-neutralize the MN strain of HIV-1, since these regions are relatively conserved compared to the P18 region, against which neutralizing antibodies are generally type-specific. Thus, the lack of cross-neutralization (Table III) indicates that the neutralizing activity is directed primarily against P18 and not the helper sites. In addition, antibodies to the T1 peptide, which represents a major portion of the PCLUS 3 peptide, were found not to correlate with neutralization in another study (80).

EXAMPLE II

Immunization of Mice to Elicit CTL Against HIV-1

Since HIV can spread via cell to cell transmission, the ability to elicit a viral specific CTL response might be important for a synthetic peptide vaccine in order to be an effective modality of immunotherapy.

The peptides described in Example I contain a CTL epitope in addition to a Th epitope and PND. Thus, the peptides were also tested for induction of CTL activity in mice.

Here, we address the question with a single immunization using a saponin adjuvant, QS21 (103), which does not require an emulsion, allowing us to test the requirement for covalent linkage between helper and CTL epitopes under limiting conditions. We also addressed the MHC linkage of helper activity by using congenic mouse strains differing in class II MHC but sharing the H-2D$^d$ class I molecule presenting the CTL determinant.

We have previously described the construction of synthetic peptides encompassing immunodominant Th peptides spanning multideterminant regions (54) from the HIV envelope protein gp160 (42). These so-called cluster peptides, each consisting of a cluster of overlapping determinants, were found to induce in vitro T cell proliferation and cytokine production in mice and humans of multiple MHC types, respectively (42). Three cluster peptides were used in the current study: PCLUS3 (residues 421–444, KQIINMWQEVGKAMYAPPISGQIR, SEQ ID NO:24), PCLUS4 (residues 476–499, RDNWRSELYKYKVVKIEPLGVAPT, SEQ ID NO:25), and PCLUS6 (residues 821–853, AVAEGTDRVIEVVQGAYRAIRHPRRIRQGLER, SEQ ID NO:26), in which the HIV-1 IIIB numbering system is according to the Los Alamos database (43) (7 less than that of Ratner et al. (44) used in previous publications (42)).

To design a peptide vaccine immunogenic in multiple MHC types and to investigate the mechanisms of CTL priming in vivo, we co-linearly synthesized each of the cluster peptides at the N-terminus of an immunodominant CTL determinant, P18 (45) (residues 308–322, RIQRGPGRAFVTIGK, SEQ ID NO:7), previously identified to be recognized by murine CD8$^+$ CTL of four distinct MHC types (104) as well as human T cells from HIV-infected patients representing a broad array of HLA types (46). The P18 peptide corresponds to part of the gp160 V3 loop and principal neutralizing determinant (PND)) region of gp160 (21–23), and is also presented by a class II MHC molecule (I-A$^d$) to helper T cells in mice of appropriate MHC type (105).

The cluster peptide-peptide-18 constructs were synthesized on an automated peptide synthesizer (Model.430A; Applied Biosystems, Foster City, Calif.) utilizing t-boc chemistry (51). The peptides were cleaved from the resin with HF and initially purified by size exclusion chromatography. Purification to single peaks was achieved by reverse-phase HPLC on μbondapack reverse-phase C18 columns (Waters Associates, Milford, Mass.). Mice 8–20 weeks old were immunized subcutaneously at the tail base with 20 nmoles of each peptide mixed with QS21 (15 μg), the highly purified saponin fraction from the soap bark tree Quillaja saponaria, which retains the greatest adjuvant activity but is non-toxic (103). Two weeks after a single immunization, immune spleen cells from B10.D2 (H-2$^d$) (FIG. 7A), B10.A (5R) (H-2$^{f5}$) (FIG. 7B), or B10.S(9R) (H-2$^{t4}$) (FIG. 7C) mice (5×10$^6$/ml in 24-well culture plates in complete T cell medium (1:1 mixture of RPMI 1640 and EHAA medium containing 10% FCS, 2 mM L-glutamine, 100 U/ml penicillin, 100 μg/ml streptomycin, and 5×10$^{-5}$ M 2-ME)) were restimulated for 6 days in vitro with 0.1 μM of P18 and 10% Con A supernatant-containing medium (Rat T stim; Collaborative Research, Inc., Bedford, Mass.). Cytolytic activity of in vitro secondary CTL was measured as described previously (104) using a 6 hr. assay with $^{51}$Cr-labeled targets. The fibroblast targets were BALB/c.3T3 transfectants (H-2$^d$, class I MHC$^+$, class II MHC$^-$) expressing the whole gp160 protein endogenously (cell line 15-12 (ref (45)). Similar results were obtained with control BALB/c 3T3 cells transfected with only the neomycin resistance gene (18neo cells) pulsed with 1 μM P18 (data not shown). As a control for both gp160 transfectants and peptide-pulsed 18neo cells, background lysis using unpulsed 18neo target cells in the absence of specific peptide was less than 8%. Effectors were cocultured with peptide-pulsed targets at the indicated E:T ratios. The percent of specific $^{51}$CR release was calculated as 100×((experimental release–spontaneous release)/(maximum release–spontaneous release)). Maximum release was determined from supernatants of cells that were lysed by the addition of 5% Triton X-100. Spontaneous release was determined from targets cells incubated without added effectors cells. The assay was performed in triplicate, with 5000 target cells per well.

Thus, mice of three haplotypes, B10.D2 (H-2$^d$; A$^d$E$^d$), B10.A(5R) (H-2$^{f5}$; A$^b$E$^{b/k}$), and B10.S(9R) (H-2$^{t4}$; A$^s$E$^{s/d}$), differing in class II but sharing the class I D$^d$ molecule, were immunized once subcutaneously at the tail base with purified saponin (QS21) containing the compound peptides, PCLUS3-18, PCLUS4-18, or PCLUS6-18, or P18 alone. When their immune spleen cells were restimulated in vitro with P18 in the presence of IL2, we obtained CTL that could kill both transfected BALB/c 3T3 fibrobrast targets expressing endogenously the whole gp160 protein (called 15-12; ref (45)) (FIG. 7) but not control BALB/c 3T3 fibrobrast targets (called 18neo, transfected with the neomycin resistance gene alone). They could also kill the gp160-negative 18neo cells pulsed with peptide P18 (see FIG. 8), evidence that the killing was specific for the P18 moiety. The mice prized in vivo by the compound peptides generated strong CTL activity against 15-12 as well as P18 pulsed targets at effector to target (E:T) ratios as low as 7:1, and reaching levels of 45–75% specific lysis at E:T ratios of 60:1 (FIG. 7A,B,C). In contrast, mice immunized with P18 alone exhibited only marginal CTL activity even at maximal E:T ratios of 60:1. The shift in E:T ratio curves for killing 15-12 targets indicates more than a 10-fold greater number of CTL lytic units in mice primed with the compound peptide compared to mice primed in vivo with P18 alone. Unimmunized mice or mice immunized with adjuvant or peptide alone also failed to give rise to CTL. Also, the cluster peptides without the P18 component failed to prime specific CTL. The finding of markedly diminished or absent CD8+ CTL response to P18 in mice immunized with P18 alone mixed with QS21 raised the possibility that the in vivo priming for P18 specific CTL requires CD4 class II-restricted help and that this help is provided by the immunization with the compound peptide containing cluster Th determinants.

To test whether covalent linkage of the helper determinant to the CTL determinant was required to prime mice in vivo for a CTL response, or whether a mixture of peptides not covalently linked was sufficient, we immunized B10.D2 or B10.A(5R) mice with compound peptides PCLUS3-18 or PCLUS4-18, respectively, or with mixtures of free peptides PCLUS3 or PCLUS4 and P18, or P18 alone in QS21 adjuvant (FIGS. 8A, B). Mice were immunized with PCLUS3-18 or PCLUS4-18, respectively, or mixtures of PCLUS3 or PCLUS4 and P18, or P18 alone, in QS21 adjuvant. Spleen cells from the immunized mice were restimulated for 6 days with 0.1 μM P18 and rIL2 (10 units/ml, Genzyme, Cambridge, Mass.). The effectors were tested on the gp160 transfected line 15-12 (upper panels) or neo-only transfected 3T3 fibroblasts (18neo) pulsed with P18 (1 μM overnight) (lower panels). Background lysis on control 18neo fibroblasts in the absence of peptide was less than 8%. SEM of triplicate wells was less than 7.2% of the mean.

Thus, spleen cells immunized in vivo with the peptides of the present invention were restimulated with P18 and IL-2, which compensates for any deficiency in T-cell help in vitro (since there are no Th cells present in the culture). Cytolytic activity was measured both on the transfected 15-12 fibroblast cell line endogenously expressing gp160, and on control 18neo fibroblasts pulsed with P18 or no peptide. No lysis was observed on the control targets in the absence of peptide. Surprisingly, the CD8+ CTL activity of immune spleen calls from mice immunized with the mixture or P18 alone was negligible, whereas the compound peptide immunization elicited a strong CTL response in both strains (FIG. 8A through FIG. 8B). The lysis of targets pulsed only with P18, taken with the lack of CTL activity against targets pulsed with PCLUS3 or PCLUS4, indicates that the linkage requirement applies to induction of CTL activity specifically against the P18 determinant, and therefore is not due to some other activity that might be induced by the compound peptide and measured on the gp160-expresssing targets. These results indicate that covalent linkage of the cluster peptides as helper sites to the CTL site in the compound peptides PCLUS3-18 and PCLUS4-18 was required for priming of CTL in vivo. This finding was consistently reproducible in three independent experiments.

Because immunization with the compound peptide might prime CD4+ CTL, we determined the phenotype of the specific CTL primed by the peptides. FIG. 9A shows the results when the CTL from B10.D2 and B10.A(5R) mice immunized with 20 nmoles of the compound peptides in 15 μg QS21, after restimulation with 0.1 μM P18 plus rIL-2, were treated with either with anti-CD8 monoclonal antibody (3.155; rat IgM) (114) plus complement (solid bar) or anti-CD4 monoclonal antibody (RL.174; rat IgM) (113) plus complement (open bar), or complement alone (not shown), as described previously (28), and tested on P18 pulsed 18neo as targets.

As shown in FIG. 9A, the CTL were conventional CD8+ CD4− CTL. Also as the targets express only class I, not class II, MHC molecules, the CTL must be restricted by class I MHC molecules. The restriction was mapped to the $D^d$ molecule using L-cells transfected with each $H-2^d$ class I molecule.

In contrast, the helper cells induced by the PCLUS-18 constructs were CD4+, at least as measured in the in vitro stimulation of the immune spleen cells. For example, B10.A (5R) mice were immunized with 20 nmoles of PCLUS4-18, and their spleen cells were treated with or without anti-CD4 (RL 174, reference 113) plus complement before being restimulated for 6 days with PCLUS4-18 or P18 alone in the presence or absence of recombinant IL-2 (rIL-2, 10 U/ml). The resulting effector cells were tested on the gp160-expressing 15-12 BALB/c fibroblast cell line or on neo-only transfected fibroblast cells (not shown) as targets (FIG. 9B). No lysis was observed on the neo-only transfected control targets (less than 4.2%). SEM of triplicate wells was less than 7.3% of the mean. As a control, PCLUS4 alone (not linked to P18) in the presence of IL-2 did not induce any CTL activity. PCLUS4-18, but not P18 alone, stimulated the induction of CTL activity in the absence of rIL-2 to replace help (FIG. 9B). This result suggested that the PCLUS4-18 peptide was eliciting T-cell help in the restimulation culture, making exogenous IL-2 unnecessary. Elimination of CD4+ cells prevented the induction of CTL activity in absence of IL-2, but not in the presence of IL-2 (FIG. 9B). Therefore, the helper cells induced in cultures of cells immune to PCLUS4-18 and restimulated with PCLUS4-18 were CD4-positive. The induction of CTL activity in th cultures of anti-CD4-treated cells in the presence of rIL-2 indicates that the antibody and complement treatment did not affect the CTL precursors themselves. Thus, the CTL precursors, like the CTL effector cells (FIG. 9A) were CD4-negative.

Thus, we have shown a requirement for helper-CTL determinant linkage in vivo for induction of CTL, which had never been demonstrated before for CTL, in contrast to Th-B-cell cooperation, for which a requirement for cognate help in vivo has been widely recognized for many years. This result appears to contrast with two recent studies with mixtures of helper and CTL antigenic peptides, in which covalent linkage was not obligatory (90,102). We may reconcile these findings by suggesting that in the former study (90), cosequestration of the peptides in an adjuvant emulsion kept them physically together in oil microdroplets, and that in the latter study (102), multiple high doses of peptide used were able to overcome the inherent disadvantage of the unlinked mixture. This explanation is consistent with the requirement for proximity or presentation on the same presenting cell demonstrated by the requirement for helper and CTL determinants to be on the same skin graft to induc a rejection response in vivo (89). The explanation is also consistent with our findings in vitro that in the confines of a culture well, a mixture of cluster peptide and P18 is sufficient to elicit a CTL response without added IL-2 almost as efficiently as the covalent construct. The lower dose without adjuvant emulsion may more closely mimic the case in natural infection. As the peptide which induces the strongest CTL response is different from strain to strain (FIG. 7), the enhancement of CTL response by compound peptide cannot be accounted for simply by the effects of the helper site on resistance or susceptibility of the peptide to enzymatic degradation in vivo. Indeed, the reproducible difference in responsiveness to different peptide constructs among congenic recombinant mouse strains differing in class II but sharing the same H-2D$^d$ class I molecule implies that the helper T-cells are class II MHC restricted and that the cluster peptides are not presented equally by all the class II molecules. Nevertheless, the use of the cluster peptides allows much broader helper recognition among mice of different MHC types than would be elicited by single helper determinants (42).

The mechanism of induction of CTL in vivo by compound peptides is likely to be that the longer peptides are taken up by specialized class II-expressing antigen-presenting cells (APC), implicated in CTL induction (100,106,107), probably at the injection site or in draining lymph nodes, before degradation of the peptides by protease in serum or extracellular fluid, so the same cell may present both the CTL and Th epitopes through class I and class II MHC, respectively. This presentation may be more efficient than others in which the two epitopes are presented by the different APC independently. The greater efficiency of presentation by the same APC may be because it brings the helper T cell and the CTL precursor together, for more effective transmission of small quantities of labile lymphokines, or, as suggested by Gill and Lafferty (108), because the APC is activated by the helper cell, and then in turn is more effective at presenting antigen to the CTL. In the former case, the presentation events to both cells would have to be close in time, whereas in the latter case, they could be separated in time. In either case, the same APC would be more efficient than two separate APC, and therefore the linked determinants would be more effective than ones that could diffuse apart once injected in vivo. This is consistent with the recent observation in which specialized APC xpressing class II MHC simultaneously present extracellular antigens through both class I and class II MHC pathways to CTL and Th, respectively (107), and with the skin graft experiments cited earlier (89). QS21 may be able to penetrate cell membrane and introduce antigen into the cytoplasm, from which it can enter the MHC class I presentation pathway (103). Whichever of the above mechanisms holds, the stimulation of both cells by the same APC should facilitate the delivery of help.

Progression of HIV-1 infection toward AIDS appears to correlate with a shift from Th1 to Th2 predominance in the HIV-1 specific cytokine response (109,110). In a previous study from our lab, reduction in CTL response to P18 due to concurrent schistosome infection appeared to correlate with a shift from Th1, producing IL2, to Th2 predominance (111). Th1 cells are thought to provide the CD4$^+$ class II-restricted help for CTL priming, whereas Th2 cells may secrete cytokines that inhibit CTL generation. Therefore, immunization of HIV-1 carriers for immunotherapy should be most effective if it boosts both Th1 CD4$^+$ cells and CTL, as these compound constructs are intended to do.

Help for induction of P18-specific neutralizing antibody was also observed following a single immunization in mice of four different haplotypes with these compound constructs containing cluster peptides (Example I). Although the immunization experiments presented here had to be carried out in experimental animals, the fact that the same epitopes are also recognized by human helper T cell and CTLs with more than one histocompatibility complex (HLA) class II or class I molecule (42,46), suggests that the same approach should be applicable to human immunization. Cluster 3 and 4 have sequences that are relatively conserved among North America and European isolates of HIV-1, and CLUSTER 6 spans the boundary between conserved and variable sequences (43).

Our current results, using recombinant mice differing in class II MHC molecules, suggest that Th determinants must be covalently attached to the CTL determinant on a single peptide to facilitate T—T collaboration and CD4$^+$ class II-restricted help for priming of CTL response in vivo. Also, these cluster peptide-P18 constructs, previously shown to elicit high titers of HIV-neutralizing antibodies (Example I, above) are useful immune constructs to elicit CTL as well as neutralizing antibodies to HIV in individuals of multiple MHC types.

EXAMPLE III

Broad Immune Response Elicited by Cluster Peptides Attached to the P18 Peptide of HIV-1 Variant MN The hypervariability of the V3 loop of the HIV-1 virus raises the concern that vaccines directed to particular amino acid sequences in this region might not provide protection against the broad assortment of strains to which individuals might be exposed. One approach to overcoming the problem of strain variation is to immunize an individual with a preparation which comprises a mixture of several peptides, each directed against a different strain of the target pathogen. In order to assess the efficacy of peptides of the present invention against additional strains of HIV-1, we prepared a series of cluster peptides attached to the P18 peptide derived from the V3 loop of the MN strain of HIV-1.

The peptides were prepared as described in the General Methods above. The sequences of the PCLUS-18 MN peptides are presented in Table VI (SEQ ID NOs:27–33).

$^a$ P18MN portion=RIHIGPGRAFYTTKN (SEQ ID NO:34);

PCLUS1 portion=EQMHEDIISLWDQSLKPCVK (SEQ ID NO:27);

PCLUS3 portion=KQIINMWQEVGKAMYAPPISGQIR (SEQ ID NO:28);

PCLUS4 portion=RDNWRSELYKYKVVKIEPLGVAPT (SEQ ID NO:29);

PCLUS6 portion=AVAEGTDRVIEVVQGAYRAIRHIPRRIRQGLER (SEQ ID NO:30);

PCLUS6.1 portion=DRVIEVVQGAYRAIRHIPRRIRQGLER (SEQ ID NO:31);.

P53 portion=DRVIEVVQGAYRAIR (SEQ ID NO:32);

P55 portion=AQGAYRAIRHIPRRIP (SEQ ID NO:33).

Four strains of mice representing four different haplotypes (See Example I, Table II) were immunized intraperitoneally with 20 nanomoles of P18MN, PCLUS3-18MN or PCLUS6-18MN peptide emulsified in Complete Freund's Adjuvant (CFA) as described in Example I. Seven to eight weeks later, the mice were boosted with a second immunization, again with 20 nmoles i.p., and AbN titers against the HIV-1 strain MN were determined. The results of this experiment are shown in FIG. 10.

In a similar experiment comparing the peptides PCLUS6-18MN and PCLUS6.1-18MN, mice were immunized as described above, but using those peptides. The results of this experiment are shown in FIG. 11.

From these two experiments, it is concluded that PCLUS3-18MN, PCLUS6-18MN and PCLUS6.1-18MN induce levels of AbN with a titer greater than 1:64 in all of the strains of mice tested, except that PCLUS3-18MN does not induce an immune response in BALB/c mice. Thus, the H-$2^d$ haplotype is not responsive to the PCLUS3-18MN peptide.

CTL response to the PCLUS-18MN peptides was investigated using the p18MN and PCLUS3-18MN peptides. Primary immunization of groups of BALB/c mice was performed using 20 nmole of the peptide emulsified 1:1 with one of the following adjuvants: Alum, Incomplete Freund's Adjuvant (IFA), QS 21 (described above), DOTAP (Boehringer Mannheim Biochimica, cat. no. 1202 375; DOTAP is a lipofection reagent for the introducing macromolecules into cells through the plasma membrane.) and C259/763 (C259/763 is a proprietary substance provided by Dr. Fredrick Durr of Lederle Laboratories).

After two to three weeks, the mice were boosted with 10 nmole of peptide and after an additional two to three weeks, spleens from two mice per group were removed and stimulated in vitro, as described in the above Example II. Six days later, the cells were harvested and tested in a conventional cytotoxic T cell assay, again as described in Example II. Results are shown in FIG. 12.

An additional experiment was performed to assess the ability of the PCLUS6-18MN peptide to elicit a CTL response. Immunizations similar to those used above to elicit CTL to PCLUS3-18MN were used, comparing in this second case the responses to P18MN and PCLUS6-18MN and PCLUS6.1-18MN. However, the booster immunization was performed using 20 nmole of peptide and spleen cells were assayed for content of CTL after in vitro stimulation with peptide P18 and IL-2, the latter to provide non-specific help. The results of this experiment are shown in FIG. 13.

As is clearly shown by the CTL experiments, the PCLUS-18MN peptides are more effective in eliciting a CTL response than the P18MN peptide. The CTL response is produced in mice having a broad range of different MHC haplotypes. Furthermore, the superior efficacy of the PCLUS-18MN peptides in producing the CTL response is demonstrable in a variety of adjuvants.

Although the hypervariability of the V3 loop raises concerns for the design of a vaccine aimed at eliciting neutralizing antibodies and CTL specific for this region, it is encouraging that the same constructs with the P18 region from the HIV-1 MN isolate, which is representative of the most prevalent strains in Europe and North America (24,71), were also found to prime in vivo for a CTL response and to elicit a neutralizing antibody response against the MN variant. Also, recently, we found that CTL populations with broad specificities with respect to virus strain could be generated by restimulation of IIIB-gp160 primed murine spleen cells with MN-type peptide with an aliphatic substitution at one position (112).

As demonstrated by the Examples hereinabove, the peptides of the present invention, which elicit efficient linked help for induction of both neutralizing antibodies and CTL in hosts presenting a broad range of MHC haplotypes should be considered as vaccine candidates for prevention or immunotherapy of AIDS. The approach presented here, that is, covalent attachment of epitopes constituting Th epitopes, CTL epitopes and PND for neutralizing antibodies into a single immunogenic polypeptide that is effective in producing all of these immune responses in a plurality of hosts having a broad range of MHC types, can be applied to other pathogens. In particular, it is expected that this approach can be applied to the development of vaccines against other viral pathogens, such as, but not limited to cytomegalovirus, hepatitis viruses, HTLV-I, rabies virus and the like. Furthermore, vaccines against viruses having non-human hosts, such as Feline Leukemia Virus, Feline Immunodeficiency Virus and the like could also be produced using the approach of the present invention.

EXAMPLE IV

Eliciting a Broad Immune Response to Malaria Circumsporozoite Antigen

U.S. Pat. No. 5,028,425 describes the production of a synthetic vaccine directed to the circumsporozoite (CS) protein of Plasmodium falciparum. That vaccine consists of a peptide immunogen which contains a CTL epitope from the CS antigen. U.S. Pat. No. 4,886,782 describes a second synthetic vaccine directed against the CS protein which consists of a Th epitope that is linked to an AbN epitope. Each of these patents is hereby incorporated in their entirety by reference.

In order to make a peptide vaccine which is recognized by a broad range of MGC types that will elicit a Th response, a CTL response and a high titer AbN, a peptide having the sequence PSDKKIEQYLKKIKNSISCNP(NANP)$_5$NAKP KDELDYENDIEKKICKMEKCS (SEQ ID NO:35) is synthesized as described above. The peptide is administered to mice of differing MHC haplotypes (strains B10.D2, BIOA (5R) and B10.S((9R)) as described in Example II. AbN and CTL response is evaluated as described in Examples I and II, respectively.

EXAMPLE V

Clinical Trials in Human Subjects

The peptides of the present invention can be administered to human subjects as either a prophylactic or therapeutic vaccine. Initially, clinical trials to evaluate the safety and maximum tolerated dose are conducted in human patients who are already infected with HIV. Thus, this example describes an experiment which provides preliminary evidence of the efficacy of a vaccine formulation in a therapeutic mode.

The peptides of the present invention can be formulated into pharmaceutical compositions using the well-known materials and methods in the art. For instance, the peptides can be mixed with any sterile, pharmaceutically acceptable carrier solution, e.g. saline, and packaged in syringe bottles for purposes of preparing an injectable preparation.

The dosage of the peptide that is administered can be also be determined by methods known in the pharmaceutical arts. The actual dosages administered will vary depending upon various pharmacokinetic properties of the peptide, including half-life, sequestration by various tissues, route of administration, and the like. Typically, peptide pharmaceuticals are administered in amounts ranging from 0.1 to 50 μg/kg body weight of the subject.

In the clinical trial described herein, the experimental cohort consists of HIV-infected patients, ages 18–75, with $CD4^+$ cell counts of >600 cells/ml. Consideration is given to requiring that the patients entered into the trial should present with evidence of intact T cell immune function, as measured by response to a recall antigen, for example influenza virus, as described in reference 57, in an IL-2 production assay. Patients should be off anti-retroviral therapy during the initial four months of the trial. If, starting 3 months after entry into the trial, $CD4^+$ cell counts fall below 500 cells/ml, and remains so for one month, then standard anti-retroviral therapy will be offered to the patients.

Peptides PCLUS3-18 and PCLUS6.1-18 are administered to patients subcutaneously in Montanide ISA-51 adjuvant in a formulation prepared under GMP standards by Seppic, Inc. (Fairfield, N.J.). Vaccine is administered on day 0, and booster immunizations are given at 1, 3, 6, 9 and 12 months. The following immunization groups are made:

1. 80 μg PCLUS3-18
2. 80 μg PCLUS6.1-18
3. 160 μg PCLUS3-18
4. 160 μg PCLUS6.1-18
5. 80 μg PCLUS3-18+80 μg PCLUS6.1-18
6. 160 μg PCLUS3-18+160 μg PCLUS6.1-18

Patients are first entered into groups 1 and 2, then into groups 3 and 4, then group 5 and finally into group 6. As experience is gained with the administration of the peptide to humans, patients in groups 1–4 might be permitted to receive the combination of PCLUS3-18 and PCLUS6.1-18, after a 6 month regimen of one or the other of the individual peptides.

A variety of immune system parameters is monitored in each patient, including:

routine chemistries and hematologic parameters;
Examination for toxicology and opportunistic infections;
Lymphocyte subsets;
Serum HIV p24 antigen levels;
Serum, plasma and cells are periodically frozen for measurement of viral load; measurement is by assays that are state of the art currently, including PCR-based assays;
Measurement of antibodies specific to the peptides and to other determinants on HIV;
Determination of HIV neutralizing antibody titer;
Cytokine production, including interleukin-2 production, in response to mitogens, alloantigens, common antigens (e.g. influenza) and HIV antigens;
Measurement of CTL activity against HIV antigens;
Skin tests for immune response to antigens other than those employed in testing for cytokine response.

Techniques for each of these assays are routine in the art.

EXAMPLE VI

Use of the Peptides of the Present Invention in Diagnostic Assays

It is of course readily apparent to one of skill in the art that the peptides of the present invention, in addition to having utility as immunogens for eliciting a broad immune response, can also be employed in a diagnostic fashion to assay for antibody and CTL function in a patient.

The basic formats for antibody assays are well-known in the art, among them such solid-phase assays as ELISA, RIA and the like. In such solid-phase assays, the peptide of the present invention is attached to an insoluble substrate and the substrate, with the peptide bound thereto is contacted with a sample to be tested, under conditions such that if specific anti-peptide antibodies are present in the sample, they can bind to the peptide. The bound antibody is then detected by any of a variety of means, which are also well-known in the art. One such detection method employs a second, radiolabelled or enzyme-lablelled antibody which is specific for the Fc region of IgG, for example.

Similarly, measurement of CTL response is well-known. One method for measuring CTL response is described in Example II. Thus, peripheral blood cells from a patient can be incubated with peptides of the present invention and together with a target cell population that comprises a fibroblast cell line expresses MHC molecules which present the peptide of the present invention on their surface. Peptide-specific lysis of the target cells is a measure of CTL function in the patient.

The invention being thus described, it will be apparent to one of skill in the art that various modifications of the materials and methods used to make or practice the invention could be employed. Such modifications are to be considered as encompassed by the scope of the invention as claimed below.

REFERENCES

Throughout this paper, reference is made to a number of articles of scientific and patent literature. Each of such papers are hereby incorporated in their entirety by such reference. Those articles which can be found in the technical literature are listed below:

1. Fauci, A. S., *Science* 239:617 (1988).
2. Lane, H. C., J. M. Depper, W. C. Greene, G. Whalen, T. A. Waldmann, and A. S. Fauci., *New Engl. J. Med.* 313:79 (1985).
3. Redfield, R. R., D. L. Birx, N. Ketter, E. Tramont, V. Polonis, C. Davis, J. F. Brundage, G. Smith, S. Johnson, A. Fowler, T. Wierzba, A. Shafferman, F. Volvovitz, C. Oster, and D. S. Burke, *N. Engl. J. Med.* 324:1677 (1991).
4. Schechter, M. T., K. J. P. Craib, T. N. Le, J. S. G. Montaner, B. Douglas, P. Sestak, B. Willoughby, and M. V. O'Shaughnessy, *AIDS* 4:185 (1990).
5. Dalgleish, A. G., S. Wilson, M. Gompels, C. Ludlam, B. Gazzard, A. M. Coates, and J. Hab shaw, *Lancet* 339:824 (1992).
6. Wendler, I., U. Bienzle, and G. Hunsmann, *AIDS Res. Hu. Retroviruses* 3:157 (1987).
7. Simmonds, P., D. Beatson, R. J. G. Cuthbert, H. Watson, B. Reynolds, J. F. Peutherer, J. V. Parry, C. A. Ludlam, and C. M. Steel, *Lancet* 338:1159 (1991).
8. Nara, P. L., R. R. Garrity, and J. Goudsmit, *FASEB J.* 5:2437 (1991).
9. Nara, P. L. and J. Goudsmit, "Clonal dominance of the neutralizing response to the HIV-1 V3 epitope: 'Evidence for "original antigenic sin' during vaccination and infection in animals, including humans." In *Vaccines* 91. R. M. Channock, H. Ginsberg, F. Brown and R. A. Lerner, eds. Cold Spring Harbor Laboratory Press, Cold Spring Harbor, p. 37 (1991). p1 10. Kohler, H., J. Goudsmit, and P. Nara, *J. Acq. Immune Defic. Syndromes* 5:1158 (1992).
11. Robinson, W. E.,Jr., T. Kawamura, M. K. Gorny, D. Lake, J. -Y. Xu, Y. Matsumoto, T. Sugano, Y. Masuho, W. M. Mitchell, E. Hersh, and S. Zolla-Pazner, *Proc. Natl. Acad. Sci. U.S.A.* 87:3185 (1990).
12. Habeshaw, J. A., A. G. Dalgleish, L. Bountiff, A. L. Newell, D. Wilks, L. C. Walker, and F. Manca, *Immunol. Today* 11:418 (1990).
13. Takeda, A., C. U. Tuazon, and F. A. Ennis, *Science* 242:580 (1988).
14. Robinson, W. E. Jr., D. C. Montefiori, and W. M. Mitchell, *Lancet* 1988:790 (1988).
15. Berman, P. W., T. J. Gregory, L. Riddle, G. R. Nakamura, M. A. Champe, J. P. Porter, F. M. Wurm, R. D. Hershberg, E. K. Cobb, and J. W. Eichberg, *Nature* 345:622 (1990).
16. Homsy, J., M. Meyer, M. Tateno, S. Clarkson, and J. A. Levy, *Science* 244:1357 (1989).
17. Weinhold, K. J., H. K. Lyerly, S. D. Stanley, A. A. Austin, T. J. Matthews, and D. P. Bolognesi, *J. Immunol.* 142:3091 (1989).
18. Siliciano, R. F., L. Trebor, C. Knall, R. W. Karr, P. Berman, T. Gregory, and E. L. Reinherz, *Cell* 54:561 (1988).
19. Golding, H., F. A. Robey, F. T. Gates,III, W. Linder, P. R. Beining, T. Hoffman, and B. Golding, *J. Exp. Med.* 167:914 (1988).
20. Golding, H., G. M. Shearer, K. Hillman, p. Lucas, J. Manischewitz, R. A. Zajac, M. Clerici, R. E. Gress, N. R. Boswell, and B. Golding, *J. Clin. Invest.* 83:1430 (1989).
21. Palker, T. J., M. E. Clark, A. J. Langlois, T. J. Matthews, K. J. Weinhold, R. R. Randall, D. P. Bolognesi, and B. F. Haynes, *Proc. Natl. Acad. Sci. U.S.A.* 85:1932 (1988).
22. Rusche, J. R., K. Javaherian, C. McDanal, J. Petro, D. L. Lynn, R. Grimaila, A. Langlois, R. C. Gallo, L. O. Arthur, P. J. Fischinger, D. P. Bolognesi, S. D. Putney, and T. J. Matthews, *Proc. Natl. Acad. Sci. U.S.A.* 85:3198 (1988).
23. Goudsmit, J., C. Debouck, R. H. Meloen, L. Smit, M. Bakker, D. M. Asher, A. V. Wolff, C. J. Gibbs,Jr., and D. C. Gajdusek, *Proc. Natl. Acad. Sci. U.S.A.* 85:4478 (1988).
24. LaRosa, G. J., J. P. Davide, K. W inhold, J. A. Waterbury, A. T. Profy, J. A. Lewis, A. J. Langlois, G. R. Dreesman, R. N. Boswell, P. Shadduck, L. H. Holley, M. Karplus, D. P. Bolognesi, T. J. Matthews, E. A. Emini, and S. D. Putney, *Science* 249:932 (1990).
25. Steimer, K. S., C. J. Scandella, P. V. Skiles, and N. L. Haigwood, *Science* 254:105 (1991).
26. Javaherian, K., A. J. Langlois, C. McDanal, K. L. Ross, L. I. Eckler, C. L. Jellis, A. T. Profy, J. R. Rusche, D. P. Bolognesi, S. D. Putney, and T. J. Matthews, *Proc. Natl. Acad. Sci. U.S.A.* 86:6768 (1989).
27. Gorny, M. K., A. J. Conley, S. Karwowska, A. Buchbinder, J. -Y. Xu, E. A. Emini, S. Koenig, and S. Zolla-Pazner, *J. Virol.* (1992)
28. Chanh, T. C., G. R. Dreesman, P. Kanda, G. P. Linette, J. T. Sparrow, D. D. Ho, and R. C. Kennedy, *EMBO. J.* 5:3065 (1986).
29. Warren, R. Q., H. Wolf, K. R. Shuler, J. W. Eichberg, R. A. Zajac, R. N. Boswell, P. Kanda, and R. C. Kennedy, *J. Virol.* 64:486 (1990).
30. Girard, M., M. -P. Kieny, A. Pinter, F. Barre-Sinoussi, P. Nara, H. Kolbe, K. Kusumi, A. Chaput, T. Reinhart, E. Muchmore, J. Ronco, M. Kaczorek, E. Gomard, J.- C. Gluckman, and P. N. Fultz, *Proc. Natl. Acad. Sci. U.S.A.* 88:542 (1991).
31. Emini, E. A., P. L. Nara, W. A. Schleif, J. A. Lewis, J. P. Davide, D. R. Lee, J. Kessler, S. Conley, S. Matsushita, S. D. Putney, R. J. Gerety, and J. W. Eichberg, *J. Virol.* 64:3674 ( 1990).
32. Emini, E. A., W. A. Schleif, J. H. Nunberg, A. J. Conley, Y. Eda, S. Tokiyoshi, S. D. Putney, S. Matsushita, K. E. Cobb, C. M. Jett, J. W. Eichberg, and K. K. Murthy, *Nature* 355:728 (1992).
33. Nara, P. L., L. Smit, N. Dunlop, W. Hatch, M. Merges, D. Waters, J. Kelliher, R. C. Gallo, P. J. Fischinger, and J. Goudsmit, *J. Virol.* 64:3779 (1990).
34. Albert, J., B. Abrahamsson, K. Nagy, E. Aurelius, H. Gaines, G. Nyström, and E. M. Fenyo, *AIDS* 4:107 (1990).
35. Reitz, M. S.,Jr., C. Wilson, C. Naugle, R. C. Gallo, and M. Robert-Guroff, *Cell* 54:57 (1990).
36. Takahashi, H., S. Merli, S. D. Putney, R. Houghten, B. Moss, R. N. Germain, and J. A. Berzofsky, *Science* 246:118 (1989).
37. Takahashi, H., R. Houghten, S. D. Putney, D. H. Margulies, B. Moss, R. N. Germain, and J. A. Berzofsky, *J. Exp. Med.* 170:2023 (1989).
38. Saag, M. S., B. H. Hahn, J. Gibbons, Y. Li, E. S. Parks, W. P. Parks, and G. M. Shaw, *Nature* 334:440 (1988).
39. Fisher, A. G., B. Ensoli, D. Looney, A. Rose, R. C. Gallo, M. S. Saags, G. M. Shaw, B. H. Hahn, and F. Wong-Staal, *Nature* 334:444 (1988).
40. Kusumi, K., B. Conway, S. Cunningham, A. Berson, C. Evans, A. K. N. Iversen, D. Colvin, M. V. Gallo, S. Coutre, E. G. Shpaer, D. V. Faulkner, A. DeRonde, S. Volkman, C. Williams, M. S. Hirsch, and J. I. Mullins, *J. Virol.* 66:875 (1992).
41. Boudet, F., M. Girard, J. Theze, and M. Zouali, *Internat. Immunol.* 4:283 (1992).
42. Berzofsky, J. A., C. D. Pendleton, M. Clerici, J. Ahlers, D. R. Lucey, S. D. Putney, and G. M. Shearer, *J. Clin. Invest.* 88:876 (1991).
43. Myers, G., S. F. Josephs, J. A. Berzofsky, A. B. Rabson, T. F. Smith, and F. Wong-Staal, *Human retroviruses and AIDS* 1989. Los Alamos National Laboratory, N. Mex. (1989).
44. Ratner, L., W. Haseltine, R. Patarca, K. J. Livak, B. Starcich, S. F. Josephs, E. R. Doran, J. A. Rafalski, E. A. Whitehorn, K. Baumeister, L. Ivanoff, S. R. Petteway,Jr., M. L. Pearson, J. A. Lautenberger, T. S. Papas, J. Ghrayeb, N. T. Chang, R. C. Gallo, and F. Wong-Staal, *Nature* 313:277 (1985).
45. Takahashi, H., J. Cohen, A. Hosmalin, K. B. Cease, R. Houghten, J. Cornette, C. DeLisi, B. Moss, R. N. Germain, and J. A. Berzofsky, *Proc. Natl. Acad. Sci. USA* 85:3105 (1988).
46. Clerici, M., D. R. Lucey, R. A. Zajac, R. N. Boswell, H. M. Gebel, H. Takahashi, J. Berzofsky, and G. M. Shearer, *J. Immunol.* 146:2214 (1991).
47. Golvano, J., J. J. Lasarte, P. Sarobe, A. Gullón, J. Prieto, and F. Borrás-Cuesta, *Eur. J. Immunol.* 20:2363 (1990).
48. Tindle, R. W., G. J. P. Fernando, J. C. Sterling, and I. H. Frazer, *Proc. Natl. Acad. Sci. USA* 88:5887 (1991).
49. Cox, J. H., J. Ivanyi, D. B. Young, J. R. Lamb, A. D. Syred, and M. J. Francis, *Eur. J. Immunol.* 18:2015 (1988).

50. Berzofsky, J. A., *FASEB J.* 5:2412 (1991).
51. Stewart, J. M. and J. D. Young, *Solid Phase Peptide Synthesis*. Pierce Chemical Company, Rockford, Ill. (1984).
52. Nara, P. L., W. C. Hatch, N. M. Dunlop, W. G. Robey, L. O. Arthur, M. A. Gonda, and P. J. Fischinger, *AIDS Res. Hu. Retroviruses* 3:283 (1987).
53. Hosoi, S., T. Borsos, N. Dunlop, and P. L. Nara, *J. Acq. Immune Defic. Syndromes* 3:366 (1990).
54. Hale, P. M., K. B. Cease, R. A. Houghten, C. Ouyang, S. Putney, K. Javaherian, H. Margalit, J. L. Cornette, J. L. Spouge, C. DeLisi, and J. A. Berzofsky, *Internat. Immunol.* 1:409 (1989).
55. Cease, K. B., H. Margalit, J. L. Cornette, S. D. Putney, W. G. Robey, C. Ouyang, H. Z. Streicher, P. J. Fischinger, R. C. Gallo, C. DeLisi, and J. A. Berzofsky, *Proc. Natl. Acad. Sci. USA* 84:4249 (1987).
56. Berzofsky, J. A., A. Bensussan, K. B. Cease, J. F. Bourge, R. Cheynier, Z. Lurhuma, J. -J. Salaün, R. C. Gallo, G. M. Shearer, and D. Zagury, *Nature* 334:706 (1988).
57. Clerici, M., N. I. Stocks, R. A. Zajac, R. N. Boswell, D. C. Bernstein, D. L. Mann, G. M. Shearer, and J. A. Berzofsky, *Nature* 339:383 (1989).
58. Plata, F., G. Dadaglio, N. Chenciner, A. Hoffenbach, S. Wain-Hobson, F. Michel, and P. Langlade-Demoyen, *Immunodeficiency Reviews* 1:227 (1989).
59. Devash, Y., J. R. Rusche, and P. L. Nara, *Biotech. Therap.* 2:49 (1991).
60. Chandrasekhar, K., A. T. Profy, and H. J. Dyson, *Biochem* 30:9187 (1991).
61. Javaherian, K., A. J. Langlois, G. J. LaRosa, A. T. Profy, D. P. Bolognesi, W. C. Herlihy, S. D. Putney, and T. J. Matthews, *Science* 250:1590 (1990).
62. Palker, T. J., T. J. Matthews, A. Langlois, M. E. Tanner, M. E. Martin, R. M. Scearce, J. E. Kim, J. A. Berzofsky, D. P. Bolognesi, and B. F. Haynes, *J. Immunol.* 142:3612 (1989).
63. Hart, M. K., T. J. Palker, T. J. Matthews, A. J. Langlois, N. W. Lerche, M. E. Martin, R. M. Scearce, C. McDanal, D. P. Bolognesi, and B. F. Haynes, *J. Immunol.* 145:2677 (1990).
64. Profy, A. T., P. A. Salinas, L. I. Eckler, N. M. Dunlop, P. L. Nara, and S. D. Putney, *J. Immunol.* 144:4641 (1990).
65. Broliden, P. -A., A. Von Gegerfelt, P. Clapham, J. Rosen, E. -M. Fenyö, B. Wahren, and K. Broliden, *Proc. Natl. Acad. Sci. USA* 89:461 (1992).
66. Fung, M. S. C., C. R. Y. Sun, W. L. Gordon, R. -S. Liou, T. W. Chang, W. N. C. Sun, E. S. Daar, and D. D. Ho, *J. Virol.* 66:848 (1992).
67. Berkower, I., D. Murphy, C. C. Smith, and G. E. Smith, *J. Virol.* 65:5983 (1991).
68. Nara, P. L., In *Retroviruses of Human AIDS and Related Animal Diseases*. M. Girard and L. Valette, eds. Pasteur Vaccines, Paris, p. 138 (1988).
69. Nara, P. L., In *Vaccines* 89. R. Lerner, H. Ginsberg, M. Channock and F. Brown, eds. Cold Spring Harbor Laboratory, Cold Spring Harbor, p. 137 (1989).
70. Devash, Y., T. J. Matthews, J. E. Drummond, K. Javaherian, D. J. Waters, L. O. Arthur, W. A. Blattner, and J. R. Rusche, *AIDS Res. Hu. Retroviruses* 6:307 (1990).
71. Zwart, G., J. J. De Jong, T. Wolfs, L. Van Der Hoek, L. Smit, A. De Ronde, M. Tersmette, P. Nara, and J. Goudsmit, *Lancet* 335:474 (1990).
72. Nara, P., L. Smit, N. Dunlop, W. Hatch, M. Merges, D. Waters, J. Kelliher, W. Krone, and J. Goudsmit, *Develop. biol. Standard.* 72:315 (1990).
73. Ben-Sasson, S. Z., M. F. Lipscomb, T. F. Tucker, and J. W. Uhr, *J. Immunol.* 119:1493 (1977).
74. Ellner, J. J., P. E. Lipsky, and A. S. Rosenthal, *J. Immunol.* 118:2053 (1977).
75. Glimcher, L. H., J. A. Schroer, C. Chan, and E. M. Shevach, *J. Immunol.* 131:2868 (1983).
76. Shimonkevitz, R., S. Colon, J. W. Kappler, P. Marrack, and H. Grey, *J. Immunol.* 133:2067 (1984).
77. Corradin, G. P., M. A. Juillerat, and H. D. Engers, *J. Immunol.* 133:2915 (1984).
78. Lamb, J. R., E. D. Zanders, P. Lake, R. G. Webster, D. D. Eckels, J. N. Woody, N. Green, R. A. Lerner, and M. Feldmann, *Eur. J. Immunol.* 14:153 (1984).
79. Robinson, W. E. Jr., D. C. Montefiori, W. M. Mitchell, A. M. Prince, H. J. Alter, G. R. Dreesman, and J. W. Eichberg, *Proc. Natl. Acad. Sci. U.S.A.* 86:4710 (1989).
80. Cease, K. B., W. S. Probert, L. M. Groeneveld, N. M. Dunlop, and P. L. Nara, In *Vaccines*92. F. Brown, R. M. Chanock, H. S. Ginsberg and R. A. Lerner, eds. Cold Spring Harbor Laboratory Press, Cold Spring Harbor, p. 201 (1992).
81. R. M. Zinkernagel, P. C. Doherty, *Adv. Immunol.* 27:51 (1979).
82. H. Wagner, A. Starzinski-Powitz, K. Pfizenmaier, M. Rollinghoff, *Nature* 263:235 (1976).
83. R. M. Zinkernagel, G. N. Callahan, A. Althage, S. Cooper, J. W. Streilein, et al, *J. Exp. Med.* 147:897 (1978).
84. H. Von Boehmer, W. Haas, *J. Exp. Med.* 150:1134 (1979).
85. C. J. Melief, M. Y. van der Meulen, B. J. Christiaans, P. de Greeve, *Eur. J. Immunol.* 9:7 (1979).
86. J. A. Keene, J. Forman, *J. Exp. Med.* 155:768 (1982).
87. W. M. Kast, A. M. Bronkhorst, L. P. De Waal, C. J. M. Melief, *J. Exp. Med.* 164:723 (1986).
88. L. A. Husmann, M. J. Bevan, *Ann. N. Y. Acad. Sci.* 532:158 (1988).
89. A. S. Rosenberg, A. Singer, *Ann. Rev. Immunol.* 10:333 (1992).
90. C. Widmann, P. Romero, J. L. Maryanski, G. Corradin, D. Valmori, *J. Immunol. Methods* 155:95 (1992).
91. M. B. Widmer, F. H. Bach, *Nature* 294:750 (1981).
92. H. Von Boehmer, K. Turton, *Eur. J. Immunol.* 13:176 (1983).
93. H. Von Boehmer, P. Kisielow, W. Leiserson, W. Haas, *J. Immunol.* 133:59 (1984).
94. J. Sprent, M. Schaefer, *J. Exp. Med.* 162:2068 (1985).
95. R. M. L. Buller, K. L. Holmes, A. Hügin, T. N. Frederickson, H. C. III Morse, *Nature* 328:77 (1987).
96. K. Deres, H. Schild, K. H. Wiesmüller, G. Jung, H. G. Rammensee, *Nature* 342:561 (1989).
97. P. Aichele, H. Hengartner, R. M. Zinkernagel, M. Schulz, *J. Exp. Med.* 171:1815 (1990).
98. W. K. Kast, L. Roux, J. Curren, H. J. J. Blom, A. C. Voordouw, et al, *Proc. Natl. Acad. Sci. USA* 88:2283 (1991).

99. M. Schulz, R. M. Zinkernagel, H. Hengartner, *Proc. Natl. Acad. Sci. U.S.A.* 88:991 (1991).
100. H. Takahashi, Y. Nakagawa, M. Takeuchi, K. Yokomuro, J. A. Berzofsky, in *Vaccines* 93, F. Brown, R. M. Chanock, H. S. Ginsberg and R. A. Lerner, Eds. (Cold Spring Harbor Laboratory Press, Cold Spring Harbor, 1993),
101. M. K. Hart, K. J. Weinhold, R. M. Scearce, E. M. Washburn, C. A. Clark, et al, *Proc. Natl. Acad. Sci. USA* 88:9448 (1991).
102. J. J. Lasarte, P. Sarobe, A. Gullón, J. Prieto, F. Borrás-Cuesta, *Cellular Immunol.* 141:211 (1992).
103. J. -Y. Wu, B. H. Gardner, C. I. Murphy, J. R. Seals, C. R. Kensil, et al, *J. Immunol.* 148:1519 (1992).
104. M. Shirai, C. D. Pendleton, J. A. Berzofsky, *J. Immunol.* 148:1657 (1992).
105. H. Takahashi, R. N. Germain, B. Moss, J. A. Berzofsky, *J. Exp. Med.* 171:571 (1990).
106. F. R. Carbone, M. J. Bevan, *J. Exp. Med.* 171:377 (1990).
107. K. L. Rock, S. Gamble, L. Rothstein, *Science* 249:918 (1990).
108. R. G. Gill, K. J. Lafferty, *J. Immunol.* 143:4009 (1989).
109. G. M. Shearer, M. Clerici, *Prog. Chem. Immunol.* 54, (1992).
110. M. Clerici, F. T. Hakim, D. J. Venzon, S. Blatt, C. W. Hendrix, et al, *J. Clin. Invest.* 91:759 (1993).
111. J. K. D Actor, M. Shirai, M. C. Kullberg, R. M. L. Buller, A. Sher, et al, *Proc. Natl. Acad. Sci. U.S.A.* 90:948 (1993).
112. H. Takahashi, Y. Nakagawa, C. D. Pendleton, R. A. Houghten, K. Yokomuro, et al, *Science* 255:333 (1992).
113. R. Ceredig, J. W. Lowenthal, M. Nabholz, H. R. MacDonald, *Nature* 314:98 (1985).
114. M. Sarmiento, A. L. Glasebrook, and F. W. Fitch, J. Immunol. 125:2665 (1980).

What is claimed is:

1. An isolated multideterminant co-linear polypeptide consisting of a cluster peptide comprising overlapping T helper epitopes from within HIV envelope protein gp160 and a peptide 18(P18) peptide comprising a cytotoxic T cell epitope and an epitope which elicits a neutralizing antibody response to HIV, wherein said epitopes are located in the third hypervariable region (V3 loop) of the HIV envelope protein gp 160, wherein said cluster peptide is amino terminal to the P18 peptide, and wherein said multideterminant polypeptide can induce a T helper response, a cytotoxic T lymphocyte response and a neutralizing antibody response.

2. The polypeptide of claim 1, wherein said cluster peptide is PCLUS1 (amino acid residues 1–20 of SEQ ID NO:27), PCLUS3 (amino acid residues 1–24 of SEQ ID NO:28), PCLUS4 (amino acid residues 1–24 of SEQ ID NO:29), PCLUS6 (amino acid residues 1–33 of SEQ ID NO:30) or PCLUS6.1 (amino acid residues 1–27 of SEQ ID NO:31).

3. A polypeptide according to claim 1, wherein said P18 peptide is derived from HIV-1 gp160.

4. The polypeptide of claim 1, wherein said P18 peptide has the amino acid sequence SITKGPGRVIYATGQ (SEQ ID NO:37); SIHIGPGRAFYATGD (SEQ ID NO:38); SLSIGPGRAFRTREI (SEQ ID NO:39); SISIGPGRAFFATTID (SEQ ID NO:40); SIYIGPGRAFHTTGR (SEQ ID NO:41); GIAIGPGRTLYAREK (SEQ ID NO:42); RVTLGPGRVWYTTGE (SEQ ID NO:43); SIRIGPGKVFTAKGG (SEQ ID NO:44); GIHFGPGQALYTTGI (SEQ ID NO:45); STPIGLGQALYTTRG (SEQ ID NO:46); STPIGLGQALYTTRI (SEQ ID NO:47); or RTPTGLGQSLYTTRS (SEQ ID NO:48).

5. An immunogenic composition comprising a polypeptide of claim 1 in a pharmaceutically acceptable carrier.

6. A method for eliciting, in a mouse or a human, an antigen specific cytotoxic T lymphocyte response and an antigen specific high titer neutralizing antibody response comprising administering to said mammal mouse or human as the antigen a polypeptide of claim 1 in a pharmaceutically acceptable carrier.

7. The polypeptide of claim 2, wherein said P18 peptide has the amino acid sequence SITKGPGRVIYATGQ (SEQ ID NO:37); SIHIGPGRAFYATGD (SEQ ID NO:38); SLSIGPGRAFRTREI (SEQ ID NO:39); SISIGPGRAFFATTID (SEQ ID NO:40); SIYIGPGRAFHTTGR (SEQ ID NO:41); GIAIGPGRTLYAREK (SEQ ID NO:42); RVTLGPGRVWYTTGE (SEQ ID NO:43); SIRIGPGKVFTAKGG (SEQ ID NO:44); GIHFGPGQALYTTGI (SEQ ID NO:45); STPIGLGQALYTTRG (SEQ ID NO:46); STPIGLGQALYTTRI (SEQ ID NO:47); or RTPTGLGQSLYTTRS (SEQ ID NO:48).

* * * * *

SEQUENCE LISTING

<160> NUMBER OF SEQ ID NOS: 47

<210> SEQ ID NO 1
<211> LENGTH: 35
<212> TYPE: PRT
<213> ORGANISM: HIV-1

<400> SEQUENCE: 1

Glu Gln Met His Glu Asp Ile Ile Ser Leu Trp Asp Gln Ser Leu Lys
1               5                   10                  15

Pro Cys Val Lys Arg Ile Gln Arg Gly Pro Gly Arg Ala Phe Val Thr
            20                  25                  30

Ile Gly Lys
        35

<210> SEQ ID NO 2
<211> LENGTH: 39
<212> TYPE: PRT
<213> ORGANISM: HIV-1

<400> SEQUENCE: 2

Lys Gln Ile Ile Asn Met Trp Gln Glu Val Gly Lys Ala Met Tyr Ala
1               5                   10                  15

Pro Pro Ile Ser Gly Gln Ile Arg Arg Ile Gln Arg Gly Pro Gly Arg
            20                  25                  30

Ala Phe Val Thr Ile Gly Lys
        35

<210> SEQ ID NO 3
<211> LENGTH: 39
<212> TYPE: PRT
<213> ORGANISM: HIV-1

<400> SEQUENCE: 3

Arg Asp Asn Trp Arg Ser Glu Leu Tyr Lys Tyr Lys Val Val Lys Ile
1               5                   10                  15

Glu Pro Leu Gly Val Ala Pro Thr Arg Ile Gln Arg Gly Pro Gly Arg
            20                  25                  30

Ala Phe Val Thr Ile Gly Lys
        35

```
<210> SEQ ID NO 4
<211> LENGTH: 48
<212> TYPE: PRT
<213> ORGANISM: HIV-1

<400> SEQUENCE: 4

Ala Val Ala Glu Gly Thr Asp Arg Val Ile Glu Val Val Gln Gly Ala
1               5                   10                  15

Tyr Arg Ala Ile Arg His Ile Pro Arg Arg Ile Arg Gln Gly Leu Glu
            20                  25                  30

Arg Arg Ile Gln Arg Gly Pro Gly Arg Ala Pro Val Thr Ile Gly Lys
        35                  40                  45

<210> SEQ ID NO 5
<211> LENGTH: 30
<212> TYPE: PRT
<213> ORGANISM: HIV-1

<400> SEQUENCE: 5

Asp Arg Val Ile Glu Val Val Gln Gly Ala Tyr Arg Ala Ile Arg Arg
1               5                   10                  15

Ile Gln Arg Gly Pro Gly Arg Ala Phe Val Thr Ile Gly Lys
            20                  25                  30

<210> SEQ ID NO 6
<211> LENGTH: 31
<212> TYPE: PRT
<213> ORGANISM: HIV-1

<400> SEQUENCE: 6

Ala Gln Gly Ala Tyr Arg Ala Ile Arg His Ile Pro Arg Arg Ile Arg
1               5                   10                  15

Arg Ile Gln Arg Gly Pro Gly Arg Ala Phe Val Thr Ile Gly Lys
            20                  25                  30

<210> SEQ ID NO 7
<211> LENGTH: 15
<212> TYPE: PRT
<213> ORGANISM: HIV-1

<400> SEQUENCE: 7

Arg Ile Gln Arg Gly Pro Gly Arg Ala Phe Val Thr Ile Gly Lys
1               5                   10                  15

<210> SEQ ID NO 8
<211> LENGTH: 13
<212> TYPE: PRT
<213> ORGANISM: HIV-1

<400> SEQUENCE: 8

Thr Lys Gly Pro Gly Arg Val Ile Tyr Ala Thr Gly Gln
1               5                   10

<210> SEQ ID NO 9
<211> LENGTH: 14
<212> TYPE: PRT
<213> ORGANISM: HIV-1

<400> SEQUENCE: 9

Ile Gln Arg Gly Pro Gly Arg Ala Phe Val Thr Ile Gly Lys
1               5                   10
```

-continued

<210> SEQ ID NO 10
<211> LENGTH: 14
<212> TYPE: PRT
<213> ORGANISM: HIV-1

<400> SEQUENCE: 10

Arg Gln Arg Gly Pro Gly Arg Ala Phe Val Thr Ile Gly Lys
1               5                   10

<210> SEQ ID NO 11
<211> LENGTH: 15
<212> TYPE: PRT
<213> ORGANISM: HIV-1

<400> SEQUENCE: 11

Arg Ile Thr Arg Gly Pro Gly Arg Ala Phe Val Thr Ile Gly Lys
1               5                   10                  15

<210> SEQ ID NO 12
<211> LENGTH: 15
<212> TYPE: PRT
<213> ORGANISM: HIV-1

<400> SEQUENCE: 12

Arg Ile Gln Lys Gly Pro Gly Arg Ala Phe Val Thr Ile Gly Lys
1               5                   10                  15

<210> SEQ ID NO 13
<211> LENGTH: 15
<212> TYPE: PRT
<213> ORGANISM: HIV-1

<400> SEQUENCE: 13

Arg Ile Gln Arg Ala Pro Gly Arg Ala Phe Val Thr Ile Gly Lys
1               5                   10                  15

<210> SEQ ID NO 14
<211> LENGTH: 15
<212> TYPE: PRT
<213> ORGANISM: HIV-1

<400> SEQUENCE: 14

Arg Ile Gln Arg Gly Ala Gly Arg Ala Phe Val Thr Ile Gly Lys
1               5                   10                  15

<210> SEQ ID NO 15
<211> LENGTH: 15
<212> TYPE: PRT
<213> ORGANISM: HIV-1

<400> SEQUENCE: 15

Arg Ile Gln Arg Gly Pro Ala Arg Ala Phe Val Thr Ile Gly Lys
1               5                   10                  15

<210> SEQ ID NO 16
<211> LENGTH: 15
<212> TYPE: PRT
<213> ORGANISM: HIV-1

<400> SEQUENCE: 16

Arg Ile Gln Arg Gly Pro Gly Ala Ala Phe Val Thr Ile Gly Lys
1               5                   10                  15

<210> SEQ ID NO 17

<211> LENGTH: 15
<212> TYPE: PRT
<213> ORGANISM: HIV-1

<400> SEQUENCE: 17

Arg Ile Gln Arg Gly Pro Gly Arg Val Phe Val Thr Ile Gly Lys
1               5                   10                  15

<210> SEQ ID NO 18
<211> LENGTH: 15
<212> TYPE: PRT
<213> ORGANISM: HIV-1

<400> SEQUENCE: 18

Arg Ile Gln Arg Gly Pro Gly Arg Ala Ile Val Thr Ile Gly Lys
1               5                   10                  15

<210> SEQ ID NO 19
<211> LENGTH: 15
<212> TYPE: PRT
<213> ORGANISM: HIV-1

<400> SEQUENCE: 19

Arg Ile Gln Arg Gly Pro Gly Arg Ala Phe Tyr Thr Ile Gly Lys
1               5                   10                  15

<210> SEQ ID NO 20
<211> LENGTH: 15
<212> TYPE: PRT
<213> ORGANISM: HIV-1

<400> SEQUENCE: 20

Arg Ile Gln Arg Gly Pro Gly Arg Ala Phe Val Ala Ile Gly Lys
1               5                   10                  15

<210> SEQ ID NO 21
<211> LENGTH: 15
<212> TYPE: PRT
<213> ORGANISM: HIV-1

<400> SEQUENCE: 21

Arg Ile Gln Arg Gly Pro Gly Arg Ala Phe Val Thr Thr Gly Lys
1               5                   10                  15

<210> SEQ ID NO 22
<211> LENGTH: 15
<212> TYPE: PRT
<213> ORGANISM: HIV-1

<400> SEQUENCE: 22

Arg Ile Gln Arg Gly Pro Gly Arg Ala Phe Val Thr Ile Ala Lys
1               5                   10                  15

<210> SEQ ID NO 23
<211> LENGTH: 15
<212> TYPE: PRT
<213> ORGANISM: HIV-1

<400> SEQUENCE: 23

Arg Ile Gln Arg Gly Pro Gly Arg Ala Phe Val Thr Ile Gly Gln
1               5                   10                  15

<210> SEQ ID NO 24
<211> LENGTH: 24
<212> TYPE: PRT

<213> ORGANISM: HIV-1

<400> SEQUENCE: 24

Lys Gln Ile Ile Asn Met Trp Gln Glu Val Gly Lys Ala Met Tyr Ala
1               5                   10                  15

Pro Pro Ile Ser Gly Gln Ile Arg
            20

<210> SEQ ID NO 25
<211> LENGTH: 25
<212> TYPE: PRT
<213> ORGANISM: HIV-1

<400> SEQUENCE: 25

Arg Asp Asn Trp Arg Ser Glu Leu Tyr Lys Tyr Lys Val Val Lys Ile
1               5                   10                  15

Glu Pro Leu Gly Gly Val Val Pro Thr
            20                  25

<210> SEQ ID NO 26
<211> LENGTH: 33
<212> TYPE: PRT
<213> ORGANISM: HIV-1

<400> SEQUENCE: 26

Ala Val Ala Glu Gly Thr Asp Arg Val Ile Glu Val Val Gln Gly Ala
1               5                   10                  15

Tyr Arg Ala Ile Arg His Ile Pro Arg Arg Ile Arg Gln Gly Leu Glu
            20                  25                  30

Arg

<210> SEQ ID NO 27
<211> LENGTH: 35
<212> TYPE: PRT
<213> ORGANISM: HIV-1

<400> SEQUENCE: 27

Glu Gln Met His Glu Asp Ile Ile Ser Leu Trp Asp Gln Ser Leu Lys
1               5                   10                  15

Pro Cys Val Lys Arg Ile His Ile Gly Pro Gly Arg Ala Phe Tyr Thr
            20                  25                  30

Thr Lys Asn
        35

<210> SEQ ID NO 28
<211> LENGTH: 39
<212> TYPE: PRT
<213> ORGANISM: HIV-1

<400> SEQUENCE: 28

Lys Gln Ile Ile Asn Met Trp Gln Glu Val Gly Lys Ala Met Tyr Ala
1               5                   10                  15

Pro Pro Ile Ser Gly Gln Ile Arg Ile His Ile Gly Pro Gly Arg
            20                  25                  30

Ala Phe Tyr Thr Thr Lys Asn
        35

<210> SEQ ID NO 29
<211> LENGTH: 39
<212> TYPE: PRT
<213> ORGANISM: HIV-1

```
<400> SEQUENCE: 29

Arg Asp Asn Trp Arg Ser Glu Leu Tyr Lys Tyr Lys Val Val Lys Ile
1               5                   10                  15

Glu Pro Leu Gly Val Ala Pro Thr Arg Ile His Ile Gly Pro Gly Arg
                20                  25                  30

Ala Phe Tyr Thr Thr Lys Asn
            35

<210> SEQ ID NO 30
<211> LENGTH: 48
<212> TYPE: PRT
<213> ORGANISM: HIV-1

<400> SEQUENCE: 30

Ala Val Ala Glu Gly Thr Asp Arg Val Ile Glu Val Val Gln Gly Ala
1               5                   10                  15

Tyr Arg Ala Ile Arg His Ile Pro Arg Arg Ile Arg Gln Gly Leu Glu
                20                  25                  30

Arg Arg Ile His Ile Gly Pro Gly Arg Ala Phe Tyr Thr Thr Lys Asn
            35                  40                  45

<210> SEQ ID NO 31
<211> LENGTH: 42
<212> TYPE: PRT
<213> ORGANISM: HIV-1

<400> SEQUENCE: 31

Asp Arg Val Ile Glu Val Val Gln Gly Ala Tyr Arg Ala Ile Arg His
1               5                   10                  15

Ile Pro Arg Arg Ile Arg Gln Gly Leu Glu Arg Arg Ile His Ile Gly
                20                  25                  30

Pro Gly Arg Ala Phe Tyr Thr Thr Lys Asn
            35                  40

<210> SEQ ID NO 32
<211> LENGTH: 30
<212> TYPE: PRT
<213> ORGANISM: HIV-1

<400> SEQUENCE: 32

Asp Arg Val Ile Glu Val Val Gln Gly Ala Tyr Arg Ala Ile Arg Arg
1               5                   10                  15

Ile His Ile Gly Pro Gly Arg Ala Phe Tyr Thr Thr Lys Asn
                20                  25                  30

<210> SEQ ID NO 33
<211> LENGTH: 31
<212> TYPE: PRT
<213> ORGANISM: HIV-1

<400> SEQUENCE: 33

Ala Gln Gly Ala Tyr Arg Ala Ile Arg His Ile Pro Arg Arg Ile Arg
1               5                   10                  15

Arg Ile His Ile Gly Pro Gly Arg Ala Phe Tyr Thr Thr Lys Asn
                20                  25                  30

<210> SEQ ID NO 34
<211> LENGTH: 15
<212> TYPE: PRT
<213> ORGANISM: HIV-1
```

```
<400> SEQUENCE: 34

Arg Ile His Ile Gly Pro Gly Arg Ala Phe Tyr Thr Thr Lys Asn
1               5                   10                  15

<210> SEQ ID NO 35
<211> LENGTH: 66
<212> TYPE: PRT
<213> ORGANISM: HIV-1

<400> SEQUENCE: 35

Pro Ser Asp Lys Lys Ile Glu Gln Tyr Leu Lys Ile Lys Asn Ser
1               5                   10                  15

Ile Ser Cys Asn Pro Asn Ala Asn Pro Asn Ala Asn Pro Asn Ala Asn
                20                  25                  30

Pro Asn Ala Asn Pro Asn Ala Asn Pro Asn Ala Lys Pro Lys Asp Glu
            35                  40                  45

Leu Asp Tyr Glu Asn Asp Ile Glu Lys Lys Ile Cys Lys Met Glu Lys
        50                  55                  60

Cys Ser
65

<210> SEQ ID NO 36
<211> LENGTH: 42
<212> TYPE: PRT
<213> ORGANISM: HIV-1

<400> SEQUENCE: 36

Asp Arg Val Ile Glu Val Val Gln Gly Ala Tyr Arg Ala Ile Arg His
1               5                   10                  15

Ile Pro Arg Arg Ile Arg Gln Gly Leu Glu Arg Arg Ile Gln Arg Gly
                20                  25                  30

Pro Gly Arg Ala Phe Val Thr Ile Gly Lys
            35                  40

<210> SEQ ID NO 37
<211> LENGTH: 15
<212> TYPE: PRT
<213> ORGANISM: HIV-1

<400> SEQUENCE: 37

Ser Ile Thr Lys Gly Pro Gly Arg Val Ile Tyr Ala Thr Gly Gln
1               5                   10                  15

<210> SEQ ID NO 38
<211> LENGTH: 15
<212> TYPE: PRT
<213> ORGANISM: HIV-1

<400> SEQUENCE: 38

Ser Ile His Ile Gly Pro Gly Arg Ala Phe Tyr Ala Thr Gly Asp
1               5                   10                  15

<210> SEQ ID NO 39
<211> LENGTH: 15
<212> TYPE: PRT
<213> ORGANISM: HIV-1

<400> SEQUENCE: 39

Ser Leu Ser Ile Gly Pro Gly Arg Ala Phe Arg Thr Arg Glu Ile
1               5                   10                  15
```

```
<210> SEQ ID NO 40
<211> LENGTH: 15
<212> TYPE: PRT
<213> ORGANISM: HIV-1

<400> SEQUENCE: 40

Ser Ile Ser Ile Gly Pro Gly Arg Ala Phe Phe Ala Thr Thr Asp
1               5                   10                  15

<210> SEQ ID NO 41
<211> LENGTH: 15
<212> TYPE: PRT
<213> ORGANISM: HIV-1

<400> SEQUENCE: 41

Ser Ile Tyr Ile Gly Pro Gly Arg Ala Phe His Thr Thr Gly Arg
1               5                   10                  15

<210> SEQ ID NO 42
<211> LENGTH: 15
<212> TYPE: PRT
<213> ORGANISM: HIV-1

<400> SEQUENCE: 42

Gly Ile Ala Ile Gly Pro Gly Arg Thr Leu Tyr Ala Arg Glu Lys
1               5                   10                  15

<210> SEQ ID NO 43
<211> LENGTH: 15
<212> TYPE: PRT
<213> ORGANISM: HIV-1

<400> SEQUENCE: 43

Arg Val Thr Leu Gly Pro Gly Arg Val Trp Tyr Thr Thr Gly Glu
1               5                   10                  15

<210> SEQ ID NO 44
<211> LENGTH: 15
<212> TYPE: PRT
<213> ORGANISM: HIV-1

<400> SEQUENCE: 44

Ser Ile Arg Ile Gly Pro Gly Lys Val Phe Thr Ala Lys Gly Gly
1               5                   10                  15

<210> SEQ ID NO 45
<211> LENGTH: 15
<212> TYPE: PRT
<213> ORGANISM: HIV-1

<400> SEQUENCE: 45

Gly Ile His Phe Gly Pro Gly Gln Ala Leu Tyr Thr Thr Gly Ile
1               5                   10                  15

<210> SEQ ID NO 46
<211> LENGTH: 15
<212> TYPE: PRT
<213> ORGANISM: HIV-1

<400> SEQUENCE: 46

Ser Thr Pro Ile Gly Leu Gly Gln Ala Leu Tyr Thr Thr Arg Gly
1               5                   10                  15

<210> SEQ ID NO 47
```

```
<211> LENGTH: 15
<212> TYPE: PRT
<213> ORGANISM: HIV-1

<400> SEQUENCE: 47

Ser Thr Pro Ile Gly Leu Gly Gln Ala Leu Tyr Thr Thr Arg Ile
1               5                   10                  15
```